(12) United States Patent
Wewer et al.

(10) Patent No.: US 8,114,609 B2
(45) Date of Patent: Feb. 14, 2012

(54) ADAM12, A NOVEL MARKER FOR ABNORMAL CELL FUNCTION

(75) Inventors: Ulla M. Wewer, Klampenborg (DK); Bent Norgaard-Pedersen, Lyngby (DK); Michael Christiansen, Holte (DK); Jennie Laigaard, Gentofte (DK); Camilla Frohlich, Copenhagen (DK)

(73) Assignees: Statens Serum Institut, Copenhagen (DK); Kobenhavns Universitet, Copenhagen (DK); Harold Wood Hospital, Romford (GB)

( * ) Notice: Subject to any disclaimer, the term of this patent is extended or adjusted under 35 U.S.C. 154(b) by 0 days.

(21) Appl. No.: 12/698,395

(22) Filed: Feb. 2, 2010

(65) Prior Publication Data

US 2010/0190174 A1 Jul. 29, 2010

Related U.S. Application Data

(62) Division of application No. 11/131,952, filed on May 18, 2005, now Pat. No. 7,678,544.

(60) Provisional application No. 60/572,519, filed on May 19, 2004.

(51) Int. Cl.
*G01N 33/53* (2006.01)
*C07K 14/00* (2006.01)
(52) U.S. Cl. .......................... 435/7.1; 530/350
(58) Field of Classification Search .................... 435/7.1; 530/350

See application file for complete search history.

(56) References Cited

FOREIGN PATENT DOCUMENTS
EP 1 524 523 A1 4/2005

OTHER PUBLICATIONS

Biat, et al.; "In Vivo Proteolysis of Serum Insulin-like Growth Factor (IGF) Binding Protein-3 Results in Increased Availability of IGF to Target Cells", J. Clin. Invest.: May 1994; 93; 2286-2290.
Bindra, et al.; "One-Stop Clinic for Assessment of Risk for Trisomy 21 at 11-14 Weeks: A prospective Study of 15 030 pregnancies"; Ultrasound Obstet Gynecol. Sep. 2002; 20(3); 219-25.
Cuckle, et al.; "Appropriate Biochemical Parameters in First-trimester Screening for Down Syndrome"; Prenatal Diagnosis: 1999; 19; 505-512.
Cuckle, et al.; "Estimating a Woman's Risk of Having a Pregnancy Associated with Down's Syndrome using her age and Serum Alpha-fetoprotein level"; Br. J. Obstet gynaecol.: May 1987; 94(5); 387-402.
Gack, et al.; "Preeclampsia Syndrome: Diagnosis and possible Therapeutic Drug Development", Technology Overview German Cancer Research Center In The HelmHoltz Association Sep. 2004; 1-17.
Gilpin, et al.; "A Novel, Secreted Form of Human ADAM 12 (Meltrin) Provokes Myogenesis in Vivo", The Journal of Biological Science: 1998; 273(1); 157-166.
Iba, et al.; "Cysteine-Rich Domain of Human ADAM 12 (Meltrin ) Supports Tumor Cell Adhesion", American Journal of Pathology May 1999; 154(5); 1489-1501.
Kawaguchi, et al.; "ADAM 12 Protease Induces Adipogenesis in Transgenic Mice", American Journal of Pathology May 2002; 160(5); 1895-1903.
Kronqvist, et al.; "ADAM 12 Alleviates the Skeletal Muscle Pathology in mdx Dystrophic Mice", American Journal of Pathology Nov. 2002; 161(5); 1535-1540.
Laigaard, et al.; "ADAM 12: a novel First-Trimester Maternal Serum Marker for Down Syndrome", Prenat Diagn. 2003; 23; 1086-1091.
Laiigaard, et al.; "The Level of ADAM 12-S in Maternal Serum is an Early First-Trimester Marker of Fetal Trisomy 18", Prenatal Diagnosis 2005; 25; 45-46.
Larsen, et al.; "Calculation of roc Curves in Multidimensional likelihood ration based screening with Down's Syndrome as a special case", J Med Screen 1998; 5(2); 57-62.
Laursen, et al.; "Pregnancy-associated Plasma Protein-A (PAPP-A) cleaves insulin-like growth factor binding protein (IGFBP)-5 independent of IGF: Implications for the Mechanism of IGFBP-4 Proteolysis by PAPP-A", Federation of European Biochemical Societies Aug. 2001; 504(1-2); 36-40.
Loechel, et al.; Human ADAM 12 ( Meltrin ) is an Active Metalloprotease:, The Journal of Biological Chemistry Jul. 1998; 273(27); 16993-16997.
Loechel, et al.; "ADAM 12-S Cleaves IGFBP-3 and IGFBP-5 and Is Inhibited by TIMP-3", Biochemical and Biophysical Research Communications 2000; 278; 511-515.
Pabic, et al.; "ADAM 12 in Human Liver Cancers; TGF-β-Regulated Expression in Stellate Cells Is Associated with Matrix Remodeling", Hepatology 2003; 37(5); 1056-1066.

(Continued)

*Primary Examiner* — Karen Carlson
(74) *Attorney, Agent, or Firm* — Vedder Price P.C.; Thomas J. Kowlaski; Deborah L. Lu

(57) ABSTRACT

The present invention provides a method, an assay and a kit for providing an indication of abnormal cell function. It was surprisingly found that the change in the serum ADAM12 concentration in individuals was useful as a prognostic tool to predict the clinical outcome, complications and mortality following an abnormal cell function.
The present inventors describes ADAM12 as a overall general marker for abnormal cell function, and the present inventor for the first time demonstrate that ADAM12 is an important indicator of fetal chromosomal disease and placenta function. Specifically ADAM12 is a good marker for e.g. Downs's syndrome, trisomy 18, preeclampsia, Turner syndrome in both first and second trimester.
The present inventors developed an enzyme-linked immunosorbent assay (ELISA) and a time-resolved immunofluorometric assay for the quantification of ADAM12 in serum.
The present application demonstrates in several examples the variation of the ADAM12 level in fetal abnormality and/or adverse pregnancy outcomes correlated gestational age when compared to normal controls. It is an object of the invention to provide an improvement of the existing marker tests that exhibits a decreased false positive rate.

7 Claims, 44 Drawing Sheets

OTHER PUBLICATIONS

Figure 1:
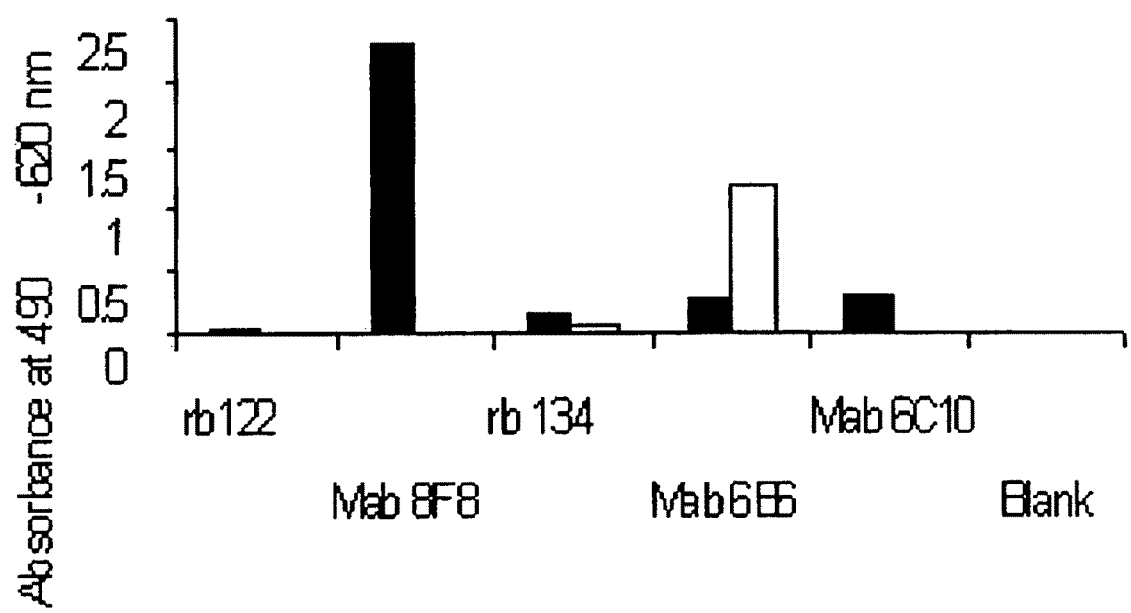

Palomaki, et al.; "Maternal Serum Screening for Fetal Down Syndrome in the United States: a 1992 Survey", Am J Obstet Gynecol Dec. 1993; 169(6); 1558-62.

Palomaki, et al.; "Prospective Intervention Trial of a Screening Protocol to Identify Fetal Trisomy 18 Using Maternal Serum Alpha-Fetoprotein, unconjugated Oestriol, and Human Chorionic Gonadotropin", Prenat Diagn. Nov. 1992; 12(11); 925-30.

Powell-Braxton, et al.; "IGF-I is Required for Normal Embryonic Growth in Mice", Den Dev. 1990; 7; 2609-2617.

Roy, et al.; "ADAM 12 Cleaves Extra cellular matrix Proteins and Correlates with Cancer Status and Stage", The Journal of Biological and Molecular Biology Dec. 2004; 279(49); 51323-51330.

Shi, et al.; "ADAM 12, a Disintegrin Metalloprotease, Interacts with insulin-like Growth Factor-Binding Protein-3", The Journal of Biological Chemistry Jun. 2000; 275(16); 18574-18580.

Van Der Veen, et al.; "A Demographic Approach to the Assessment of Down Syndrome Screening Performance", Prenatal Diagnosis 1997; 17(8); 717-724.

Wald, et al.; "Advances in Antenatal Screening for Down Syndrome", Baillieres Best Prac Res Clin Obstet Gynaecol Aug. 2000; 14(4); 563-80.

Wald, et al.; "Integrated Screening for Down's Syndrome Based on Tests Performed during the First and Second Trimesters", The New England Journal of Medicine Aug. 1999; 341; 461-467.

Claus Hojbjerg Gravholt, et al., Reduced Free IGF-1 And Increased IGFBP-3 Proteolysis In Turner Syndrome: Modulation By Female Sex Steroids, Am J Physiol. Endocrinol. Metab. (2001) vol. 280, p. E-308-E314.

Satsuki Mochizuki, et al., ADAM28 Is Activated By MMP-7 (Matrilysin-1) And Cleaves Insulin-like Growth Factor Binding Protein-3, Biochemical and Biophysical Research Communication (2004) vol. 315, p. 79-84.

Don G. Moerman, Organ Morphogenesis: A Metalloprotease Prepares The Way, Current Biology (1999) vol. 9, p. R701-R703.

Kiyoji Nishiwaki, et al., An NDPase Links ADAM Protease Glycosylation With Organ Morphogenesis in *C. elegans*, Nature Cell Biology (2004) vol. 6, No. 1, p. 31-37.

Sergio, D.J. Pena, et al., Fetal Diagnosis Of Monosomy X (Turner Syndrome) With Methylation-Specific PCR, Prenat Diagn (2003) vol. 23, p. 769-770.

Bernstein, H. et. al. (2003). Comparative localization of ADAMs 10 and 15 in human cerebral cortex normal aging Alzheimer disease and Down syndrome. Journal of Neurocytology, vol. 32, p. 153-160.

Christiansen, M. et. al. (2007). ADAM 12 as a second-trimester maternal serum marker in screening for Down Syndrome. Prenat Diagn, vol. 27, p. 611-615.

Chu, D.C. et. al. (1998). Insulin-like growth factor binding protein-3 in the detection of fetal down syndrome pregnanies. Down Syndrome Screening, vol. 91, No. 2, p. 192-195.

Seals, D. et. al. (2003). The ADAMs family of metalloproteases: multidomain proteins with multiple functions. Genes and Development, vol. 17, p. 7-30.

A

B

ADAM12, A NOVEL MARKER FOR ABNORMAL CELL FUNCTION

RELATED APPLICATIONS

This application is a divisional of U.S. patent application Ser. No. 11/131,952 filed May 18, 2005, now U.S. Pat. No. 7,678,544 which claims priority from U.S. Provisional Patent Application 60/572,519 filed May 19, 2004.

The above referenced application, and each document, application or patent cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF THE INVENTION

The overall general inventive concept of the present invention relates to a method for screening for abnormal cell function in an individual by determining the level of ADAM12.

The present invention especially provides methods for screening for pathologies in pregnant and non-pregnant individuals that are based on detection of ADAM12 in a biological sample from said individual, in particular methods for screening for altered focal proliferation states in pregnant and/or non-pregnant individuals, which include detecting levels of ADAM12, are described.

BACKGROUND OF THE INVENTION

Abnormal cell function is a general overall problem in many life style- and genetic-related diseases, such as cancers and many of the known chromosomal abnormalities.

Down syndrome, also referred to as trisomy 21, is the most common congenital cause of severe mental retardation and occurs as a result of abnormal cell function due to the presence of an extra chromosome 21. Previously, fetal Down syndrome could be determined by diagnostic procedures including amniocentesis or chorionic villus sampling and karyotyping.

These diagnostic procedures are invasive and involve risk for both the woman and the fetus. For this and other reasons, amniocentesis or chorionic villus sampling and karyotyping are not routinely performed during all pregnancies. Instead, one or more screening methods may be utilized to determine when the risk to the pregnancy warrants the risk of undergoing an invasive diagnostic procedure.

The incidence of e.g. Down syndrome increases significantly with increasing maternal age. Historically, the prenatal detection of Down syndrome has focused on pregnant women at and over the age of 35, at which ages the risks of Down syndrome approach or exceeds (at maternal age >40 years) the risks of diagnostic procedures utilized to detect fetal Down syndrome. The incidence of several other fetal chromosomal disorders, e.g. Turner's syndrome and triploidies do not depend on maternal age. Therefore the standard method of prenatal screening for fetal trisomy 21, 18 and 13 has involved selecting women for diagnostic amniocentesis on the basis of maternal age. Age, however, is an inadequate screening criterion in that only about 20% of all Down syndrome pregnancies can be detected by carrying out amniocentesis and karyotyping on the 5% of pregnant women most at risk, that is, those aged 35 years or greater. And, because in actual clinical practice only about half of the women aged 35 years or greater undergo amniocentesis and karyotyping, fewer than 10% of Down syndrome pregnancies are prenatally diagnosed.

In 1984 an association between lowered maternal blood alphafetoprotein (AFP) levels and fetal Down syndrome was discovered. The association between lowered maternal blood AFP levels and fetal Down syndrome presented the opportunity to use a non-invasive blood-screening test in the detection of Down syndrome cases in young, apparently unaffected families where approximately 80% of Down syndrome cases occur.

Another method for screening-involves measuring the level of unconjugated estriol (UE) in maternal blood. Later an association between elevated maternal blood levels of the Intact HCG molecule and the alpha subunit of HCG (HCG is composed of two subunits) and fetal Down syndrome was discovered.

Since the early 1990s, a multiple marker blood test has been used to screen for e.g. Down syndrome. A common version of that test is the three marker triple test. The triple screen measures AFP, human chorionic gonadotropin (hCG) and unconjugated estriol ($uE_3$) in the serum of pregnant women.

Such prenatal screens, as the triple screen, can be used either to reduce the need for amniocentesis or to increase genetic defect detection for the same amount of amniocentesis. The triple screen combines the analysis of three markers from serum to reduce false positive results, which result in the performance of unnecessary invasive procedures, and false negatives in which serious genetic defects, such as, trisomy 21, go undetected.

In women under 35, the double screen (AFP and hCG) can pick up about half of Down syndrome cases and a large proportion of other chromosome defects during the second trimester. The triple screen (AFP, hCG and $uE_3$) increases the detection rate by another 5-10% of Down syndrome and a further increase in the detection of many other serious chromosome defects, thus decreasing the number of false-positives.

However, such rates mean that the double and triple screens still fail to detect a significant number of Down syndrome and other aneuploidy affected pregnancies and this test is limited to the second trimester.

Although the triple screen has a suggested screening period of 15 to 20 weeks gestation, such screening has been recommended between weeks 16-18 to maximize the window for spinal bifida detection (Canick and Knight).

A 1992 survey of prenatal maternal serum screening for AFP alone or for multiple analyses reported that very few such screenings occurred in the thirteenth or earlier week of gestation (Palomaki et al.)

These screens thus suffers from the additional problem that once a risk of a genetic defect is predicted, and amniocentesis or another invasive prenatal definitive diagnostic procedure is performed to diagnose the genetic defect, such as Down syndrome, it is at an advanced date of gestation, when termination of a pregnancy can be more physically and emotionally trying for the mother, and when certain less traumatic abortion procedures, such as, vacuum curettage, may not be available. Recently, methods for screening for chromosomal disease in first trimester by using a combination of the serological markers pregnancy associated plasma protein A (PAPP-A) and the free β human chorionic gonadotropin (βhCG) and the ultrasound marker nuchal translucency (Combined first trimester screening) has been demonstrated to function in week 8-14 with a detection rate for Downs syndrome of ca. 80%-90% for a false positive rate of 3-5% (Bindra et al., 2002).

Theoretically, it has been predicted that the combined use—in the same pregnancy—of first and second trimester testing would be the most effective screening with a detection rate for Downs' syndrome of >90% for a false positive rate of ca. 1% (Wald et al 1999).

However, in order to improve the detection rate and or reduce the false positive rate new markers that may either supplement existing screening markers or replace them are in need.

The limitations of the state of the art screens and the adverse consequences of unnecessary, potentially harmful and expensive invasive prenatal diagnostic procedures, such as, amniocentesis or chorionic villous sampling, have led to a search for more discriminatory markers for prenatal screening of Down syndrome and other aneuploidies.

Several biochemical markers are under investigation as screening markers for fetal disease and adverse pregnancy outcome, e.g. Down's syndrome and other chromosomal diseases in early pregnancy. Others that has come into routine use is an IGF-dependent IGFBP-4 and IGF-independent IGFBP-5 protease namely pregnancy-associated plasma protein-A (PAPP-A), which has also been shown to be of potential clinical importance as a marker of growth retardation and preterm birth.

Although these screening methods do detect fetal Down syndrome, there is a need and a desire for a method, which detects a greater percentage of fetal Down syndrome cases. Thus, the instant invention represents a significant advance in the field of prenatal diagnosis.

ADAM12 has been detected by western blotting in pregnant serum, but not in non-pregnant serum (Shi et al. and, Loechel et al.), and the mRNA for ADAM12 is particularly abundant in placenta (Gilpin et al.).

In placenta, ADAM12 is produced by the trophoblasts. ADAM12 is a disintegrin and metalloprotease, which is upregulated in breast and colon cancer and their liver metastasis (Iba et al 1999, Le Pabic et al 2003) and urinary levels of ADAM12 correlate with disease status and stage in breast cancer (Roy et al 2004).

The present inventors published in 2003 that ADAM12 was a first-trimester maternal serum marker for Down syndrome (Laigaard et al. 2003) and in 2005 that the level of ADAM12-S in maternal serum is an early first trimester marker for fetal trisomy 18 (Laigaard et al. 2005).

EP 1 524 523 describes that expression, particular transcription, of ADAM12 is strongly upregulated in placentae in preeclamptic patients. However, EP 1 524 523 does not describe changes in the serum ADAM12 concentration, and in particular the correlation of such levels to gestational age.

If the ADAM12 concentration is not normalised with respect to gestational age—i.e. is converted to gestational age independent values—e.g. by dividing the ADAm12 concentration measured in maternal serum with the median value for the particular gestational age (multiple of median—MoM) at which the sample was obtained—the inter-individual variation of ADAM12 concentration values will reduce the discriminatory ability of the marker.

SUMMARY OF THE INVENTION

The present invention provides a method, an assay and a kit for providing an indication of abnormal cell function. It was surprisingly found that the change in the serum ADAM12 concentration in individuals was useful as a prognostic tool to predict the clinical outcome, complications and mortality following an abnormal cell function.

The present inventors describes ADAM12 as a overall general marker for abnormal cell function, and the present inventor for the first time demonstrate that ADAM12 is an important indicator of foetal and placental development, function and changes in the level of ADAM12 may reflect the presence, classification or progression of disease.

The present inventors developed an enzyme-linked immunosorbent assay (ELISA) and an automated time-resolved immunofluorometric assay for the quantification of ADAM12 in serum.

The present application demonstrates that in three studies, the first comprising maternal serum samples from 18 first trimester Down's syndrome pregnancies, and the second comprising 226 first trimester maternal serum samples from Down syndrome pregnancies in first trimester and 89 Down syndrome pregnancies in second trimester and the third comprising 10 maternal serum samples from first trimester trisomy 18 pregnancies, ADAM12 is reduced in first trimester DS and trisomy 18 maternal sera and increased in second trimester DS pregnancies. ADAM12 may thus serve as a maternal serum risk marker for fetal disease. Furthermore it is demonstrated in 160 maternal serum samples from first trimester pregnancies where the women developed preeclampsia that the ADAM12 concentration in maternal serum was reduced and that ADAM12 may be used as a marker of adverse outcome of pathological pregnancies. It is thus an object of the present invention to provide an improvement of the existing marker tests that exhibits a decreased false positive rate or improved detection rate of chromosomal disease or adverse pregnancy outcome.

DETAILED DESCRIPTION OF THE INVENTION

ADAM12 in Cellular Interactions

ADAM12 is a multidomain protein with cell adhesion, metalloprotease, and signaling activities. ADAM12 has a restricted spatio-temporal expression pattern in several tissue compartments during development, regeneration, and in disease.

The present inventors herein demonstrate that ADAM12 is associated with and induces a phenotype that augments the aggressive behavior of tumor cells.

Thus using a breast tumor model in mice, the present inventors demonstrated that mice develop tumors faster when they express ADAM12 than when they do not. Also the tumor burden of ADAM12-expressing tumors are bigger than non-ADAM12 expressers, and thus a higher aggressive behavior of tumor cells.

Importantly, the present inventors demonstrate that in a mouse model of breast carcinoma, ADAM12 induces a more aggressive tumor growth pattern. In examples described below, ADAM12 transgenic mice were generated that express ADAM12 under the MMTV-promoter (mouse mammary virus (MMTV) long terminal repeat promoter/enhancer (LTR) which drives the expression of ADAM12 in the mammary gland.

Upon breeding of these ADAM12 mice with a tumor prone mouse strain MMTV-PyMT, a new strain of mice, MMTV-PyMT-ADAM12 was generated. The development of breast tumors in parental MMTV-PyMT mice was compared to that in MMTV-PyMT-ADAM12 mice.

The absolute and relative tumor burden was evaluated (g tumor tissue and g tumor tissue/weight of the mouse, respectively) and the tumor-free period determined as the time until tumor masses could be observed by palpation. The present inventors found that the MMTV-PyMT-ADAM12 mice had a significantly more aggressive course than the parental MMTV-PyMT mice.

At the molecular level, the present inventors found that, depending on the cell type, ADAM12 decreases cell proliferation and sensitizes cells to programmed cell death (non-malignant cells) but importantly not that of malignant tumor cells.

Thus, depending on the cellular context and epitopes exposed, ADAM12 appears to mentor the delicate balances of cell adhesion receptor functionality at the cell surface, which is of critical importance for cancer cell behavior.

Breast carcinoma cells expressing ADAM12 is resistant to programmed cell death whereas non-tumorigenic "normal" cells induced to express ADAM12 are sensitive.

The present inventors have previously shown that "normal" stromal cells (3T3-L1) upon expression of ADAM12 is more sensitive to programmed cell death than their control cells (Kawaguchi et al 2003).

They subsequently tested the difference between such "normal cells" and malignant breast carcinoma cells. Surprisingly, they found that malignant MCF-7 breast carcinoma cells expressing ADAM12 are resistant to programmed cells death. This indicates that tumor cells, that we know over-express ADAM12, have an advantage to the normal cells and therefore further show that ADAM12 contribute to an aggressive phenotype.

Generation of MCF-7 Cells Expressing ADAM12

Full length ADAM12-L lacking the cytoplamatic tail (ADAM12-Δcyt) was cloned into the Xho I site of the retroviral Tet response vector (pRevTRE). The created plasmid was transfected into the packing cell line 293-10A1 cells. MCF-7 cells were transduced with sterile filtered retrovirus containing supernatant from the 293-10A1 packaging cell line in the presence of 8 µg/mL polybrene. Transduced cells were selected in the presence of 200 µg/mL Hygromycin. Established cell lines were kept routinely in DMEM, 10% FBS-tet, 100 µg/mL G418, 100 µg/mL hygromycin, 100 ng/ml doxycycline, pen/strep. Removal of doxycycline from the growth medium induced expression of the stabile transfected ADAM12-Δcyt gene and hence ADAM12 protein.

Testing the Sensitivity of Breast Carcinoma Cells to Programmed Cell Death

Apoptotic index measured as percentage of Hoescht-stained cells with condensed nuclei in ADAM12-Δcyt expressing cultures and control MCF-7 after 24 hr after UVC radiation (60 J/m2) in combination with 48 hr treatment with 5 µM cycloheximidde and 100 ng/ml TNFα. The percentage of cells with condensed nuclei was estimated. The present inventors found that less than 5% of MCF-7 cells were undergoing programmed cell death under these conditions, and this was not changed following TNF-α/UV treatment.

Abnormal Cell Function

The present inventors thus suggest that ADAM12 is a overall general marker for abnormal cell function, therefore in one aspect, the present invention relates to a method for screening for abnormal cell function in an individual said method comprising the steps of:
  a) providing a body sample from the individual
  b) determining the level/value of ADAM12 in said sample by detecting
    1) ADAM12 polypeptide and/or
    2) a polynucleotide coding for ADAM12, and/or
    3) specific ADAM12 protease activity, preferably by detecting cleavage of IGFBP-3, a derivative thereof, or any other suitable substrate for ADAM12, including its sheddase activity.
  c) comparing said level/value with a reference level/predetermined value;
  d) identifying whether the level/value is different from said reference level/predetermined value and
evaluating whether said individual has an increased risk of abnormal cell function, if the level is different from the reference level.

In the present context the term "abnormal cell function" relates to changes at the cellular level of cell division, cell survival, cell adhesion, cell migration, cytoskeletal organisation, extracellular matrix assembly and cell differentiation. These changes are elements in many pathophysiological processes such as but not limited to malignancy, abnormal fetal and placenta development, growth disturbances in general, as well as organ specific response to injury and stress.

These pathophysiological processes are reflected by the ADAM12 level in tissue or tissue fluids, and said level is thus a marker of disease. ADAM12 is a marker of pre-clinical as well as clinical diseases. The level of ADAM12 reflects presence and risk of disease, prognosis, and helps in defining treatment or prophylaxis.

In one embodiment the present invention relates method for screening for abnormal cell function in an individual according to the present application, wherein said reference level is indicative of a normal physiological condition of said individual.

In another embodiment the present invention relates method for screening for abnormal cell function in an individual according to the present application, wherein said reference level value is indicative of a condition, which is an abnormality of said individual.

The level of ADAM12 may be used as a marker if it deviates from, i.e. is lower than or higher than—a clinically defined cut-off, e.g. a value of ADAM12 concentration or a number of copies of a specific ADAM12 nucleic acid. The level of ADAM12 may also be converted to a likelihood ratio and either used alone or in conjunction with other markers to define the likelihood of a clinical condition or disease associated parameter, e.g. survival.

A clinical cut-off value and or normal distribution of ADAM12 levels are defined for each condition and may be a defined percentile of the values or the distribution of values obtained in healthy individuals or in clinically or physiologically well defined persons. In some instances, e.g. pregnancy, gestational age specific normal intervals will have to be defined using statistical techniques.

Fetal Health

Another goal of this present invention was to determine whether ADAM12 concentration is a useful indicator of fetal health, since fetal development is one of the most active cell growth stages of mammals.

The present application demonstrates that in 18 and 226 first trimester Down's syndrome pregnancies the concentration of ADAM12 was decreased and in 89 second trimester samples ADAM12 was increased.

In 10 maternal serum pregnancies with a trisomy 18 fetuses the concentration of ADAM12 was reduced making ADAM12 a promising marker of trisomy 18. This was confirmed in 143 cases with 730 controls as shown in the examples below.

The examples also demonstrates that ADAM12 is a first and second trimester marker for preclampsia, Turner syndrome and non-Turner sex chromosome abnormalities. Furthermore, it is demonstrated that using ADAM12 in conjunction with other markers, used in both first and second trimester, adds greatly to the discriminatory performance of such markers.

Hence, ADAM12 is a promising marker for Down's syndrome and other fetal chromosomal diseases. The first trimester ADAM12 maternal serum concentration of ADAM12 was reduced in pregnancies with preeclampsia making ADAM12 a promising marker of preeclampsia and placental disease and adverse pregnancy outcome.

Thus, in one aspect the present invention relates to a method for screening for fetal abnormality in a fetus said method comprising the steps of:
 a) providing a body sample from the individual
 b) determining the level of ADAM12 in said sample by detecting
  1) ADAM12 polypeptide and/or
  2) a polynucleotide coding for ADAM12 expression, and/or
  3) specific ADAM12 protease activity, preferably by detecting cleavage of IGFBP-3, a derivative thereof, or any other suitable substrate for ADAM12.
 c) comparing said level with a reference;
 d) identifying whether the level is different from said reference and
evaluating whether the fetus has an increased risk of fetal abnormality and/or adverse pregnancy outcome, if the level is different from the reference.

In the present context the term "fetal abnormality and adverse pregnancy outcome" relates to fetal chromosomal disease—both in the form of chromosomal structural abnormalities and mosaics of such, malformations, monogenic or polygenic disease, developmental deviations from normal, congenital disease, any fetal disease, any pathological conditions of the placenta, intrauterine growth retardation, preeclampsia, HELPP syndrome, eclampsia, premature birth, fetal cardiac disease, abortion and fetal death.

Thus, one embodiment of the present invention relates to a method according to the present invention, wherein said fetal abnormality is selected from the group consisting of trisomy 21, trisomy 18, trisomy 13, preeclampsia, intra uterine growth retardation, ectopic pregnancy, open spina bifida, neural tube defects, ventral wall defects, Edwards Syndrome, Pateaus Syndrome, Turner Syndrome, non-Turner sex chromosome abnormalities, Monosomy X or Kleinefelter's Syndrome, triploidies, mosaic conditions and Open Spina Bifida.

One embodiment of the present invention relates to a method according to the present invention, wherein said fetal abnormality is an altered growth state selected from the group consisting of a growth promoting state and a growth inhibiting state. Such fetal abnormalities can be manifested as chromosomal diseases, or pathologically focal proliferation states.

One embodiment of the present invention is the use of ADAM12 to establish whether a woman is pregnant.

One embodiment of the present invention relates to the use of ADAM12 as a marker of cardiac disease, either cellular hypertrophy or vasculogenesis.

One embodiment of the present invention relates to the use of ADAM12 to classify, prognostify, identify and characterize hypertrophic, dilated, arrhythmogenic right ventricular and restrictive cardiomyopathy and left ventricular cardiac hypertrophy.

One embodiment of the present invention is the use of ADAM12 as a screening marker for cardiac disease.

In one embodiment, the present invention relates to a method according to the present invention, wherein the fetal abnormality and/or adverse pregnancy outcome is selected from the group consisting of Down's syndrome (trisomy 21), trisomy 18, trisomy 13, triploidies, mosaicisms, preeclampsia, Turner syndrome and non-Turner sex chromosome abnormalities.

In a presently preferred embodiment, the present invention relates to a method according to the present invention, wherein the fetal abnormality and/or adverse pregnancy outcome is Down's syndrome.

In a presently preferred embodiment, the present invention relates to a method according to the present invention, wherein the fetal abnormality and/or adverse pregnancy outcome is Turners syndrome.

In a presently preferred embodiment, the present invention relates to a method according to the present invention, wherein the fetal abnormality and/or adverse pregnancy outcome is non-Turner sex chromosome abnormalities (NTSCA), i.e. 47 XXY, 47 XXX, 47 XYY or triploidies.

In a presently preferred embodiment, the present invention relates to a method according to the present invention, wherein the fetal abnormality and/or adverse pregnancy outcome is preeclampsia.

In a presently preferred embodiment, the present invention relates to a method according to the present invention, wherein the fetal abnormality and/or adverse pregnancy outcome is trisomy 18.

One embodiment of the present invention relates to a method according to the present invention, wherein gestational age independent (MOM) or value of ADAM12 is calculated for use in risk assessment in any fetal or placenta disease.

In a particular preferred embodiment, the present invention relates to a method wherein the gestation age independent ADAM12 (MOM) is used in conjunction with biometric, serological or clinical information to derive a risk for developing pre-eclampsia. Furthermore, the same type of method used to derive prognostic and diagnostic information of the other adverse pregnancy outcomes described above.

In the present context the term "individual" relates to both the mother and the unborn progeny.

In the present context the term "chromosomal disease" relates to any autosomal or sexchromosome triploidies, aneuplodies or mosaics of such, i.e. trisomy 21, trisomy 18, trisomy 13, Turners syndrome, Klinefelters syndrome etc., and to other structural chromosome abnormalities, e.g. translocations and deletions.

In the present context, the term "fetus" relates to any kind fetus from the time of conception to the birth of the child, and thus includes the stages often referred to as embryo, describing the earlier stages, and fetus (or foetus).

In the present context the term "individual" relates in its broadest aspect to any person in risk of an abnormal cell function, in particular and individual carrying a foetus. Though the present examples describe the measurements of ADAM12 in a maternal sample, the present invention can be adapted to measurements direct on the fetus, thus in one embodiment the present invention also relates to a method according to the present invention wherein the individual is the fetes.

In the present context the term "pathology" relates to something abnormal, such as abnormal cell function, but also the structural and functional deviations from the normal that constitute disease or characterize a particular disease.

In other words the present invention could also be described as a method of diagnosing a clinical condition or diagnosing predisposition to said clinical condition in a mammalian fetus comprising the steps of
  a) providing a body fluid sample from the mother of said fetus; and
  b) measuring the level of ADAM12 in said body fluid sample; and
  c) diagnosing the clinical condition or diagnosing predisposition to the clinical condition, wherein the level of ADAM12 above or below a predetermined value is indicative of the clinical condition or predisposition to the clinical condition.
wherein the clinical condition is selected from the group consisting of Down's syndrome, preeclampsia and acute coronary syndrome, including unstable angina myocardial infarction and any of the fetal abnormality and/or adverse pregnancy outcome as described herein.

In another embodiment the present invention relates to a screening method for determining a pregnant woman's risk of carrying a fetus with Down syndrome comprising
  measuring said pregnant woman's maternal blood for the level of ADAM12 during the first trimester and/or the second trimester of pregnancy and comparing said level ADAM12 to reference values of the level for ADAM12 during the first trimester of pregnancy in: (1) pregnant women carrying Down syndrome fetuses and (2) pregnant women carrying normal fetuses, said comparison being indicative of said pregnant woman's risk of carrying a fetus with Down syndrome, wherein a higher level of ADAM12 is indicative of a higher probability of carrying a fetus with Down syndrome.

The Sample

In the present context, the term "sample" relates to any liquid or solid sample collected from an individual to be analyzed. Preferably, the sample is liquefied at the time of assaying.

In another embodiment of the present invention, a minimum of handling steps of the sample is necessary before measuring the concentration of ADAM12. In the present context, the subject "handling steps" relates to any kind of pretreatment of the liquid sample before or after it has been applied to the assay, kit or method. Pre-treatment procedures includes separation, filtration, dilution, distillation, concentration, inactivation of interfering compounds, centrifugation, heating, fixation, addition of reagents, or chemical treatment.

In accordance with the present invention, the sample to be analyzed is collected from any kind of mammal, including a human being, a pet animal, a zoo animal and a farm animal.

In yet another embodiment of the present invention, the sample is derived from any source such as body fluids.

Preferably, this source is selected from the group consisting of milk, semen, blood, serum, plasma, saliva, urine, sweat, ocular lens fluid, cerebral spinal fluid, cerebrospinal fluid, ascites fluid, mucous fluid, synovial fluid, peritoneal fluid, vaginal discharge, vaginal secretion, cervical discharge, cervical or vaginal swab material or pleural, amniotic fluid and other secreted fluids, substances and tissue biopsies from organs such as the brain, heart and intestine.

In one embodiment of the present invention relates to a method according to the present invention, wherein said body sample or biological sample is selected from the group consisting of blood, urine, pleural fluid, oral washings, vaginal washings, cervical washings, tissue biopsies, and follicular fluid.

Another embodiment of the present invention relates to a method according to the present invention, wherein said biological sample is selected from the group consisting of blood, plasma and serum.

In a presently preferred embodiment of the present invention relates to a method according to the present invention, wherein said biological sample is serum.

The sample taken may be dried for transport and future analysis. Thus the method of the present invention includes the analysis of both liquid and dried samples.

In one embodiment of the present invention, a maternal serum sample is taken from a pregnant woman. The maternal blood level of ADAM12 is then measured by conventional analytical methods, such as immunological methods known to the art.

The maternal serum level of ADAM12 is then compared to a set of reference data to determine whether the patient is at an increased risk of carrying a fetus with e.g. Down syndrome.

To increase detection efficiency, gestational age and the maternal blood level of ADAM12 may be compared to a set of reference data to determine whether the patient is at increased risk of carrying a fetus with e.g. Down syndrome.

Determining the ADAM12 Level

The determination of the level of an identified protein, such as ADAM12 in a sample can be obtained by any detecting assay known to the skilled addressee, such as but not limited to immunoassays, gene expression assays and other known arrays.

The ADAMs (A Disintegrin And Metalloprotease) constitute a multidomain glycoprotein family with proteolytic and cell-adhesion activities.

Human ADAM12 exists in two forms ADAM12-L (long) and ADAM12-S (short), the latter being the secreted form of ADAM12. ADAM12-S differs from ADAM12-L at the C-terminal end in that it does not contain the transmembrane and cytoplasmatic domains. ADAM12-S binds to and has proteolytic activity against insulin-like growth factor binding protein (IGFBP)-3 and, to a lesser extent, IGFBP-5. In vitro cleavage of the 44-kDa IGFBP-3 by ADAM12 yields several fragments of 10 to 20 kDa and is independent of insulin-like growth factor (IGF) I and II. IGF I and II are proinsulin-like polypeptides that are produced in nearly all fetal and adult tissues. Lack of IGF I and II causes fetal growth retardation in mice. The cleavage of IGFBPs into smaller fragments with reduced affinity for the IGFs reverses the inhibitory effects of the IGFBPs on the mitogenic and DNA stimulatory effects of the IGFs. Seventy-five percent of the IGFs are bound to IGFBP-3 in plasma.

Thus, one embodiment of the present invention relates to determination of level of ADAM12 polypeptide in a sample, wherein the ADAM12 polypeptide can be both the ADAM12-L (long) and ADAM12-S (short) form.

It is further understood by those of ordinary skill in the art, that ADAM12 is a member of a complex family of at least 33 similar genes. It is in addition possible that multiple forms of ADAM12 with small differences in amino acid sequences, or other small differences, may be synthesized. It is further possible that in e.g. Down syndrome, one or more of the ADAM12 genes are expressed, thereby producing a unique variant or variants (previously referenced as nicked or fragmented or aberrant forms) ADAM12.

According to the present invention these variants could be measured by conventional immunological techniques for measuring ADAM12. An assay produced to measure the specific ADAM12 variant, or variants, associated with Down syndrome may result in even further enhancement of detection efficiency.

Another embodiment of the present invention relates to determination of level of ADAM12 polypeptide in a sample in the form of mRNA originating from ADAM12 expression, including all splice variants of ADAM12.

The finding that the serum concentration of IGFBP-3 decreases markedly from 6 weeks gestation to term, and that the pregnancy-specific proteolytic cleavage results in 29 to 30, 19 and 15 kDa fragments, is consistent with the finding that ADAM12-S cleaves IGFBP-3 into 10-20 kDa fragments and thus may be one of the putative IGFBP-3 proteases in pregnancy serum.

Because ADAM12 is an IGFBP-3 protease and IGFBP-3 is the most abundant IGFBP in serum. The proteolysis of IGFBP-3 would stimulate growth by increasing levels of bioavailable IGF I and II. Also, since PAPP-A and ADAM12 are both IGFBP-5 proteases synthesized by the placenta, ADAM12 is a logical candidate for investigation as an indicator of fetal abnormalities.

The concentration of bioavailable insulin-like growth factor (IGF) I and II is important to fetal growth. It is regulated by insulin-like growth factor binding proteins (IGFBP) 1 through 6. Proteolytic cleavage of IGFBP-3 takes place in human pregnancy serum; accordingly, IGFBP-3 serum levels decrease markedly during pregnancy. ADAM12 (A Disintegrin And Metalloprotease) is an IGFBP-3 and IGFBP-5 protease and is present in human pregnancy serum.

Furthermore, our finding that the concentration of ADAM12 increases 60-fold during pregnancy adds to the explanation of the decrease in IGFBP-3 concentration.

Additional support is provided in the results reported by Irwin et al. (2000) showing that human placental trophoblasts secrete a disintegrin and metalloprotease that cleaves IGFBP-3, is active at neutral and alkaline pH, and sensitive to o-phenanthroline. The protease secreted by trophoblasts could be ADAM12 because mRNA for ADAM12 is particularly abundant in the placenta, and has the same apparent characteristics The finding by Langford et al. (1995) showing elevated levels of IGFBP-3 protease in third trimester gestational serum in pregnancies with utero-placental insufficiency, and the suggested role of the IGFBP-5 protease, PAPP-A, as a predictor of intrauterine growth retardation make ADAM12 an interesting candidate as a predictor of adverse pregnancy outcomes in addition to DS.

Thus, another embodiment of the present invention relates to determination of level of ADAM12 polypeptide in a sample, wherein said level is calculated by measuring the specific ADAM12 protease activity, preferably by detecting cleavage of IGFBP-3, a derivative thereof, or any other suitable substrate for ADAM12.

Placental leucine aminopeptidase (P-LAP), a type-II transmembrane protease responsible for oxytocin degradation during pregnancy, is converted to a soluble form through proteolytic cleavage. The goal of this study was to determine the nature of the P-LAP secretase activity. The hydroxamic acid-based metalloprotease inhibitors GM6001 and ONO-4817 as well as the TNF-α protease inhibitor-2 (TAPI-2) reduced P-LAP release, while tissue inhibitors of metalloproteinase (TIMP)-1 and TIMP-2, which are matrix metalloproteinase inhibitors, had no effect on P-LAP release in Chinese hamster ovary (CHO) cells stably overexpressing P-LAP, thus indicating possible involvement of ADAM (a disintegrin and metalloproteinase) members in P-LAP shedding. Furthermore, overexpression of ADAM9 and ADAM12 increased P-LAP release in P-LAP-CHO transfectants. Immunohistochemical analysis in human placenta demonstrated strong expression of ADAM12 in syncytiotrophoblasts, while little expression of ADAM9 was detected throughout the placenta. These results suggest ADAM members, at least including ADAM12, are involved in P-LAP shedding in human placenta.

Thus, another embodiment of the present invention relates to determination of level of ADAM12 polypeptide in a sample, wherein said level is calculated by measuring the specific ADAM12 protease activity, preferably, but not exclusively, by detecting P-LAP shedding in human placenta.

The Reference

In order to determine the clinical severity of the abnormal cellular function, means for evaluating the detectable signal of ADAM12 measured involves a reference or reference means. The reference also makes it possible to count in assay and method variations, kit variations, handling variations and other variations not related directly or indirectly to the concentration of ADAM12.

In the context of the present invention, the term "reference" relates to a standard in relation to quantity, quality or type, against which other values or characteristics can be compared, such as e.g. a standard curve.

The reference data reflects the maternal blood level of ADAM12 for pregnant women carrying fetuses with Down syndrome (also referred to as affected) and/or the maternal blood level of ADAM12 for pregnant women carrying normal fetuses (also referred to as unaffected). As will be generally understood by those of skill in the art, methods for screening for fetal Down syndrome are processes of decision making by comparison. For any decision making process, reference values based on patients having the disease or condition of interest and/or patients not having the disease or condition of interest are needed.

In the present invention the reference values are the maternal blood level of the measured marker or markers, for example, ADAM12, in both pregnant women carrying Down syndrome fetuses and pregnant women carrying normal fetuses. A set of reference data is established by collecting the reference values for a number of samples. As will be obvious to those of skill in the art, the set of reference data will improve by including increasing numbers of reference values.

In one preferred embodiment of the present invention, the reference means is an internal reference means and/or an external reference means.

In the present context the term "internal reference means" relates to a reference which is not handled by the user directly for each determination but which is incorporated into a device for the determination of the concentration of ADAM12, whereby only the 'final result' or the 'final measurement' is presented. The terms the "final result" or the "final measurement" relates to the result presented to the user when the reference value has been taken into account.

In a further embodiment of the present invention, the internal reference means is provided in connection to a device used for the determination of the concentration of ADAM12.

In yet an embodiment of the present invention the device is selected from the group consisting of an assay, a stick, a dry-stick, an electrical device, an electrode, a reader (spectrophotometric readers, IR-readers, isotopic readers and similar readers), histochemistry, and similar means incorporating a reference.

In the present context, the term "external reference means" relates to a reference which is handled directly by the user in order to determine the concentration of ADAM12, before obtaining the 'final result' or the 'final measurement'.

In yet a further embodiment of the present invention external reference means are selected from the group consisting of a table, a diagram and similar reference means where the user can compare the measured signal to the selected reference means. The external reference means relates to a reference used as a calibration, value reference, information object, etc. for ADAM12 and which has been excluded from the device used.

One embodiment of the present invention relates to a method according to the present invention, wherein said reference level/predetermined value is indicative of a normal physiological condition of said individual.

One embodiment of the present invention relates to a method according to the present invention, wherein said reference level/predetermined value is indicative of a condition is a fetal abnormality of said individual.

Although any of the known analytical methods for measuring the maternal blood level of ADAM12 will function in the present invention, as obvious to one skilled in the art, the analytical method used for ADAM12 must be the same method used to generate the reference data for ADAM12. If a new analytical method is used for ADAM12, a new set of reference data, based on data developed with the method, must be generated. Thus, the technique utilized to analyze the blood should be the same for the reference data and the samples to be screened.

Risk Assessment

The present inventors have successfully developed a new ELISA method to measure ADAM12 throughout pregnancy. The concentration of ADAM12 in maternal serum increases 60-fold from first trimester to term, and is markedly decreased in the first trimester in pregnancies with fetal Down's syndrome and increased in second trimester in pregnancies with Down's syndrome. Table 1 shows that ADAM12 appears to be an efficient maternal serum marker for DS. The discrimination is better than with any other established first trimester marker. Likewise the discrimination in second trimester is better than or comparable to that of the best known markers in that gestational age window.

To determine whether the patient is at increased risk of carrying a fetus with e.g. Down syndrome, a cut-off must be established. This cut-off may be established by the laboratory, the physician or on a case by case basis by each patient.

The cut-off level can be based on several criteria including the number of women who would go on for further invasive diagnostic testing, the average risk of carrying a Down syndrome fetus to all the women who go on for further invasive diagnostic testing, a decision that any woman whose patient specific risk is greater than a certain risk level such as e.g. 1 in 400 or 1:250 (as defined by the screening organisation or the individual woman) should go on for further invasive diagnostic testing or other criteria known to those skilled in the art.

The cut-off level could be established using a number of methods, including: percentiles, mean plus or minus standard deviation(s); multiples of median value; patient specific risk or other methods known to those who are skilled in the art.

In another embodiment of the present invention, which results in a detection of a greater number of the cases of fetal Down syndrome, the serum are analyzed for both ADAM12 and βhCG and or PAPP-A or other first trimester markers for first trimester risk assessment of fetal disease and with AFP and or hCG or unconjugated estriol or other markers in second trimester for second trimester risk assessment utilizing a dual or triple analyte assay, exemplified by dual or triple labeled time-resolved immunofluorometric assays.

Although any of the known analytical methods for measuring the maternal blood levels of these analytes will function in the present invention, as obvious to one skilled in the art, the analytical method used for each marker must be the same method used to generate the reference data for the particular marker. If a new analytical method is used for a particular marker, a new set of reference data, based on data developed with the method, must be generated.

Preferably, a patient specific risk of carrying a fetus with Down syndrome is calculated using Bayes rule, the patients a priori risk, and the relative frequencies for unaffected and affected pregnancies which are determined by incorporating the patient's quantitative levels on each analyte (ADAM12 and PAPP-A and βhCG and other markers in first trimester and ADAM12, AFP, hCG, uE3 and inhibin A and other markers in second trimester) along with the patient's gestational age, into the probability density functions developed for the reference data using multivariate discriminant analysis or multidimensional truncated normal (or other) distributions.

The multivariate discriminant analysis and other risk assessments can be performed on the commercially available computer program statistical package Statistical Analysis system (manufactured and sold by SAS Institute Inc.) or by other methods of multivariate statistical analysis or other statistical software packages or screening software known to those skilled in the art.

According to a preferred embodiment of the present invention a maternal serum sample is taken from a pregnant woman. The maternal serum levels of ADAM12 and other markers (hereinafter referred to as "markers") are then measured by conventional immunological methods known to the art when the markers are serological markers and with other relevant methods known to people skilled with the techniques when the markers are other biometric markers, e.g. ultrasound measurements, i.e. nuchal translucency.

Although any of the known analytical methods for measuring the maternal serum levels of these markers will function in the present invention, as obvious to one skilled in the art, the analytical method used for each marker must be the same method used to generate the reference data for the particular marker. If a new analytical method is used for a particular marker, a new set of reference data, based on data developed with the method, must be generated.

For the purposes of the risk assessment or discriminant analysis an assumption is made as to the prior probability of Down syndrome in the general unselected population. Generally, the prior probability is approximately 1 in 800. For the multivariate discriminant analysis and risk assessment a decision is made as to what risk cutoff level constitutes a positive test result. For example, if it is desirable to perform further diagnostic tests on a pregnant woman who has a e.g. 1 in 400 or greater possibility of carrying a Down syndrome fetus, then when the results of the discriminant analysis indicate that a pregnant woman has a e.g. 1 in 400 or greater possibility of carrying a Down syndrome fetus, the pregnant woman is considered to have a positive test result. If a positive test result is indicated, the patient should be counseled about further diagnostic tests to confirm the presence of Down syndrome.

As obvious to one skilled in the art, in any of the embodiments discussed above, changing the risk cut-off level of a positive or using different a priori risks which may apply to different subgroups in the population, could change the results of the discriminant analysis for each patient.

The stability tests described herein demonstrate that ADAM12 is highly stable with routine handling; thus, the present inventors conclude that ADAM12 is an attractive analyte for clinical use. The data presented here suggest that ADAM12 is a potentially valuable marker for use in prenatal screening.

Ranges

The present inventors developed an enzyme-linked immunosorbent assay (ELISA) for the quantification of ADAM12 in serum. The assay range was 42 to 667 µg/l. Recombinant ADAM12 was used as the standard for calibration. Likewise an automated time-resolved immunofluorometric assay with an analytical range from 78 to 1248 ug/L ADAM12 was developed using the Perkin Elmer AutoDelfia platform.

Thus, in one embodiment the present invention relates to an assay according to the present invention, wherein the detection level range is from 20 µg/l to 2000 µg/l, such as 20 µg/l to 1500 µg/l, 20 µg/l to 1000 µg/l, 20 µg/l to 800 µg/l, 20 µg/l to 600 µg/l, 20 µg/l to 400 µg/l, 20 µg/l to 200 µg/l, 50 µg/l to 2000 µg/l, 100 µg/l to 200 µg/l, 200 µg/l to 800 µg/l, 400 µg/l to 1000 µg/l or 100 µg/l to 1200 µg/l. As the skilled addressee would recognize the detection level would be increased by applying more sensitive detection assays such as but not limited to PCR or mass spectrometry.

The present inventors found that ADAM12 was highly stable in serum. Serum concentration increased from e.g. 180 µg/l at week 8 of pregnancy to e.g. 670 µg/l at 16 weeks in one study, however from week 10-16, the present inventors found highly variable—but decreasing—levels that were well described by a third degree polynomial spline function. From week 18 the levels increased to reach a median of 12,000 µg/l at term, as described in Example 1.

In 18 first trimester Down's syndrome pregnancies the concentration of ADAM12 was decreased, thus the median Multiple of Mean (MoM) value was 0.14 (0.01-0.76). A detection rate for fetal Down's syndrome of 82% for a screen positive rate of 3.2% and a 1:400 risk cut-off was found by Monte Carlo estimation using ADAM12 and maternal age as screening markers, as described in Example 1.

In 226 first trimester DS samples—examined at a later gestational age—the median MoM was 0.79 but clearly lower in week 10-12, than week 13-14—suggesting that ADAM12 is a particularly good marker in very early first trimester. In 89 second trimester DS pregnancy maternal serum samples a median MoM of 1.79 was found suggesting that ADAM12 is a good marker for DS pregnancies in second trimester, as described in Example 5.

In 160 first trimester serum samples obtained from women developing preeclampsia in second trimester—obtained from the Copenhagen First Trimester Screening Study the mean log MoM ADAM12 was significantly reduced to −0.066 (range: −1.009-0.441), as described in Example 4. In 67 cases of preeclampsia, obtained from Harold Wood Hospital, UK, the MoM ADAM12 was likewise significantly reduced to 0.90 in first trimester and increased to 1.14 in second trimester as detailed in Example 13.

In trisomy 18 pregnancies the median ADAM12 MoM was found to be reduced to 0.29 in early first trimester in a Danish study—as detailed in Example 6 and to a mean logMoM ADAM of −0.097 in first trimester and increased to a mean logMoM ADAM12 of 0.312 in second trimester—as detailed in example 7.

In trisomy 13 pregnancies the mean logMoM ADAM12 was reduced to −0.221 in first trimester and increased to 0.170 in second trimester as detailed in Example 8.

In Turner syndrome pregnancies the mean logMoM ADAM12 was −0.177 in first trimester and 0.172 in second trimester as detailed in Example 9.

In NON-Turner sex chromosome abnormalities, e.g. 47 XXX, 47 XXY, and 47 XYY the logMoM ADAM12 was reduced to −0.238 in first trimester and increased to 0.212 in second trimester as detailed in Example 10.

log MoM

If the ADAM12 concentration is not normalised with respect to gestational age—i.e. is converted to gestational age independent values—e.g. by dividing the ADAm12 concentration measured in maternal serum with the median value for the particular gestational age (multiple of median—MoM) at which the sample was obtained—the inter-individual variation of ADAM12 concentration values will reduce the discriminatory ability of the marker.

The log MoM values of ADAM12 differ characteristically—compared to control pregnancies—in different periods of gestation in the examined conditions:

In trisomy 21: ADAM12 is low in gestational week 5-10. Similar to controls in weeks 11-12 and increased from week 13-20.

In trisomy 18, 13, 45X0 (Turner syndrome), Non-Turner sex-chromosome abnormalities and triploidies the level of log MoM ADAM12 is reduced in first trimester and increased in second trimester.

In preeclampsia the level of logMoM ADAM12 is decreased in first and increased in second trimester compared to controls.

The Methods

Immunoassays, in their most simple and direct sense, are binding assays. Antibody binding to ADAM12 can be detected by any immunoassay means known in the art. Preferably, antibody binding is detected by an assay selected from the group consisting of protein microarray assay, radioimmunoassay (RIA), enzyme-linked immunosorbent assay (ELISA), fluoroimmunoassay, immunofluorometric assay, and immunoradiometric assay.

Most preferably, antibody binding is detected by ELISA.

Enzyme-Linked Immunosorbent Assay (ELISA)

ELISA relies on a similar principle to RIA but depends on an enzyme rather than a radioactive label. More specifically, an enzyme conjugated to the antibody is able to generate a detectable signal in the presence of a suitable substrate.

In one exemplary ELISA, the antibodies useful for the methods of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody, which binds the antigen that is linked to a detectable label. This type of ELISA is a simple "sandwich ELISA". Detection may also be achieved by the addition of a second antibody that binds the antigen, followed by the addition of a third antibody that has binding affinity for the second antibody, with the third antibody being linked to a detectable label.

In another exemplary ELISA, the samples suspected of containing the antigen are immobilized onto the well surface and then contacted with the antibodies. After binding and appropriate washing, the bound immune complexes are detected. Where the initial antibodies are linked to a detectable label, the immune complexes may be detected directly. Again, the immune complexes may be detected using a second antibody that has binding affinity for the first antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or the antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably in the order of 25 to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. Or the label may be detectable using time-resolved immunofluorescence.

Protein Microarray Assay

Another embodiment of the present invention relates to detecting the amount of at least one form of ADAM12 present in the sample detected specifically using a protein microarray assay. This means that the capturing of the at least one form of ADAM12 is performed using antibodies or fragments thereof and wherein the detection is performed using a mass spectrometer, such as a MALDI-TOF spectrometer. Furthermore, the binding of at least one form of ADAM12 onto a surface can be utilized as catching mechanism and the detection can be made using a mass spectrometer, such as a SELDI-TOF spectrometer.

The Kit

When measuring the concentration of ADAM12 in a sample, whether a quick determination is required or not, a kit comprising the necessary means is provided.

In the present context, the term "kit" relates to a set of means which are useful for a particular purpose, in this case the purpose of the kit is to permit the determination of the concentration of ADAM12 in a sample. The set of means typically comprises means for obtaining the sample being measured, means for storing or holding the sample obtained, means for providing a detectable signal relative to the amount ADAM12 present in the sample and means for evaluating the detectable signal of ADAM12 measured, but also other means may be added.

In one embodiment of the present invention, the kit comprises at least one of means selected from the group consisting of means for obtaining the sample being measured, means for storing or holding the sample obtained, means for providing a detectable signal relative to the amount and/or concentration of ADAM12 present in the sample and means for evaluating the detectable signal of ADAM12 measured, such as two of the means, e.g. three of the means and such as four of the means.

When using the kit the means for obtaining the sample being measured comprises e.g. a syringe for obtaining a blood sample or a syringe or a scalpel for obtaining a tissue sample or other conventional means for obtaining a sample perfectly known by the person skilled in the art. Subsequently, the sample is transferred to the means for storing or holding the sample and the sample is analyzed using the means for providing a detectable signal relative to the amount of ADAM12 present in the sample. The signal obtained is analyzed and evaluated in order to determine the clinical severity of the cellular growth disorder and thereby providing a prognosis or diagnosis for the disease and/or providing the best possible prevention and/or treatment of any complications caused by the disorder.

The means for providing a detectable signal relative to the concentration of ADAM12 present in the sample is selected from the group consisting of an assay, an array, a stick, a dry-stick, an electrical device, an electrode, a reader (such as a spectrophotometric reader, an IR-reader, an isotopic reader and similar readers), histochemistry, and similar means.

Other means for providing a detectable signal relative to the concentration of ADAM12 present in the sample may be correlation to the mRNA level of ADAM12 in said sample, such as but not limited to Real-Time PCR.

Automated Assay

In order to reduce assay variation and human handling and clerical errors, it will be advantageous to use the present invention as part of a semi- or fully automated analytical system preferably also where the handling of clinical data and analytical results as well as risk calculation and quality control of analytical results as well as of risk assessment is performed in an integrated semi-automated system, e.g. as the combination of the Autodelfia and Autodelfia express analytical platforms with the software Lifecycle by the same manufacturer. We have shown that the ADAM12 assay functions on the Autodelfia platform. The invention emodies any semi- or fully automated assay procedure quantifying ADAM12. The invention also embodies assay systems imploding dried reagents or dried coated plates. Furthermore, blood or tissue constituents stored on filter paper, and extracted prior to quantisation of ADAM12.

Multiplex analytical platforms e.g. Luminex Technologies are also part of the present invention for measurement of the ADAM12 value.

Timing of the Screening

As described herein, the methods of this invention provide for more discriminatory, cheaper, less invasive and more geographically accessible means for prenatal screening for fetal aneuploidies, than had been provided by former methods of screening based on maternal serum markers.

Further, an important embodiment of the present invention is that the maternal screening methods of the instant invention can be used not only in the second trimester as maternal serum screening methods are predominantly used, but also in the first trimester.

As indicated herein, there are disadvantages to second trimester testing, in that delays in confirming a fetal aneuploidy diagnosis result in more traumatic abortion procedures being necessitated. Also, the emotional attachment and expectations of the pregnant woman and her family for a healthy baby, grow during the pregnancy, making the abortion decision more difficult later in the gestational term.

One embodiment of the present invention relates to a method according to the present invention, wherein ADAM12 is assessed as a first trimester marker.

One embodiment of the present invention relates to a method according to the present invention, wherein ADAM12 is assessed as a second trimester marker.

Using ADAM12 as a marker in first and second trimester increases the performance of these tests and will result in a more precise definition of risk pregnancies that should be offered an invasive investigation to diagnose fetal disease (i.e. amniocentesis or chorionic villous sampling followed by karyotyping). Using ADAM12 both in first and second trimester may reduce the risk of the individual woman participating in a screening program of losing her fetus as a result of being a false positive in the screening. Using ADAM12-alone or in combination with other markers—in early first trimester, prior to gestational week 11, may improve performance of first trimester screening to the extent that the performance will be similar to that of "Integrated screening" which is considered the best available at present. However the Integrated screening has the disadvantage that the risk is reported to the pregnant woman in second trimester. This is unfortunate as late risk reporting is less desirable from medical as well as psychological grounds.

As the discriminatory power of the ADAM12 in trisomy 21 pregnancies is good—i.e the MoM ADAM12 is reduced prior to week 11 or increased after week 12—the marker is useful for trisomy 21 screening outside the "window of usefulness" from week 10(11)-11(12). This is in analogy with marker such as PAPP-A, hCG and SP1 and other that have "windows of uselessness" in other parts of gestation. The window of uselessness of ADAM12 has only been documented for trisomy 21 so it is not necessary to recommend the use outside week 10(11)-11(12) when screening for other fetal or maternal conditions.

Thus, in one embodiment that present invention relates to a method, wherein the sample is obtained prior to gestational age of week 11 and/or after gestational age of week 12.

Combination to Other Known Markers

In a presently preferred embodiment, measuring ADAM12 in combination with one or more of the following markers in maternal serum or plasma and biometric markers may reduce the number of false positive and increase the discriminatory power over the known tests:

alpha feto-protein (AFP)
unconjugated oestrol (uE3)
human chorionic gonadotrophin (hCG)
free alpha sub-unit of hCG (free α-hCG)
free beta sub-unit of hCG (free β-hCG)
beta-core hCG
hyperglycosylated hCG (ITG)
placental growth hormone (PGH)
inhibin, preferably dimeric inhibin-A (inhibin A)
pregnancy-associated plasma protein A (PAPP-A)
Complexes of PAPP-A with proMBP (proform of major basic protein) ProMBP
ProMBP complexes with angiotensinogen and/or complement factors and split products
Schwangerschaftsprotein 1(SP1)
Cancer antigen 125(CA125)
Prostate specific antigen (PSA)
Leukocyte enzymes
fetal DNA
fetal RNA
fetal cells
stem cells
oestradiol
Ultrasound markers
Nuchal translucency
Femur length
Absence of nasal bone
Hyperechogenic bowel
Echogenic foci in the heart
Choroids plexus cysts
Hydronephrosis
Fetal malformations
Steroids
Peptides
Chemokines
Interleukins (e.g. IL-6, IL-4, IL-1)
Tumor necrosis factor
Transforming growth factor alpha and beta
Acute phase reactants
C-reactive protein
Fibronectin
Maternal or fetal Single nucleotide polymorphisms, e.g. promoter region polymorphisms in TNFbeta and mannan-binding lectin
Complement components
HLA-G
HLA molecules Thus in one embodiment, the present invention relates to a method as described herein, wherein the ADAM12 level is combined with values from at least one marker selected from the group defined above.

ADAM12 Antibodies

It is also generally understood that in generating antibodies specific for ADAM12, some antibodies will be specific for the protein and some will be specific for carbohydrate associated antigenic sites. The measurement of the level of ADAM12 referred to throughout the description of the invention includes using antibodies specific for either the protein or the carbohydrate associated antigenic sites or any other site on ADAM12.

We have effectively used ELISA assay techniques to measure ADAM12 to distinguish between trisomy 21 affected and unaffected pregnancies. Detection efficiency for trisomy 21 as high as >80% for a false positive rate of 3% has been estimated using ADAM12 and maternal age as risk markers. As is well known to those skilled in the art, the use of antibodies to quantitate specific analytes may result in degrees of cross-reactivity with a distinct yet similar substance. Hence, the distinction between affected and unaffected cases may be influenced by the presence of an aberrant form of ADAM12 which, because of some degree of cross-reactivity with the antibodies being used, is being detected. An aberrant form of ADAM12 may be designated as a new biochemical substance.

Trisomy 21 affected cases may also be characterized by an aberrant form of ADAM12 in which case those skilled in the art will be capable of developing specific antibodies to such aberrant forms which may result in a further enhancement of detection efficiency for this syndrome.

Alternatively, Down syndrome affected cases may also be characterized by a fragmented form (or fragment) of ADAM12 comprising an incomplete portion of the amino acids that comprise ADAM12. As will be understood by those of ordinary skill in the art, assays utilized to measure ADAM12 will also detect fragments of ADAM12 if the epitope, or epitopes, utilized in the assays are present in the fragment of ADAM12.

The present invention is not limited to the embodiments discussed above but rather includes all of the possible embodiments and combination of markers disclosed in the following examples.

All the features described herein relating to the methods and/or assays of the present invention are also applicable as embodiments relating to kits and vice versa, thus in one embodiment, the present invention relates to a kit for use in an assay as defined in the present invention.

As will be apparent, preferred features and characteristics of one aspect of the invention may be applicable to other aspects of the invention.

All patent and non-patent references cited in the present application, are hereby incorporated by reference in their entirety.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

FIGURE LEGENDS

FIG. 1

Tests to determine the optimal coating antibodies. Monoclonal antibodies (Mab) 8F8 and 6E6, and Polyclonal rabbit antibodies (rb) 122 and 134 were used to coat ELISA dishes. The biotinylated antibody used was 6E6 (black columns), or 8F8 (white columns).

FIG. 2

Freeze thaw. Results of the analysis of serum samples after repeated freezing and thawing.

FIG. 3

Standard curve for ADAM12. Standard curves of absorbance at 490-620 nm, using 6E6 for coating and 8F8 as the biotinylated antibody for detection.

FIG. 4.

Stability of ADAM12 in Serum. The stability of ADAM12 at different storage temperatures is shown over time after venipuncture and centrifugation.

FIG. 5

First trimester scatter plot of log 10 ADAM12 versus days. Black triangles are values for Down's syndrome.

FIG. 6

Appearance of palpable tumors in MMTV-PyMT and MMTV-PyMT-ADAM12-S transgenic mice. Age at which a mammary tumor is first palpable in each transgenic strain. Also shown are the number of animals analyzed for each strain (n).

FIG. 7

Appearance of palpable tumors in MMTV-PyMT and MMTV-PyMT-ADAM12-Δcyt transgenic mice. Age at which a mammary tumor is first palpable in each transgenic strain. Also shown is the number of animals analyzed for each strain (n).

FIG. 8

The absolute tumor mass (g). MMTV-PyMT-ADAM12-Δcyt transgenic mice had a significantly more aggressive potential than the parental MMTV-PyMT; P=0.015.

FIG. 9

The relative tumor burden (g tumor tissue/weight of the mouse). MMTV-PyMT-ADAM12-Δcyt transgenic mice had a significantly more aggressive potential than the parental MMTV-PyMT, P=0.087.

FIG. 10

The absolute tumor mass (g). MMTV-PyMT-ADAM12-S transgenic mice had a significantly more aggressive potential than the parental MMTV-PyMT; P=0.012.

FIG. 11

The relative tumor burden (g tumor tissue/weight of the mouse). MMTV-PyMT-ADAM12-S transgenic mice had a significantly more aggressive potential than the parental MMTV-PyMT, P=0.014.

FIG. 12

Scatter plot of MoM ADAM12 versus MoM PAPP-A.

FIG. 13

C. Scatter plot of log MoM PAPP-A versus log MoM ADAM12. Filled triangles show the values for Down's syndrome.

FIG. 14

Scatter plot of log MoM ADAM12 versus log MoM β hCG.

FIG. 15

ROC-curve analysis of combinations of screening markers in first trimester ADAM12, maternal age, β hCG, PAPP-A, and Nuchal Translucency (NT).

ROC-curve analysis for Screen Positive Rate <10%.

FIG. 16

Second trimester ADAM12. Plot of log ADAM12 concentration versus gestational age. Filled triangles are values for Down's syndrome.

FIG. 17

Medians of ADAM12 in control pregnancies and the third degree polynomial spline function.

FIG. 18

Distribution of ADAM12 MoM values in DS pregnancies as a function of gestational age.

FIG. 19

Correlation between Log ADAM12 and Log free beta MoMs in first trimester T21 without weight correction.

Figure 20:
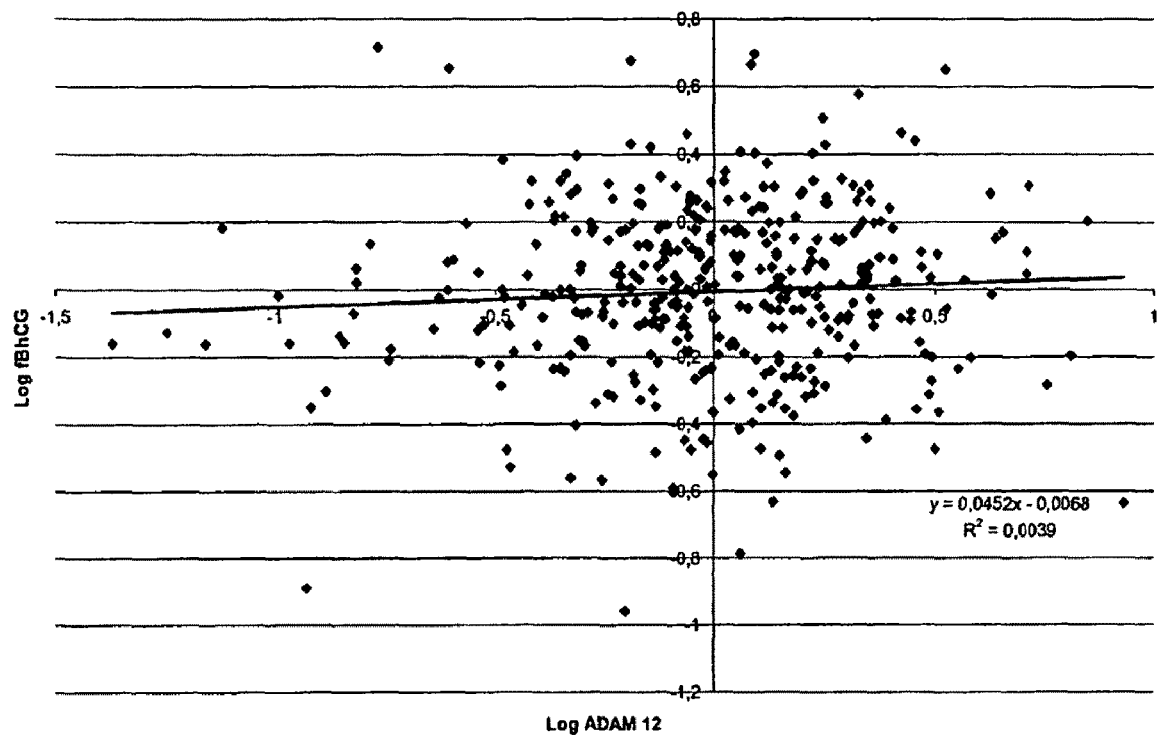
Figure 21:
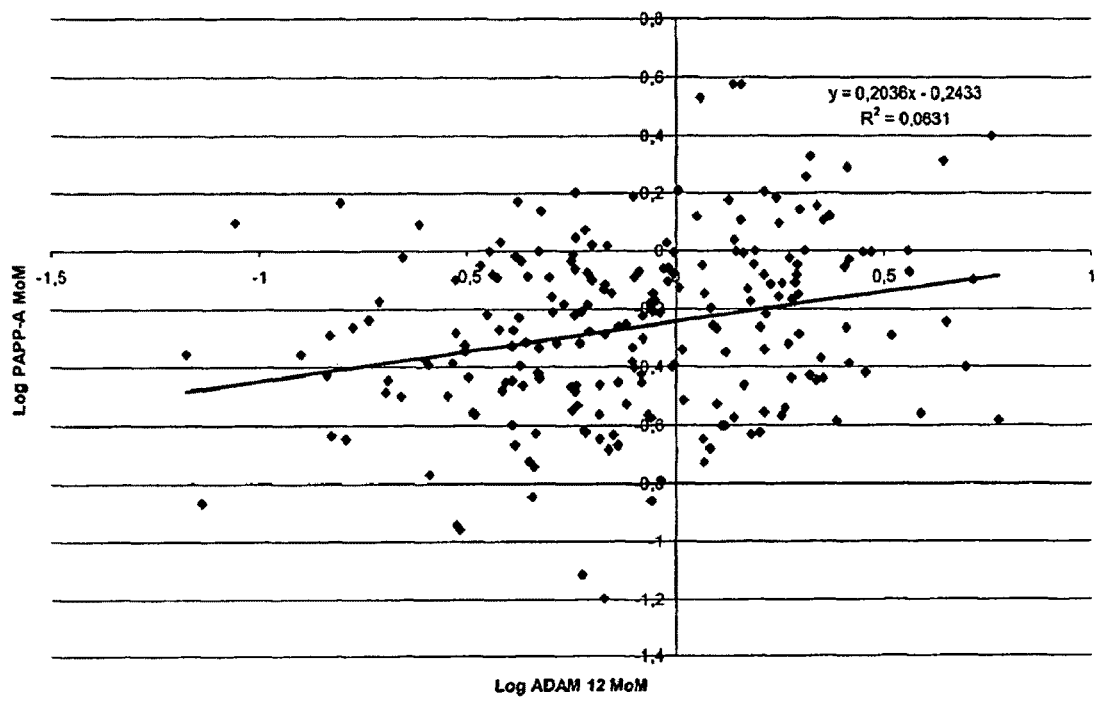
Figure 22:
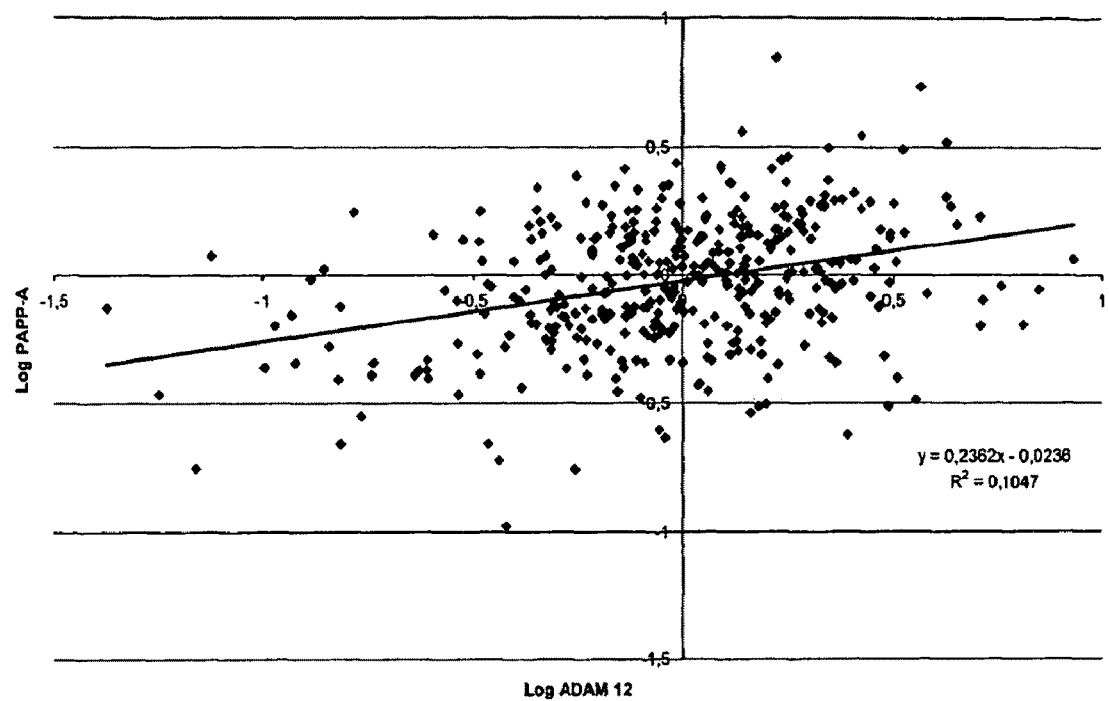
Figure 23:
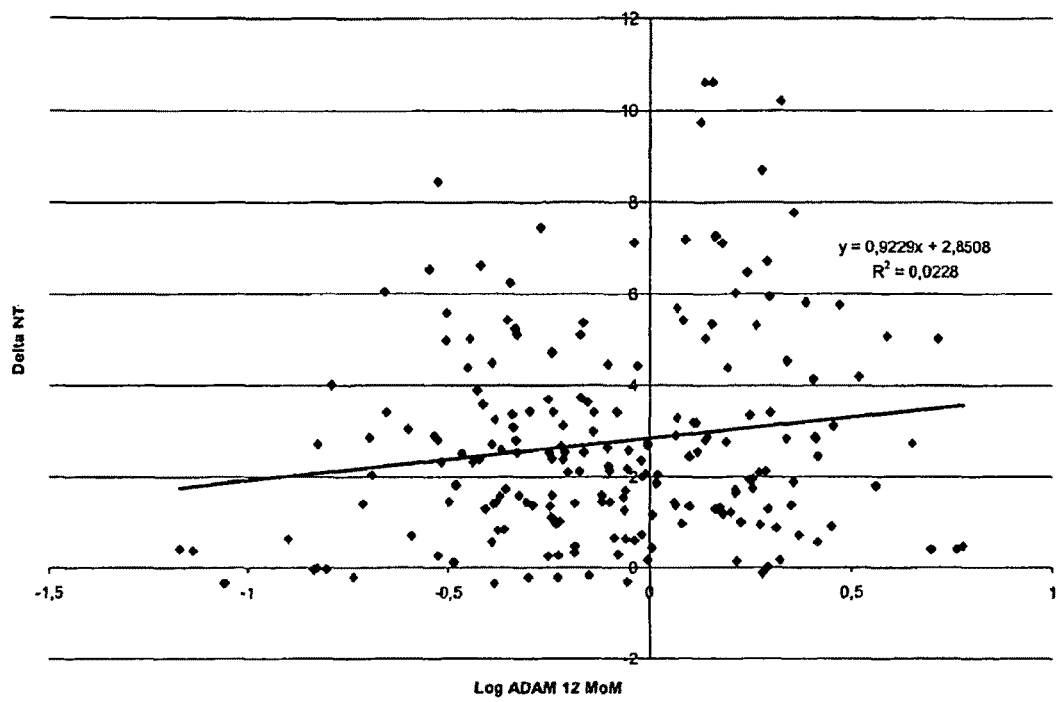
Figure 24:
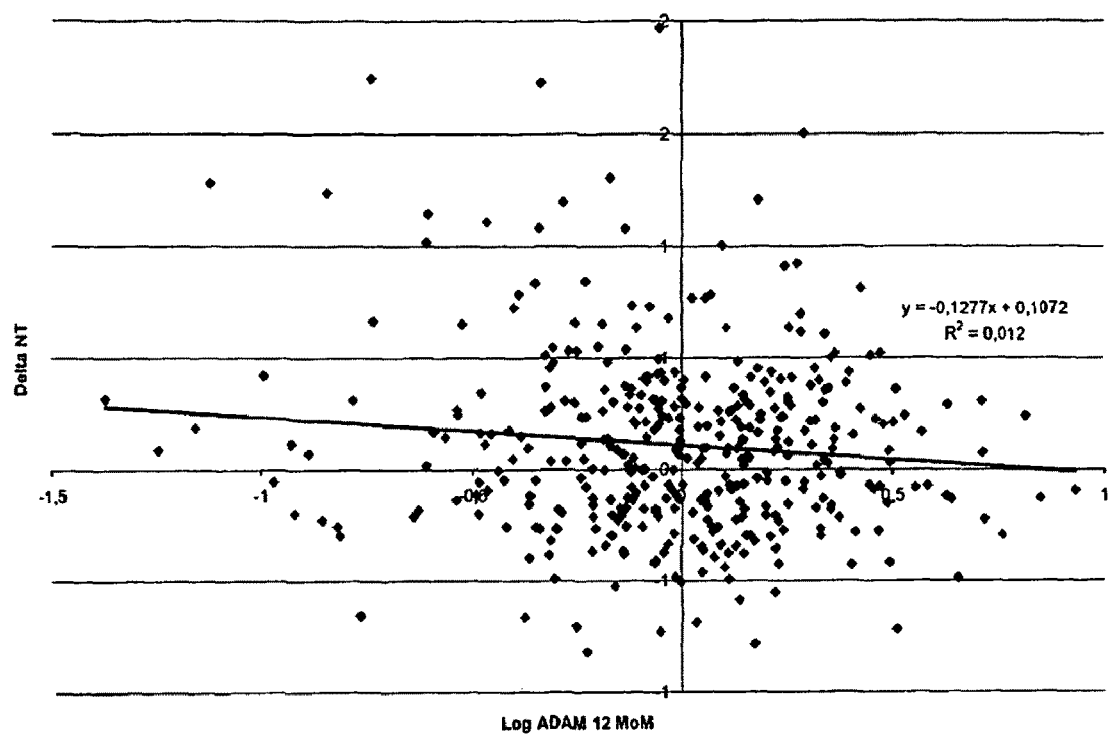
Figure 25:
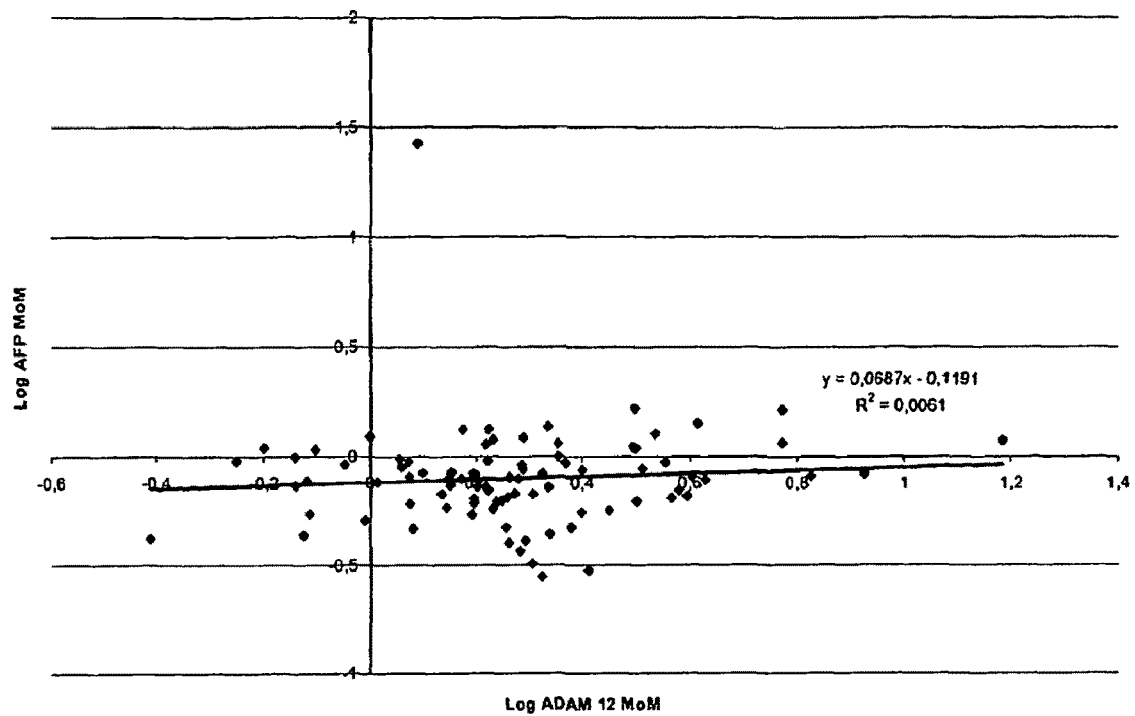
Figure 26:
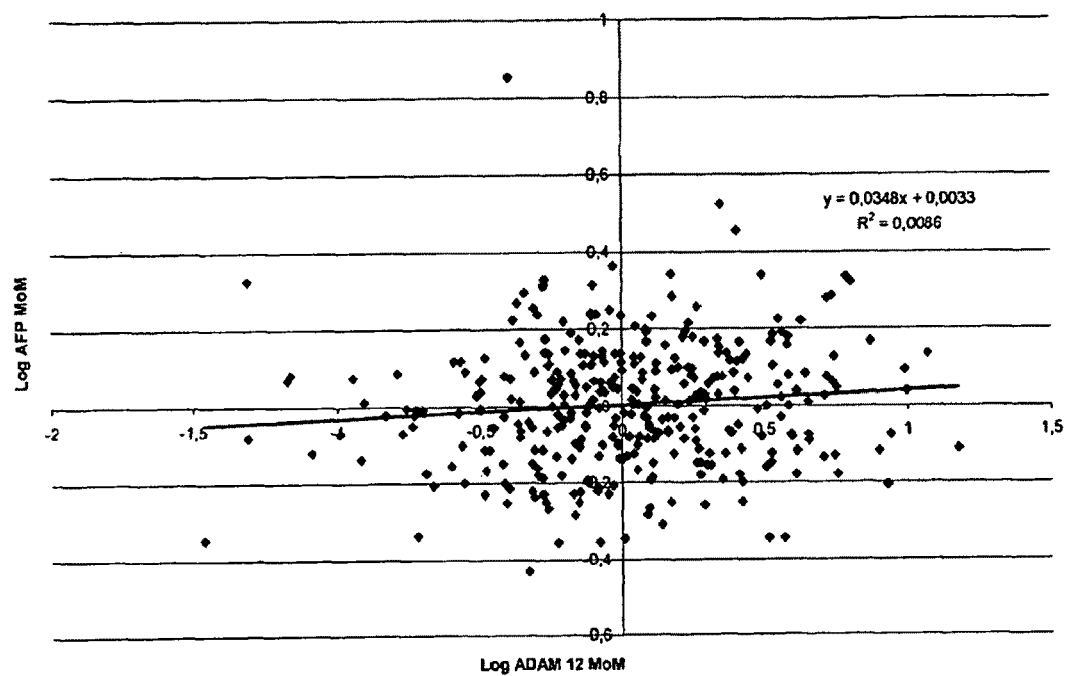
Figure 27:
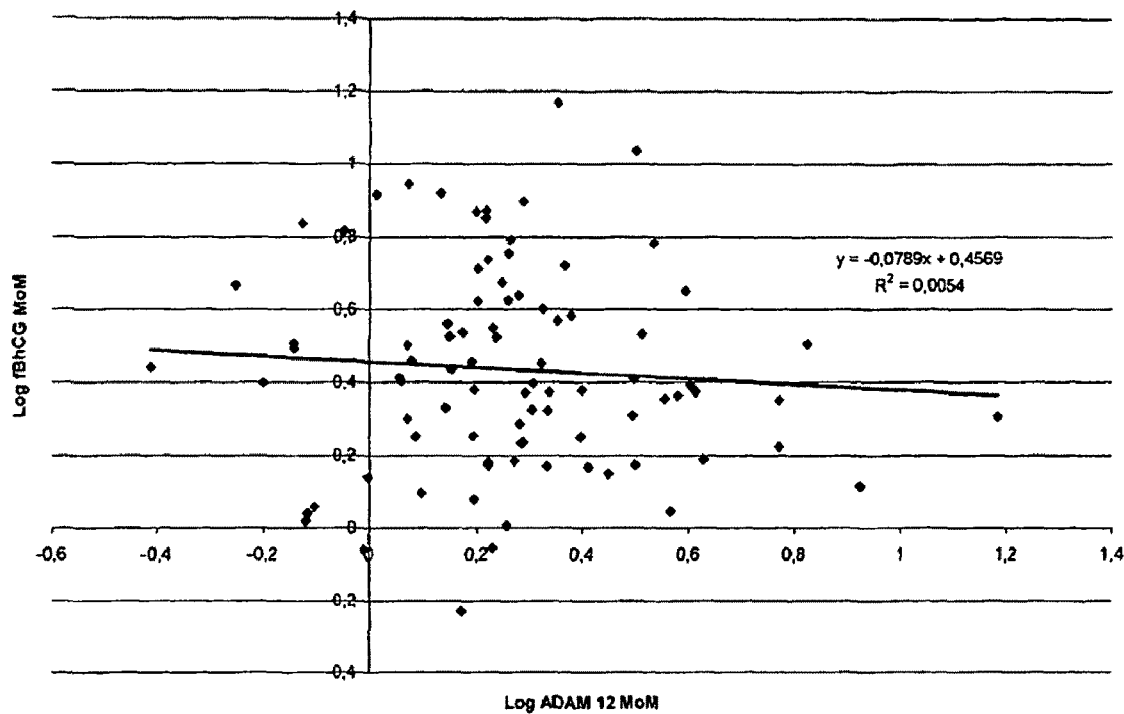
Figure 28:
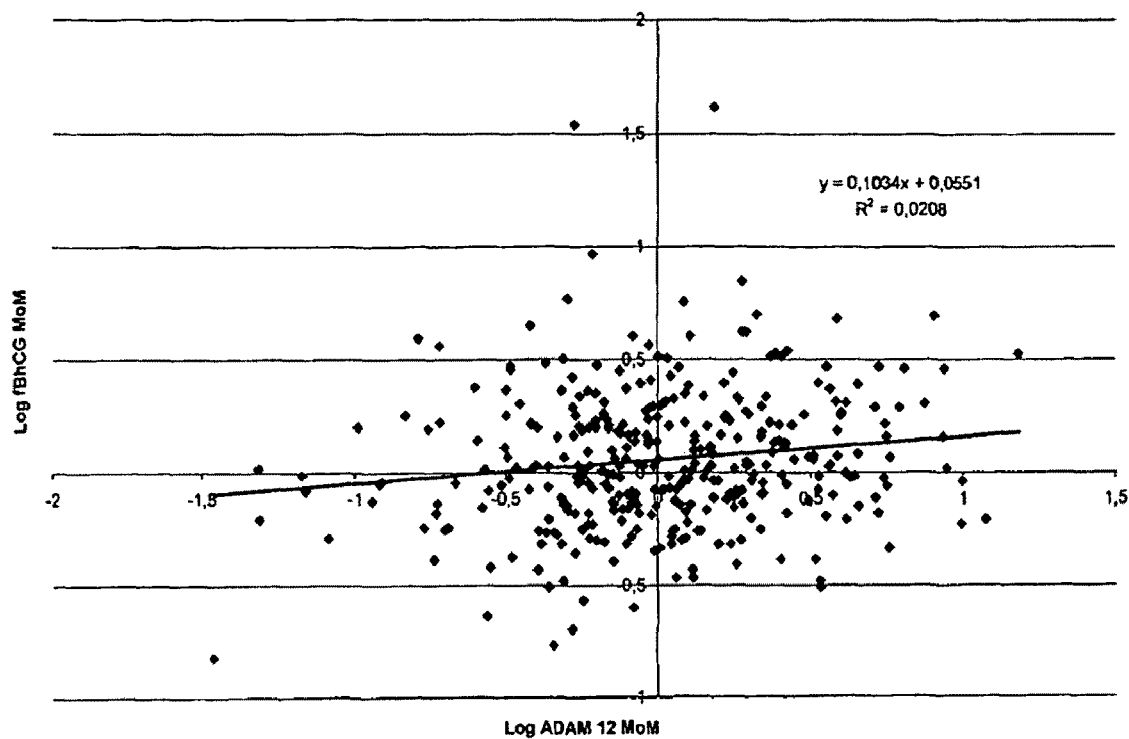
Figure 29:
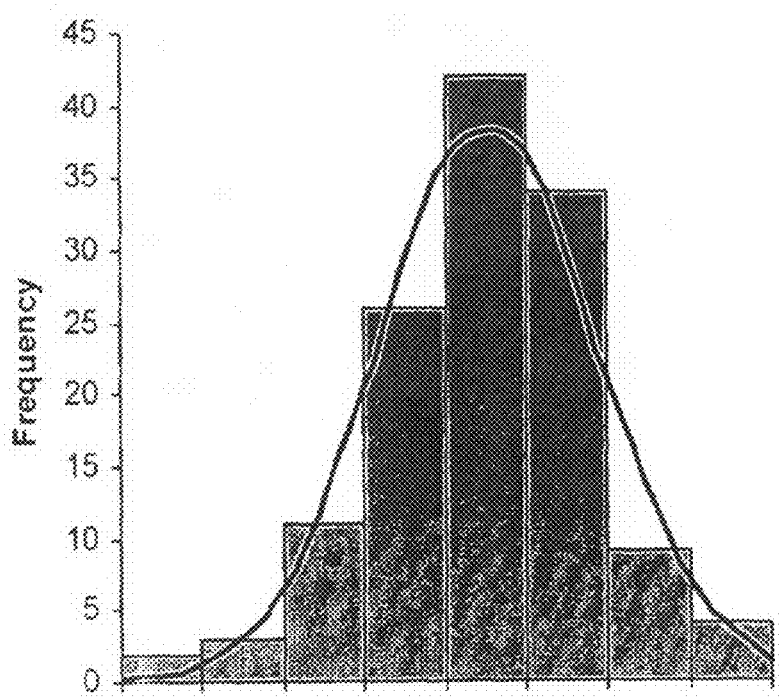
Figure 29:
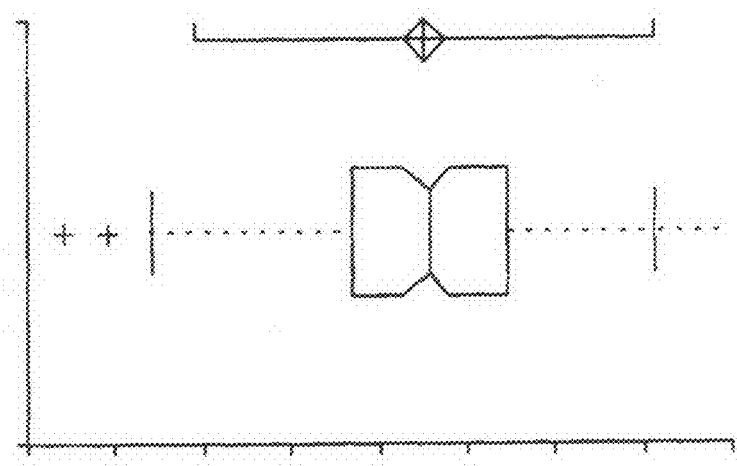
Figure 31:
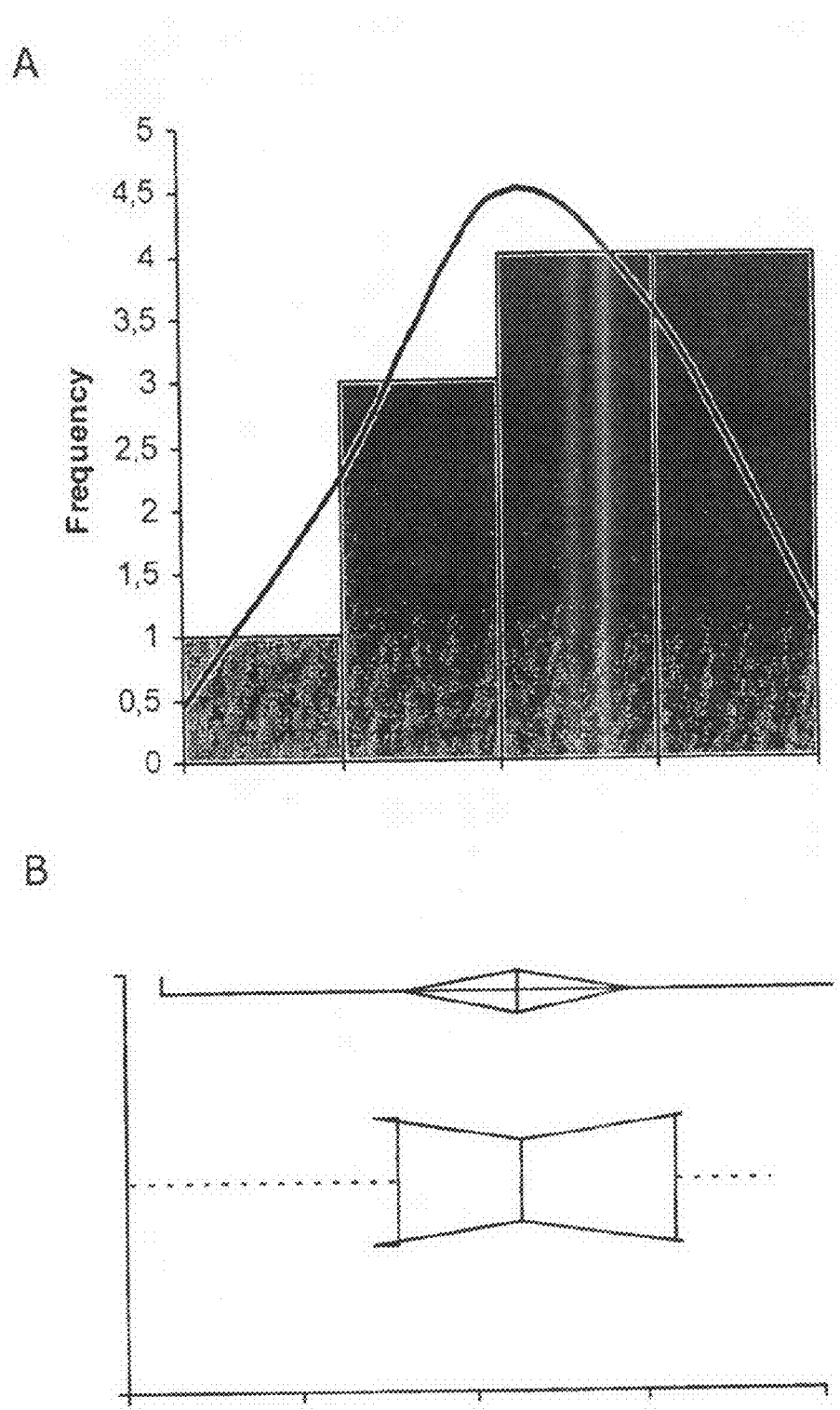
Figure 32:
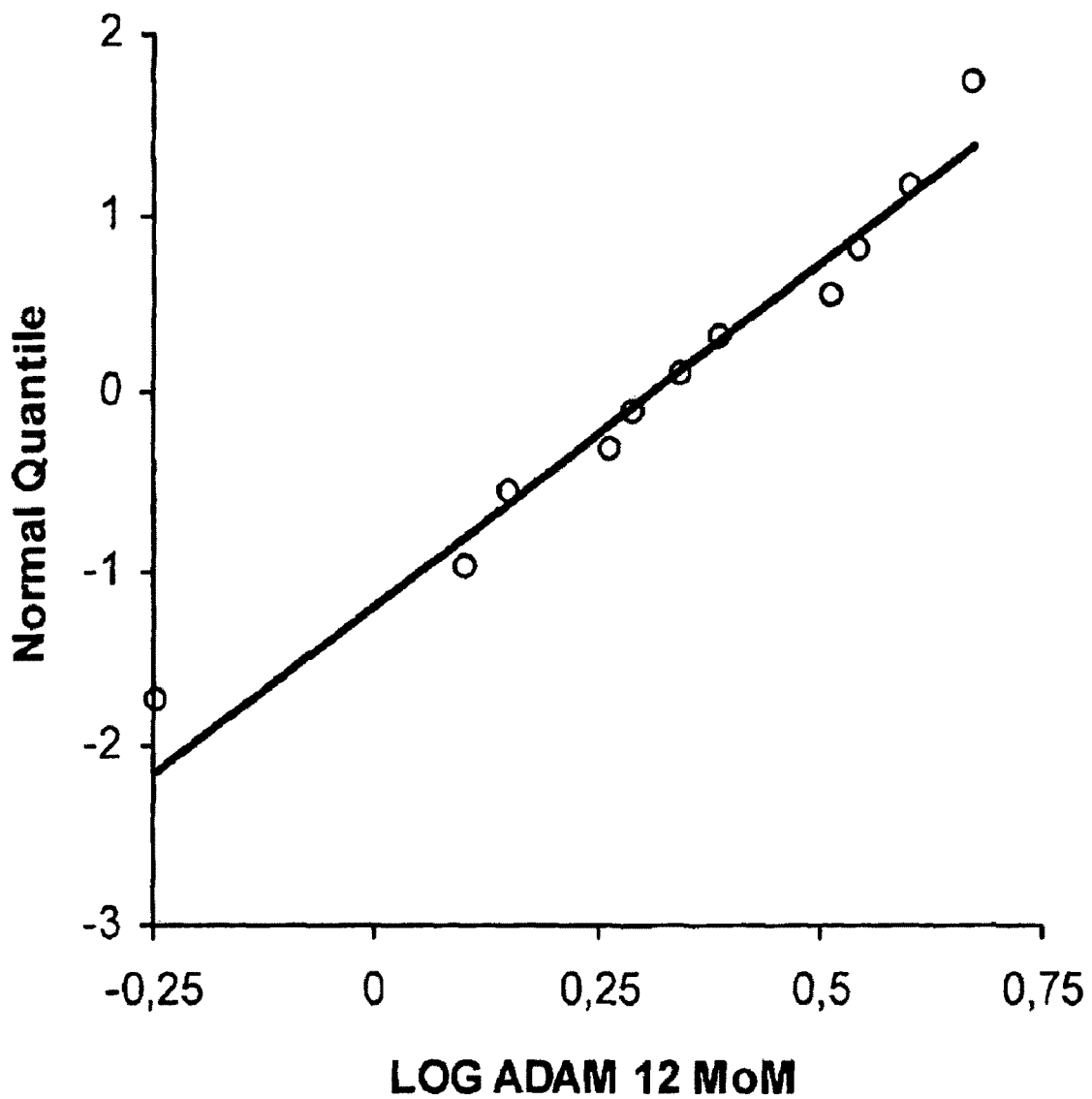
Figure 33:
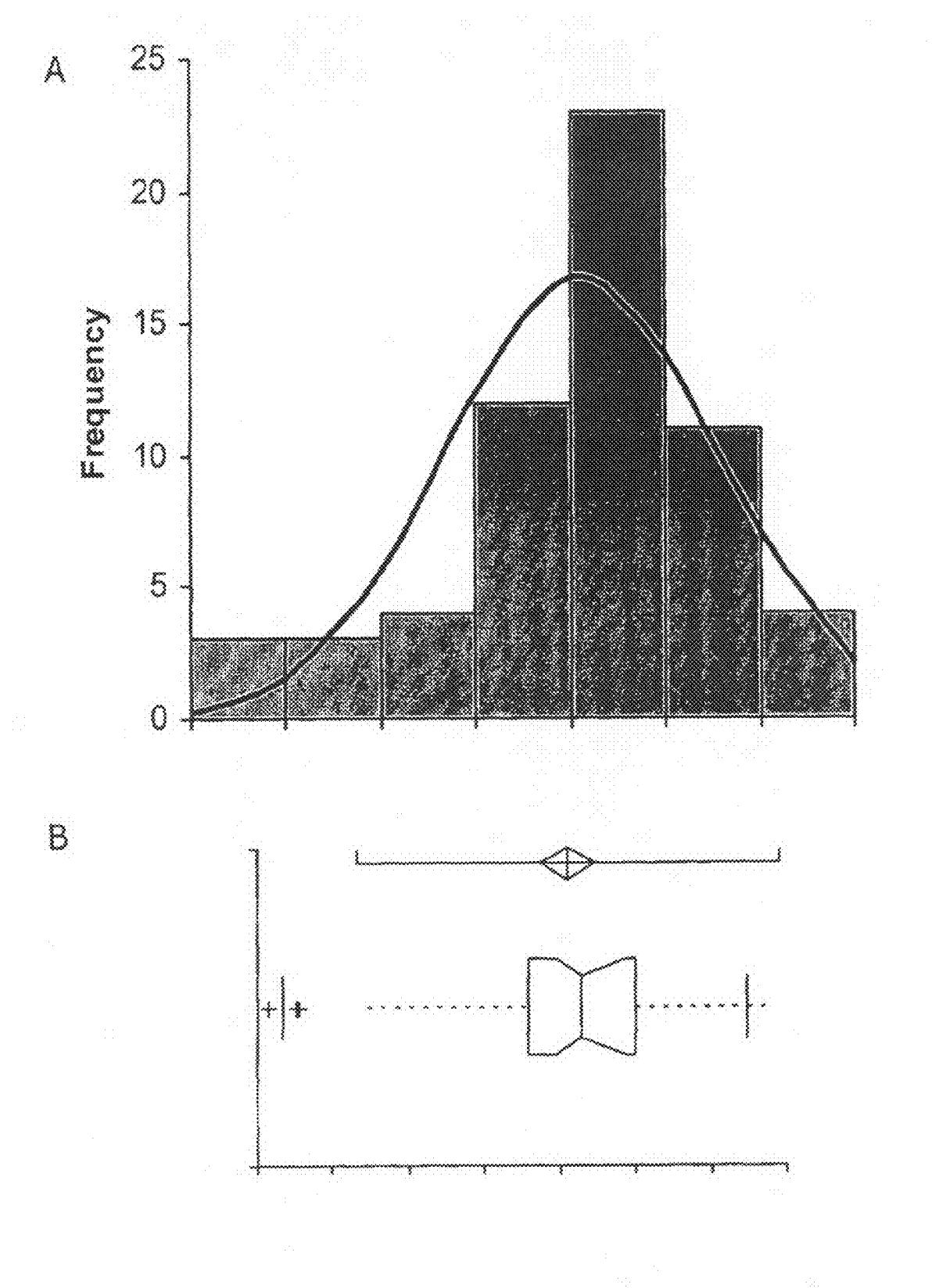
Figure 34:
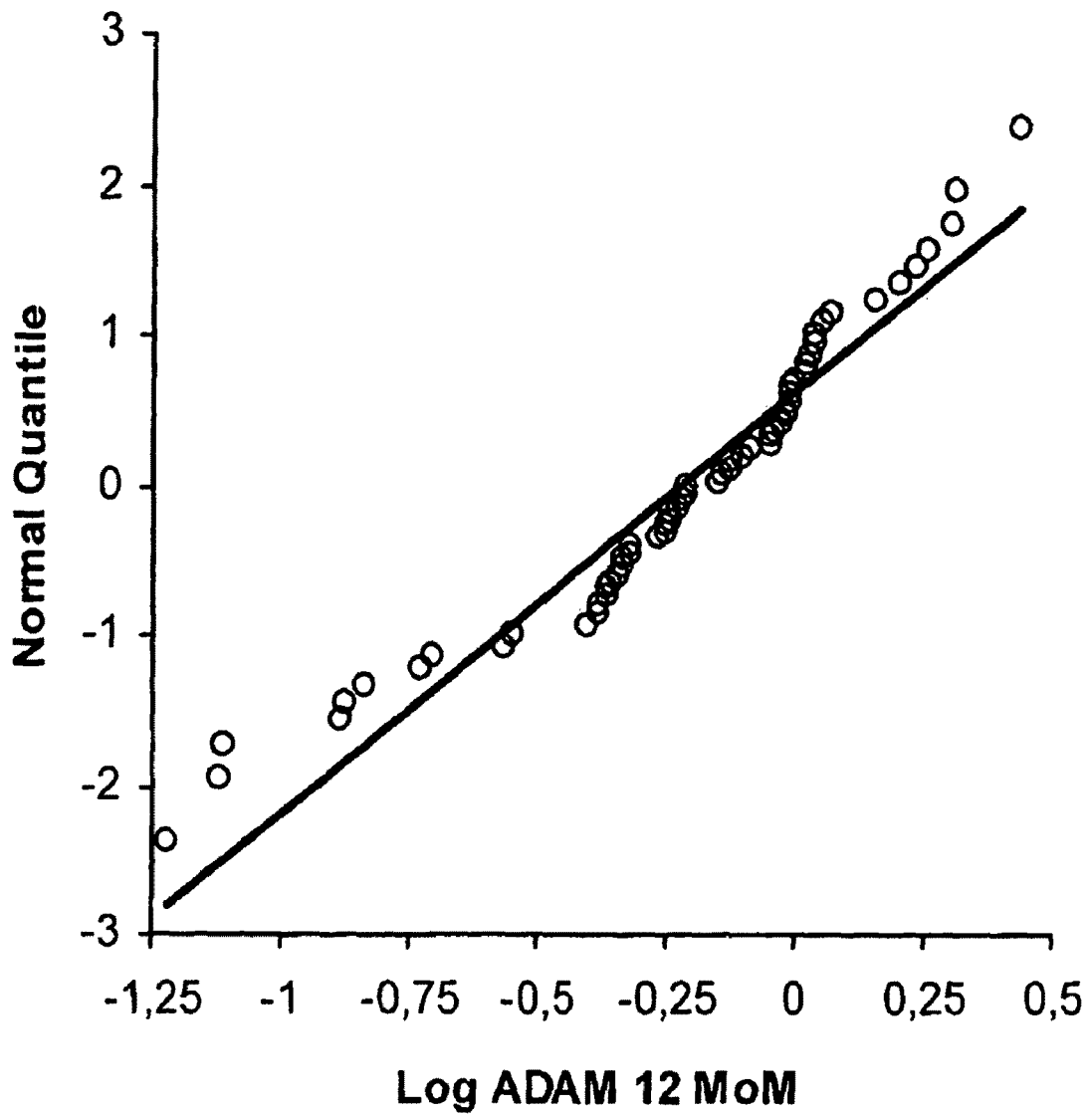
Figure 35:
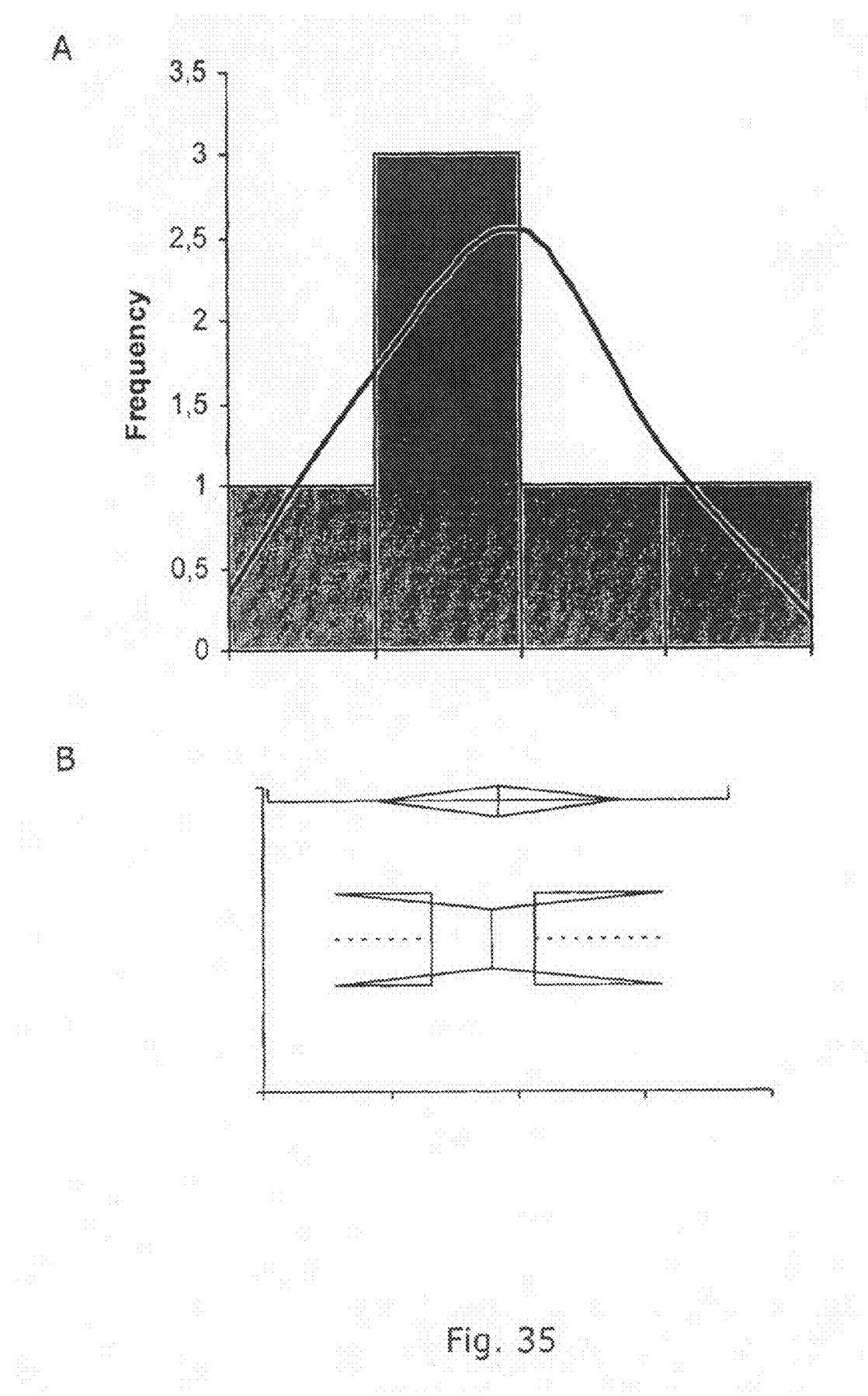
Figure 36:
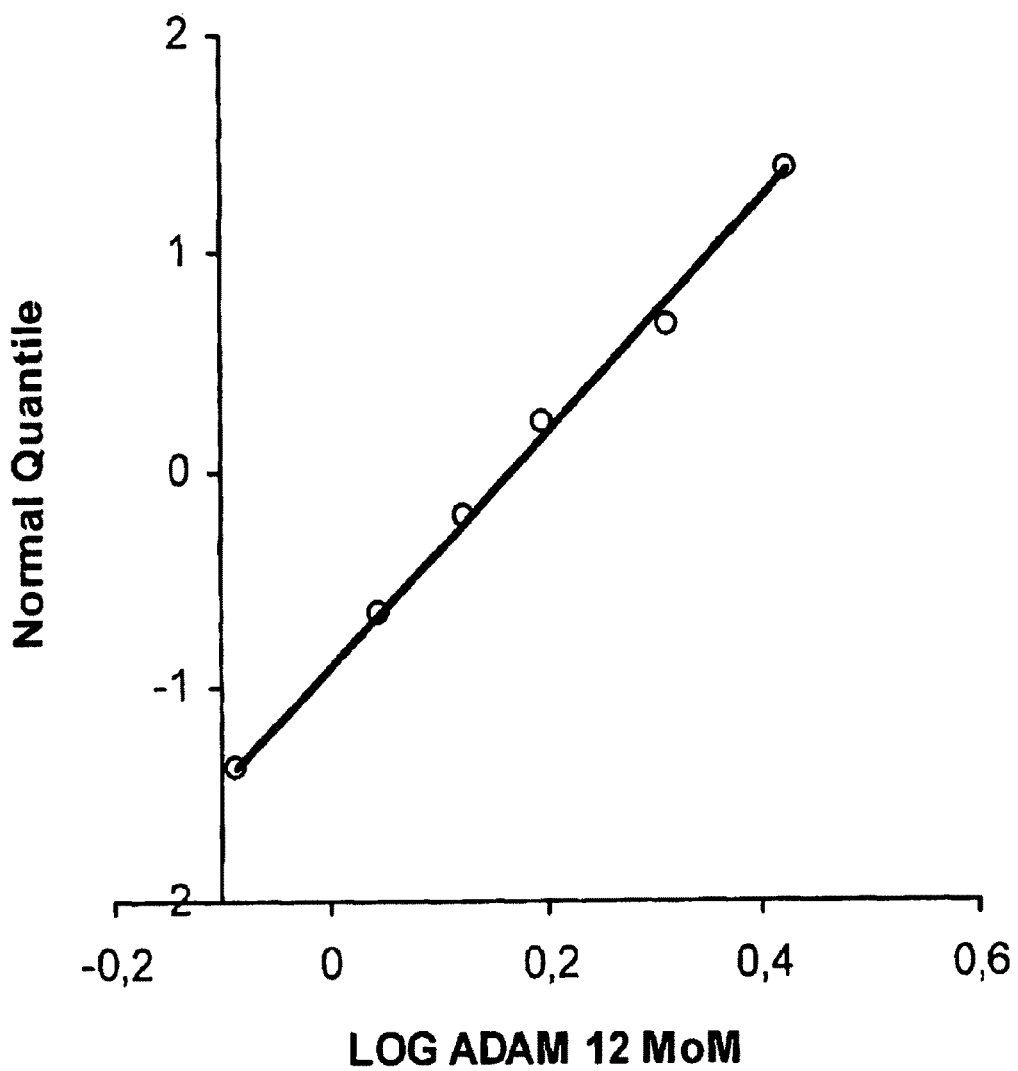
Figure 37:
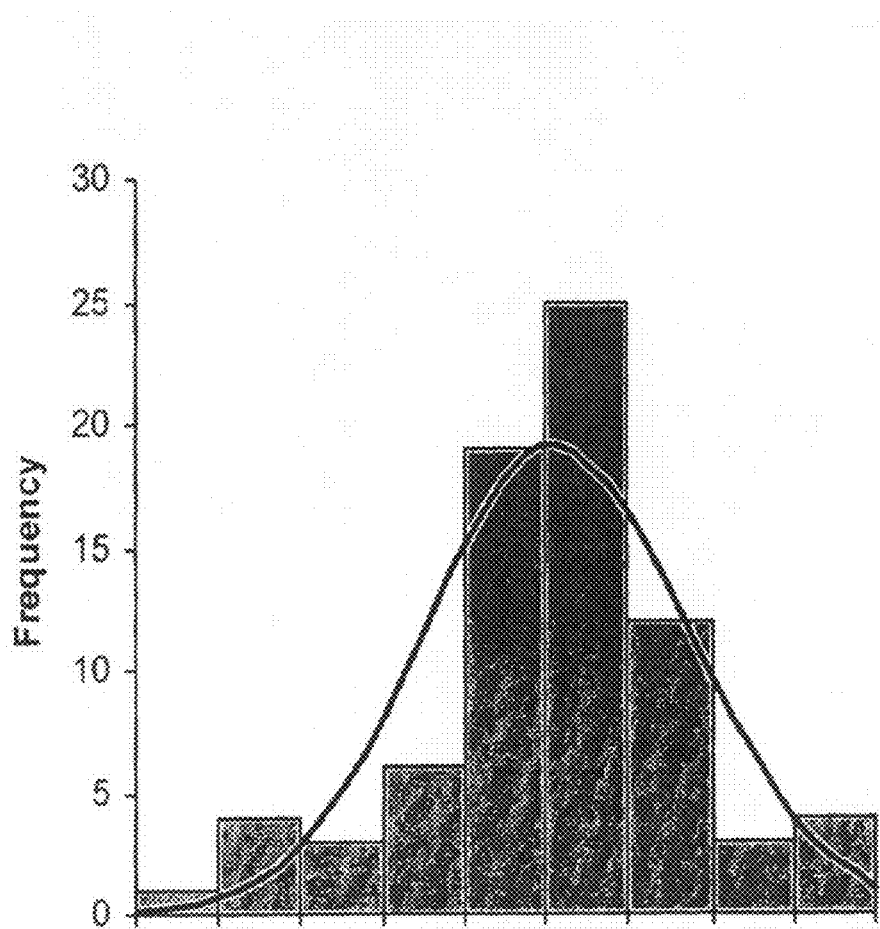
Figure 37:
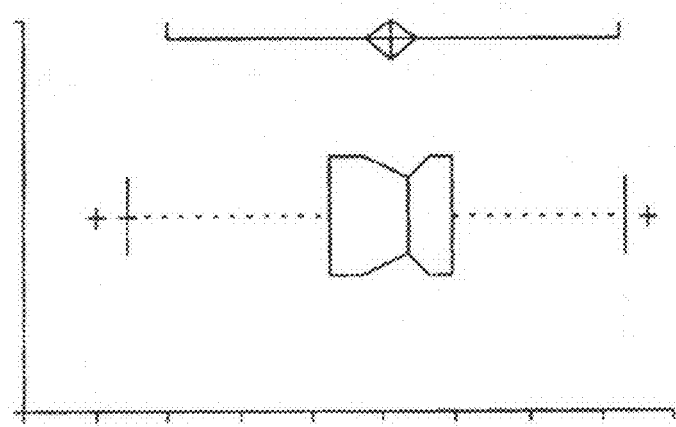

FIG. 20
Correlation between Log ADAM12 and Log free beta MoMs in first trimester controls without weight correction.
FIG. 21
Correlation between Log ADAM12 and Log PAPP-A MoMs in first trimester T21 without weight correction.
FIG. 22
Correlation between Log ADAM12 and Log PAPP-A MoMs in first trimester controls without weight correction.
FIG. 23
Correlation between Log ADAM12 and Delta NT in first trimester T21.
FIG. 24
Correlation between Log ADAM12 and Delta NT in first trimester controls.
FIG. 25
Correlation between Log ADAM12 and Log AFP MoMs in second trimester T21 without weight correction.
FIG. 26
Correlation between Log ADAM12 and Log AFP MoMs in second trimester control without weight correction.
FIG. 27
Correlation between Log ADAM12 and Log fBhcG MoMs in second trimester T21 without weight correction.
FIG. 28
Correlation between Log ADAM12 and Log fBhcG MoMs in second trimester controls without weight correction.
FIG. 29
A. Graphical depiction of the distribution of Log ADAM12 MoM values in first trimester 18 pregnancies:
B. Box-and-Whisker plot of logMoM ADAM12 values in first trimester trisomy 18 pregnancies
FIG. 30
A Normal probability plot of logMOM ADAM12 in trisomy 18 pregnancies.
FIG. 31
A. Graphical depiction of distributional data of LogMoM ADAM12 in second trimester trisomy 18 pregnancies.
B. Box-and-whisker plot of the distribution of LogMoM ADAM12 data from second trimester trisomy 18 pregnancies.
FIG. 32
Normal probability plot of logMoM ADAM12 data in second trimester trisomy 18 pregnancies.
FIG. 33
A. Graphical depiction of distributional data of LogMoM ADAM12 in first trimester trisomy 13 pregnancies.
B. Box-nad-whisker plot of the distribution of logMoM ADAM12 data from first trimester trisomy 13 pregnancies.
FIG. 34
Normal probability plot of logMOM ADAM12 in first trimester trisomy 13 pregnancies.
FIG. 35
A. Graphical depiction of the distribution of LogMoM ADAM12 data in second trimester trisomy 13 data in second trimester
B. Box-and-whisker plot of log MoM ADAM12 data in second trimester trisomy 13 pregnancies.
FIG. 36
Normal probability plot of logMoM ADAM12 in second trimester trisomy 13 pregnancies.
FIG. 37
A. Graphic depiction of distribution of LogMoM ADAm12 values in first trimester 45X0 pregnancies.
B. Box-and-whisker plot of log MoM ADAM12 values in 45X0 pregnancies.

Figure 38:
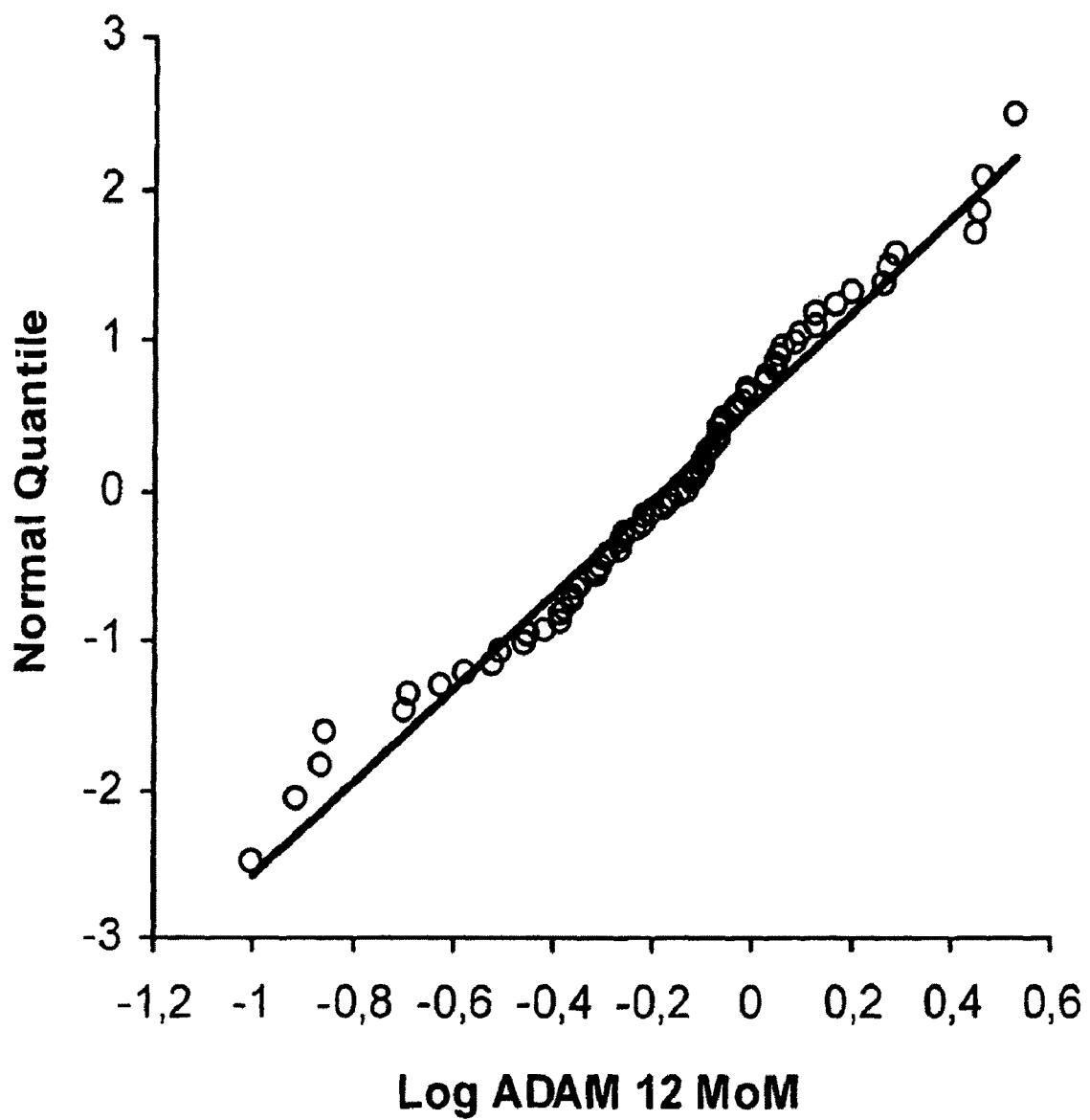
Figure 39:
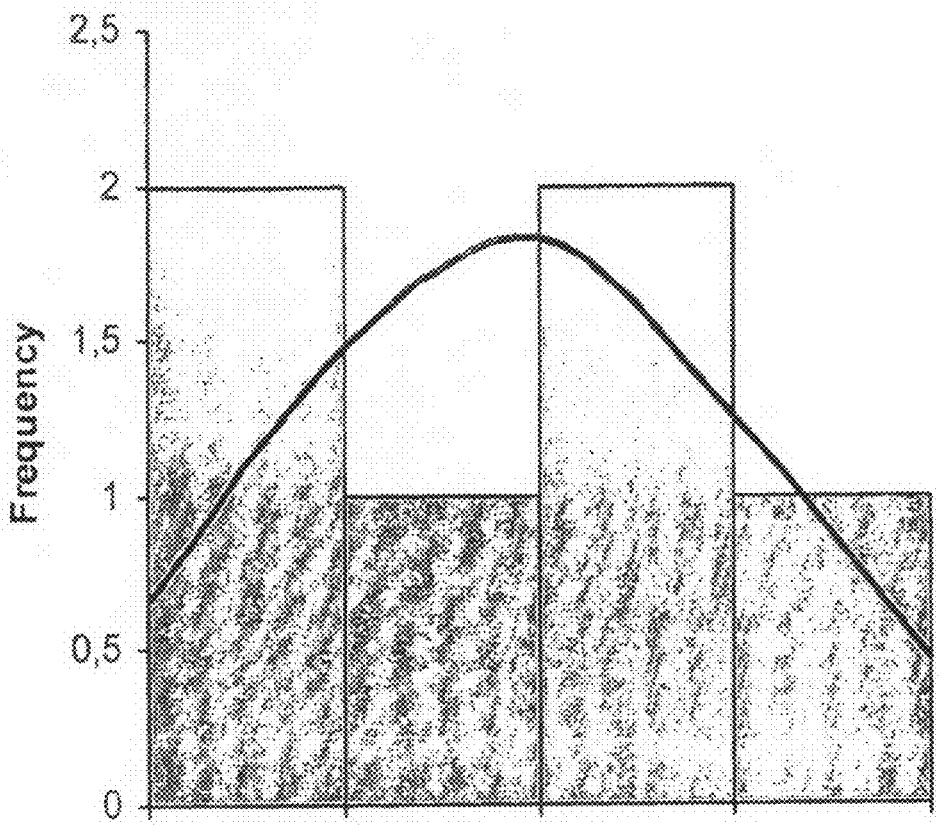
Figure 39:
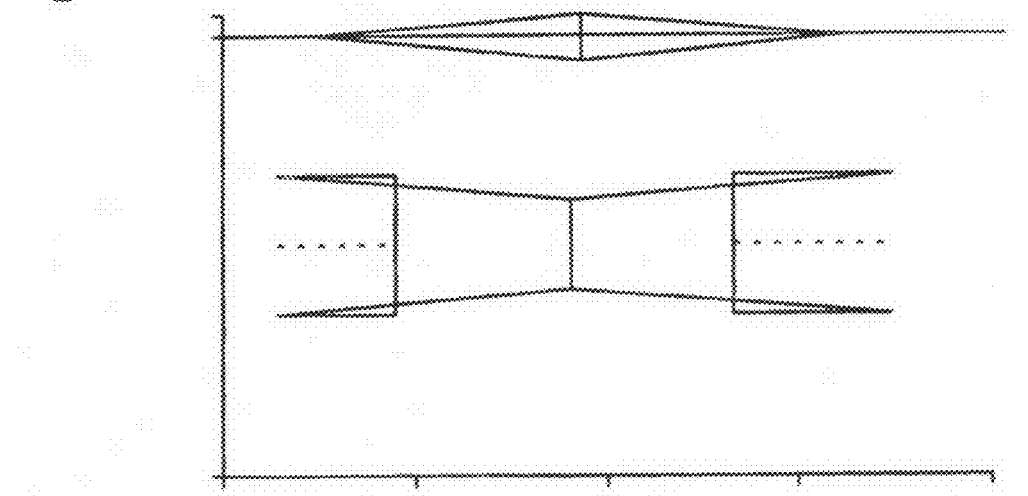
Figure 40:
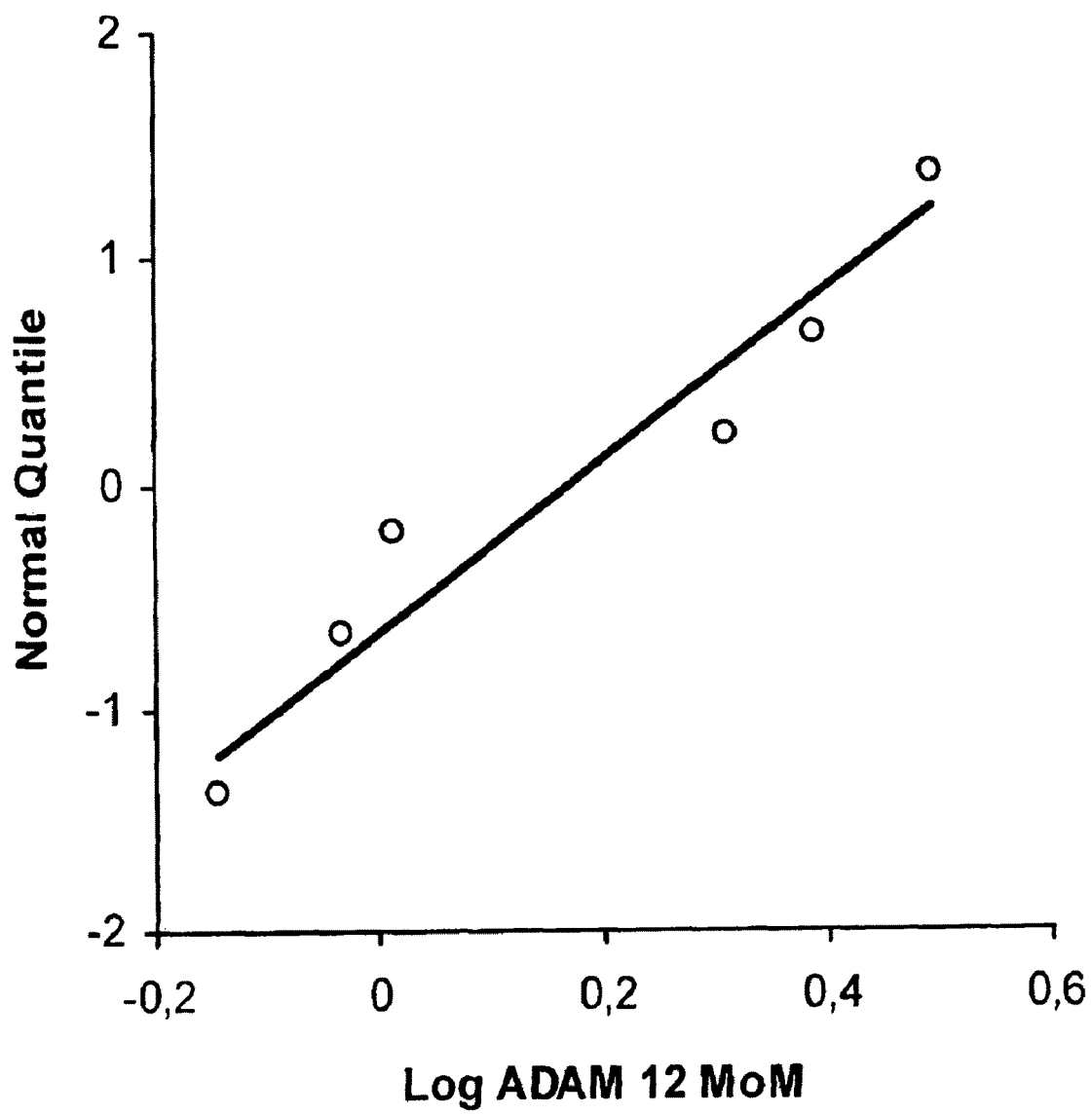
Figure 41:
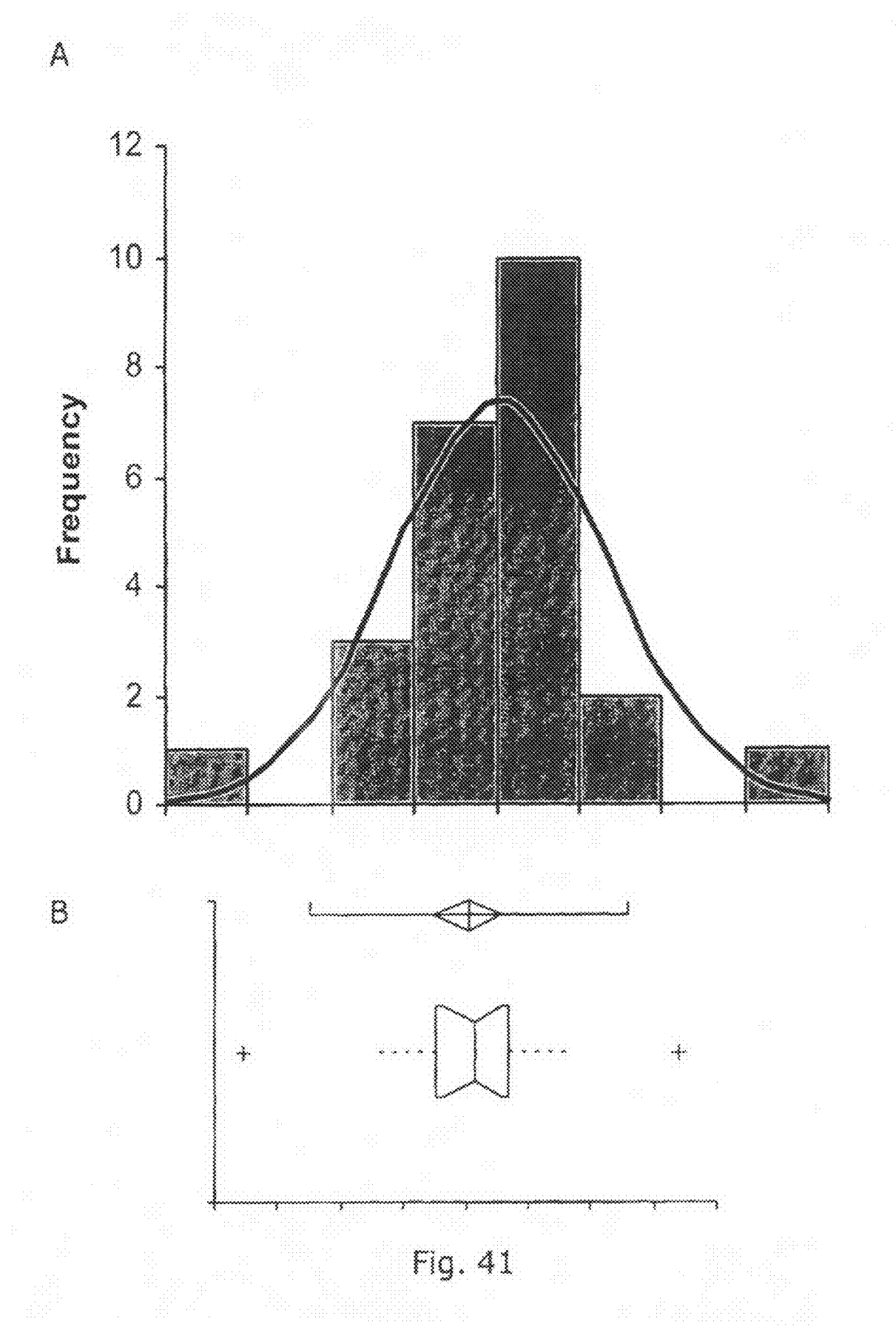
Figure 42:
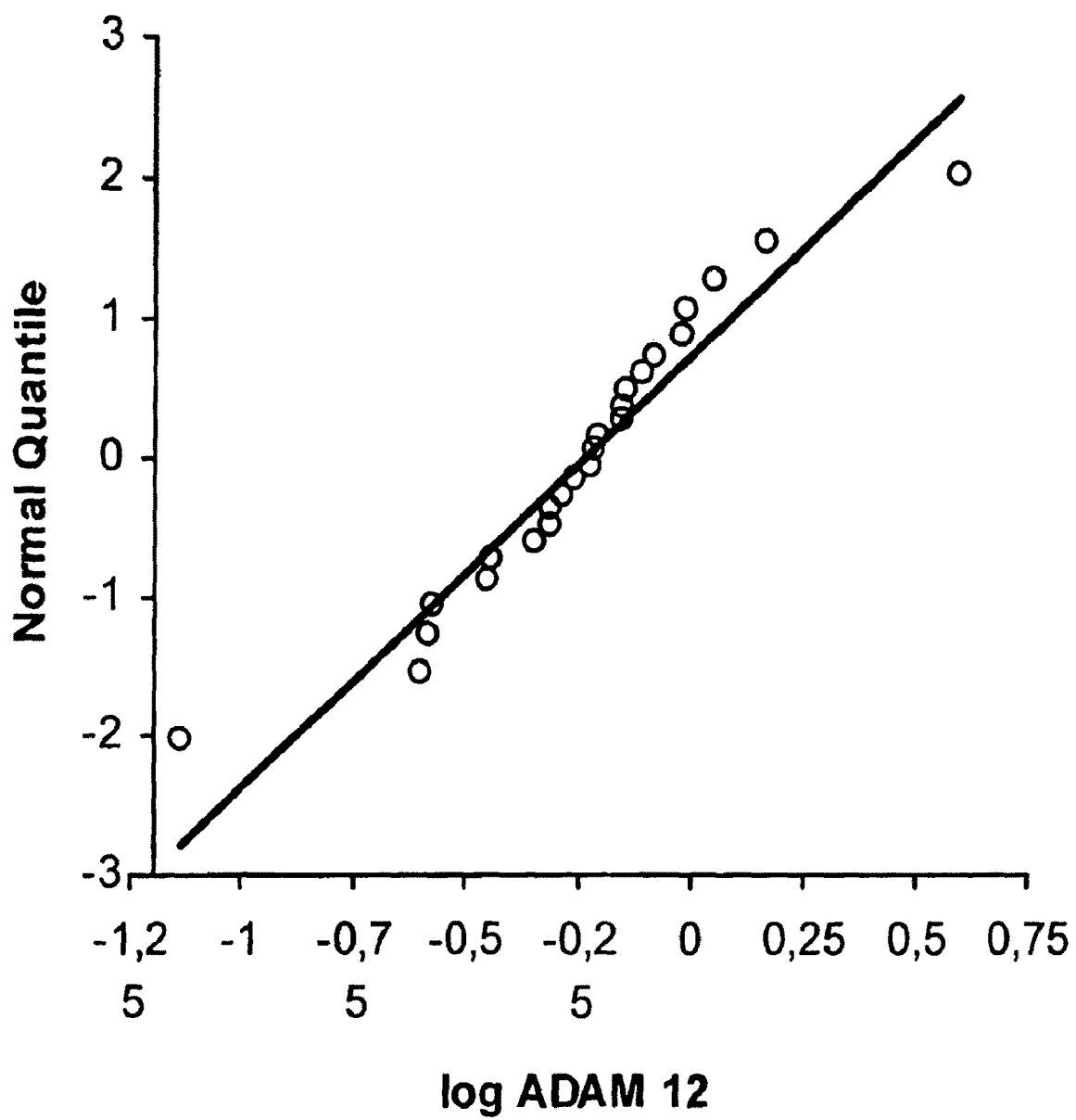
Figure 43:
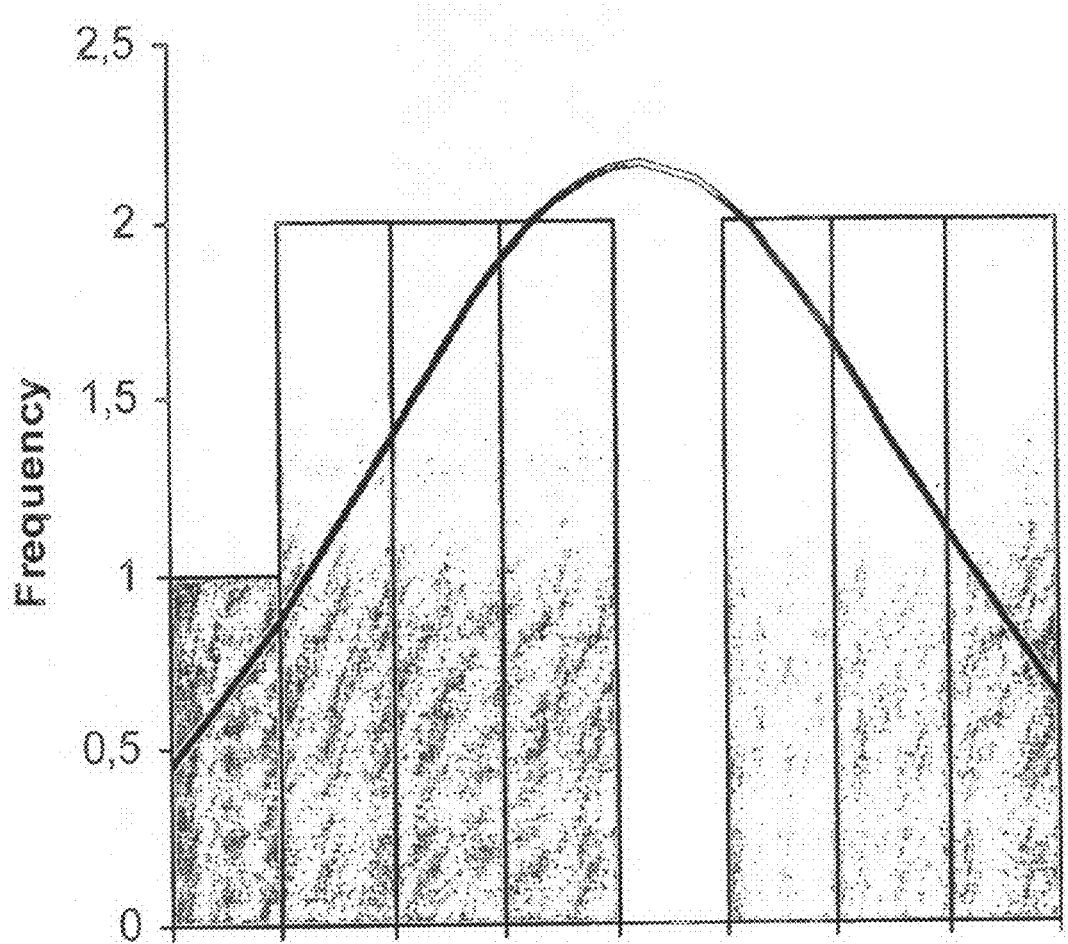
Figure 43:
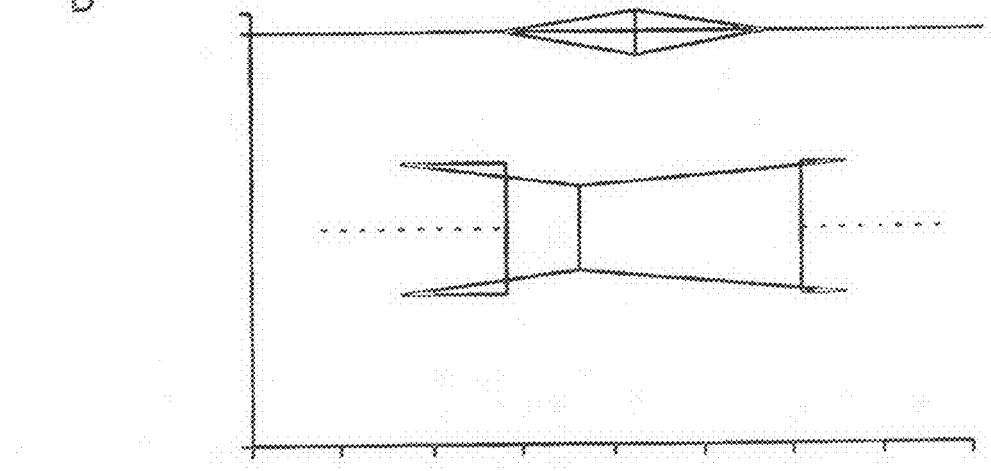
Figure 44:
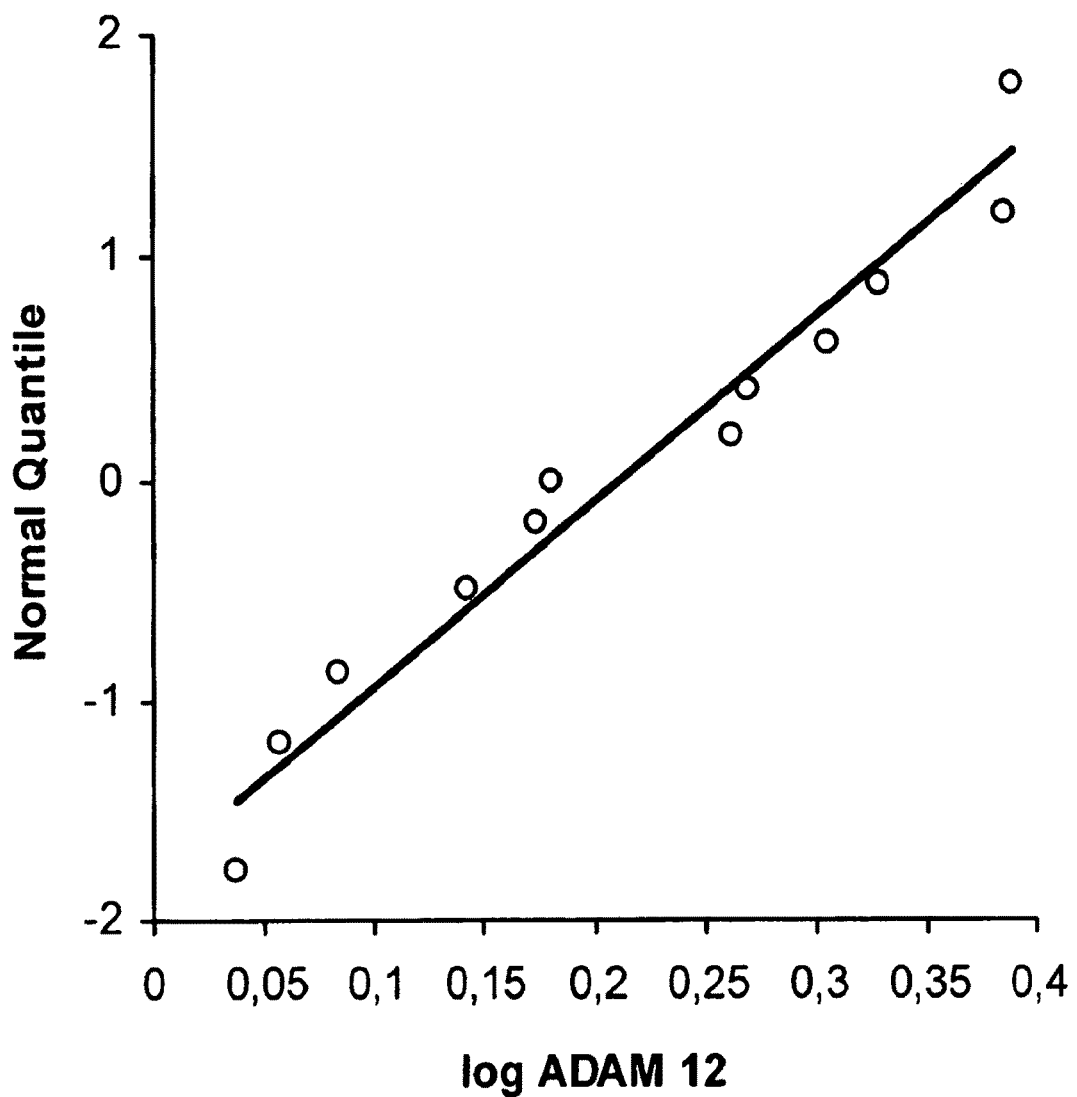

FIG. 38
Normal plot of logMoM ADAM12 values in first trimester 45X0 pregnancies.
FIG. 39
A. Distribution of logMoM ADAM12 in second trimester 45 X0 pregnancies.
B. Box-and-whisker plot of the distributional data from A.
FIG. 40
Normal probability plot of log MoM ADAM12 values from 45X0 pregnancies in second trimester.
FIG. 41
The distribution of logMoM ADAM12 values is a shown below:
A. The distribution of logMoM ADAM12 values in first trimester NTSCA pregnancies.
B. Box-and-whisker plot of the data depicted in A.
FIG. 42
Normal probability plot of logMoM ADAM12 in first trimester NTSCA.
FIG. 43
A Distribution of LogMoM ADAM12 values in second trimester NTSCA pregnancies.
B. Box-and-whisker plot of the logMoM ADAM12 data from second trimester NTSCA pregnancies depicted in A.
FIG. 44
Normal probability plot of logMoM ADAM12 data from second trimester.

EXAMPLES

Example 1

ADAM12 as a first trimester maternal serum marker for Down' syndrome in first trimester: Development of an ELISA for ADAM12 and clinical assessment on patients from Denmark.
Materials and Methods:
Serum Samples
Normal samples. Serum samples from first trimester pregnant women (n=154) were obtained as part of a routine prenatal screening program for DS at Skejby University Hospital, Aarhus, Denmark. The program is specifically for women who are 8 to 13 weeks pregnant, and includes ultrasound examination.
Second-trimester serum samples (n=91) were obtained through another routine prenatal screening program for severe malformations and DS at Statens Serum Institut. This screening program is restricted to women who are 14 to 20 weeks pregnant. All 1. and 2. trimester samples were taken in dry containers and were kept in cool storage (4° C.) until postage via the normal mail.
Term samples (n=10) were obtained from women participating in a pilot study for ADAM12 at Hvidovre University Hospital, Copenhagen. The women were 38 to 40 weeks pregnant and all had a normal pregnancy with no obstetrical complications prior to sampling. An apparently healthy 28 weeks pregnant employee at Statens Serum Institut donated blood for the storage temperature and blood container comparison. Term samples and samples for the storage temperature and blood container comparison were centrifuged and kept at −20° C. until time of study and/or analysis.
DS samples. 1. trimester DS samples (n=18) consisted of samples from the Skejby screening program (n=3) which were identified as result of the screening program i.e. in the first trimester and samples from the ongoing quality control program at Statens Serum Institut (n=15) that were diagnosed during 2. trimester (n=10) or at birth (n=5).

Second-trimester serum DS samples (n=12) were all from the ongoing quality control program at Statens Serum Institut and comprised of samples diagnosed in the 2. trimester (n=8) or at birth (n=4).

All DS diagnoses were established by karyotyping. Gestational age was determined by the date of the last menstrual period and, in most cases, confirmed by ultrasound examination.

Ethics

All samples were either collected for projects approved by the Scientific Ethics committees of Aarhus or Copenhagen County, or were obtained as part of ongoing quality-control procedures of Statens Serum Institut.

Reagents

Recombinant ADAM12-S used for standardization was obtained by transfecting human 293-EBNA cells with full-length cDNA encoding human ADAM12-S (GenBank AF023477), and purified using cation-exchange and concanavalin A affinity chromatography as described by Loechel et al., 2000. Protein concentration was determined using the BCA assay (Price, Rockford Ill.).

Antibodies

Several previously described antibodies against recombinant ADAM12 were tested in this study: mouse IgG monoclonal antibodies 8F8, 6E6, and 6C10; and polyclonal antibodies rb 122, and rb 134 (Gilpin et al., 1998, Iba et al., 1999, Kawaguchi et al., 2002, Kronqvist et al., 2002). Based on pilot studies comparing the effectiveness of all the antibodies in the ELISA, the antibodies 6E6 and 8F8 were used for coating and detection steps respectively.

Biotinylation

To generate biotinylated antibodies, 8F8 IgG was transferred to a labeling buffer consisting of 0.1M $NaHCO_3$ (pH 8.2) (Merck, Darmstadt, Germany), using NAP™5 columns (Amersham Biosciences, Sweden). The concentration was calculated from the absorbance at 280 nm using labeling buffer as a reference. A mixture of 100 mg of Biotin (Sigma 1759) dissolved in 2.5 ml Dimethylformamide (LabScan, Valby-Denmark) was added to the antibody (10 µl per mg). After mixing for 2 h at room temperature, biotinylated antibodies were purified by gel filtration using PD-10 columns (Amersham Biosciences, Sweden). The concentrations of biotinylated monoclonal antibody were calculated from the absorbance readings at 280 nm.

Standards and Controls

Controls were prepared from a second-trimester serum pool diluted (83 µg/l, 164 µg/l, and 335 µg/l) in dilution buffer consisting of 1% (v/v) bovine serum albumin (BSA)(Sigma A 4503) and 0.05% (v/v) Tween 20 (Merck) in a 0.15 M phosphate-buffered saline (PBS) solution. The present inventors calibrated a third-trimester serum pool against recombinant ADAM12, and used the pool to generate a standard curve for determining ADAM12 concentrations. Standards ranging from 42 to 667 µg/l were prepared by diluting the serum in dilution buffer.

All standards, controls, and samples were analyzed in duplicate.

ELISA Procedures, Optimisation, and Testing

Microtiter plates (Nunc-Immuno™ Plate, MaxiSorp™ Surface, Nalge Nunc International-Denmark) were coated with 0.41 µg/well monoclonal antibody 6E6 in 0.1 M carbonate buffer (pH 9.6). Plates were washed twice after overnight incubation at 4° C. All washing steps were done with washing buffer consisting of 0.1 M PBS with 0.05% (v/v) Tween 20 (Merck 822184). A buffer consisting of 1% (v/v) BSA (Sigma A 4503) in wash buffer was then added to the plates (150 µl/well) to block non-specific binding. The plates were incubated in blocking buffer for 30 minutes at room temperature then washed 3 times. Standards, controls, and samples diluted in blocking buffer were added (100 µl/well), incubated for two hours at room temperature, then washed 4 times. Biotinylated monoclonal antibody 8F8 (0.5 µg/ml) was added and plates were incubated for 1 hour at room temperature then washed 4 times. Peroxidase-conjugated streptavidin (DAKO P397, Denmark) was added (100 µl/well), incubated for 1 hour at room temperature, then washed 3 times. A color reaction was obtained by adding 100 µl/well of a solution consisting of ortho-phenylene-diamine (OPD) tablets (Kem-En-Tec, Copenhagen, Denmark) and hydrogen peroxide dissolved in citric acid buffer (pH 5.0), and incubating for 30 minutes at room temperature. One hundred and fifty µl (10% v/v) of sulphuric acid was added to stop the color reaction, and the reaction intensity was measured by spectrometry (490-620 nm) (Victor, PLS—Wallac, Turku, Finland). To assess the intra- and inter-assay variability the present inventors analyzed the same samples 6 times in the same run and repeated the same run for 6 days in a row.

Stability of ADAM12

To investigate the stability of ADAM12 the present inventors conducted repeated freeze-thaw tests. This study was conducted using the third-trimester serum pool, and individual aliquots were analyzed twice. Recombinant ADAM12 was stored at −20° C.

The present inventors also investigated the temperature stability of ADAM12 in serum. Samples were taken from one venipuncture of an apparently healthy employee at Statens Serum Institut in her third trimester of pregnancy. Serum was separated into aliquots immediately after centrifugation: 15 aliquots were kept at room temperature, 10 at 4° C., and 10 at 37° C. All samples were analyzed in the same run.

To determine the significance of the type of blood container used, the present inventors analyzed serum/plasma from a single subject taken in EDTA, citrate, heparin and dry blood containers. All samples were obtained in one venipuncture and handled under identical conditions.

Clinical Assessment

Down's syndrome: To investigate the value of ADAM12 concentration as a screening marker for DS, the present inventors compared the ADAM12 values from the pregnancies with confirmed DS with the median value for maternal serum ADAM12 concentration from non-DS pregnancies at the same gestational age. As only 3 of the first trimester DS samples were recent and collected together with controls, whereas 15 DS cases were stored at −20° C. for up to several years, the present inventors examined the MoM values separately.

PAPP-A and Beta Human Chorionic Gonadotropin (βhCG) Versus ADAM12

To establish the relation between ADAM12, PAPP-A and βhCG in first-trimester serum samples, the present inventors used the 154 unaffected and the 3 DS samples from the Skejby screening program for which PAPP-A and βhCG analyses had previously been performed as a part of a routine first trimester screening program. In addition the present inventors used the 15 DS samples from Statens Serum Institut where the same analysis for βhCG and PAPP-A had been performed.

ADAM12 throughout pregnancy: To assess the changes in serum levels of ADAM12 throughout pregnancy, the present inventors used the analysis of the 154 first trimester serum samples, the 91 second-trimester serum samples and the 10 term serum samples, i.e. all the unaffected serum samples.

Statistics

Median serum ADAM12 concentrations were estimated by linear regression of the logarithm10 ADAM12 concentration on gestational age (days). Gestational age was determined according to the last menstrual period and confirmed by ultrasound (CRL or BPD) in most cases. All concentrations were transformed into multiples of the calculated medians (MoMs) of the unaffected pregnant women. Compatibility with the normal distribution was ascertained using normal plots. Correlations were performed by using Pearson's correlation coefficient. The screening efficiency of ADAM12 alone, or in combination with other markers, was assessed by receiver-operator-characteristics (ROC)-analysis made by Monte Carlo simulation using published procedures (Larsen et al., 1998). A standardized age distribution of pregnant women was used (Van der Veen et al., 1997). The a priori, age-related risk of giving birth to a DS child was taken from Cuckle et al. (1987). The distribution parameters for the markers PAPP-A, βhCG and nuchal translucency (NT) were taken from a published meta-analysis (Cuckle & van Lith 1999).

Results

ADAM12 ELISA and Stability

FIG. 1A shows that coating with the monoclonal antibodies 6E6 and 8F8 resulted in the greatest absorbance. Background levels were high when 8F8 was used as the coating antibody; thus, the present inventors used 6E6 as catching antibody adsorbed on the polystyrene wells, and 8F8 as the biotinylated detector antibody. The ADAM12 ELISA has an assay range of 42-667 µg/l (FIG. 1B). The intra- and inter-assay coefficients of variation were 5% and 13%, respectively. Dilution curves of recombinant ADAM12 standards and pregnancy serum were linear and parallel.

Recombinant ADAM12 stored at −20° C. began to degrade after approximately 4 months. No degradation could be detected in ADAM12 in serum after 6 months of storage at −20° C. The present inventors found that ADAM12 is stable through at least 8 cycles of freezing and thawing (FIG. 1C). Serum samples are stable for 42 hours at room temperature, and storage at 4° C. prolongs the stability to 4 days (FIG. 1D). The analysis of plasma samples taken in different blood containers showed that ADAM12 was barely detectable in plasma taken in EDTA containers. Heparin and citrate containers were equivalent to dry containers with regard to detectable serum ADAM12 levels.

ADAM12 in Pregnancy

Figure 2:
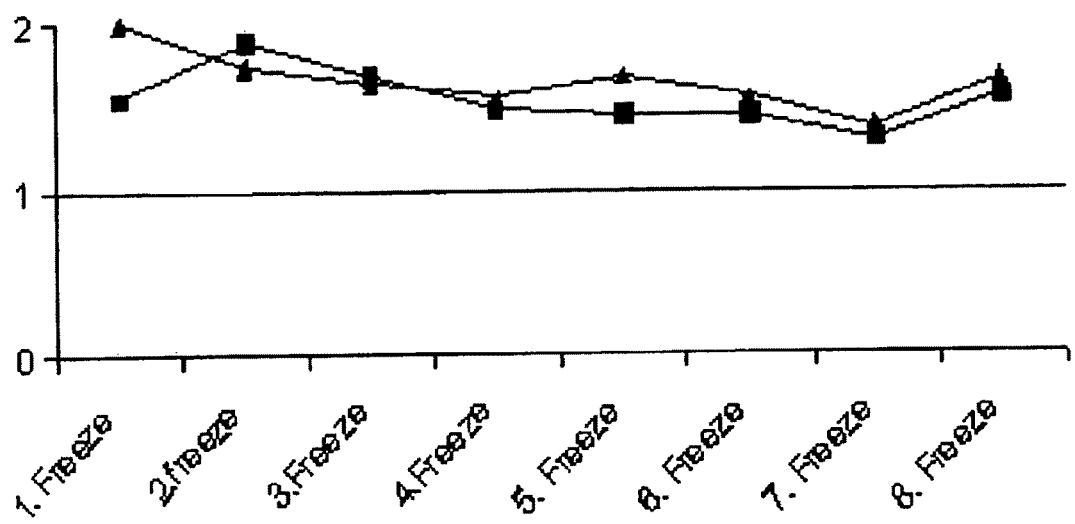
Figure 3:
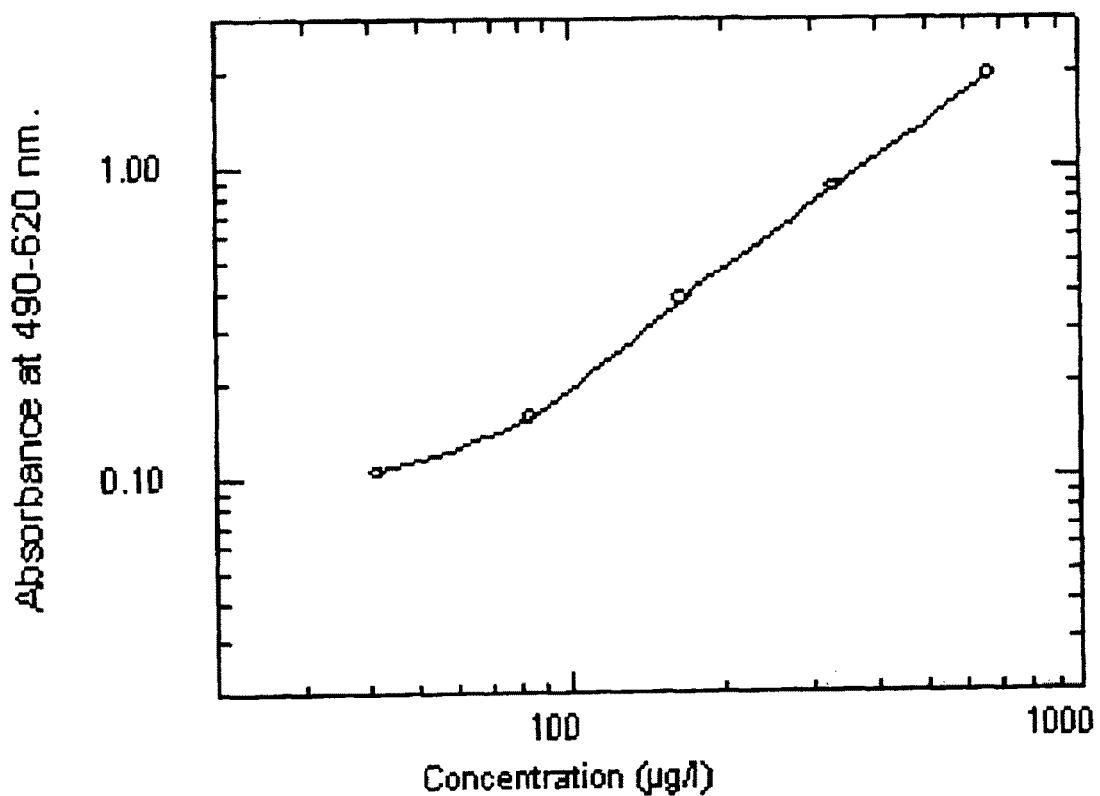
Figure 4:
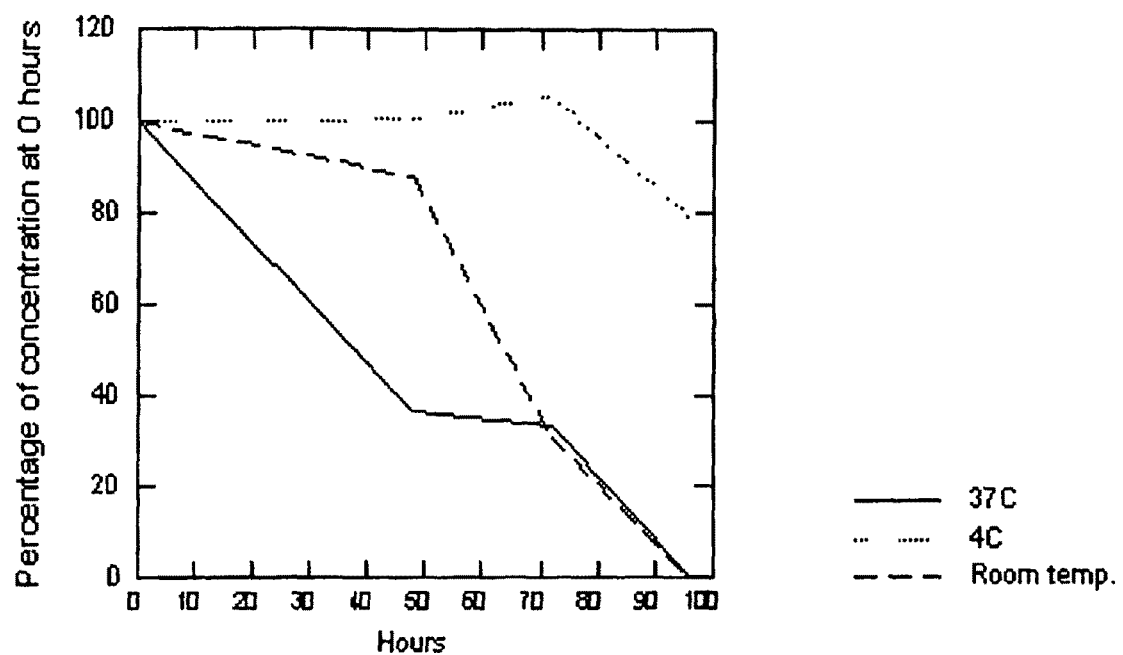
Figure 5:
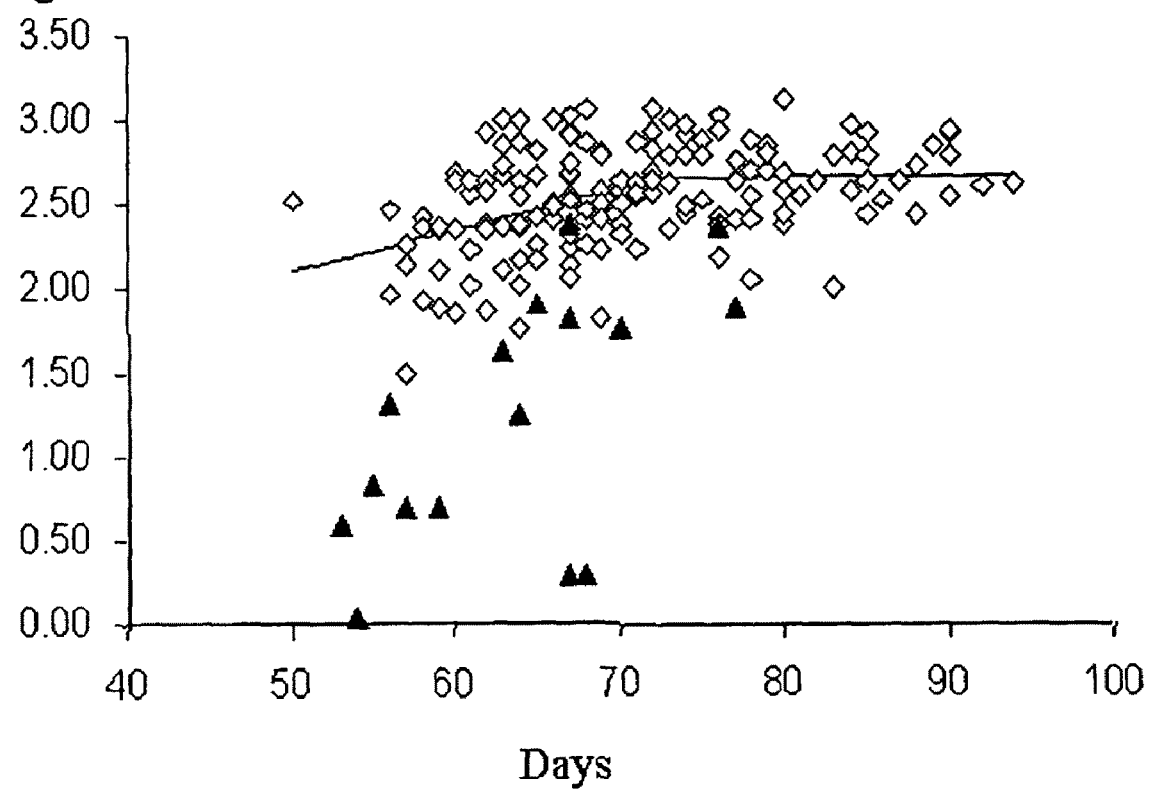
Figure 6:
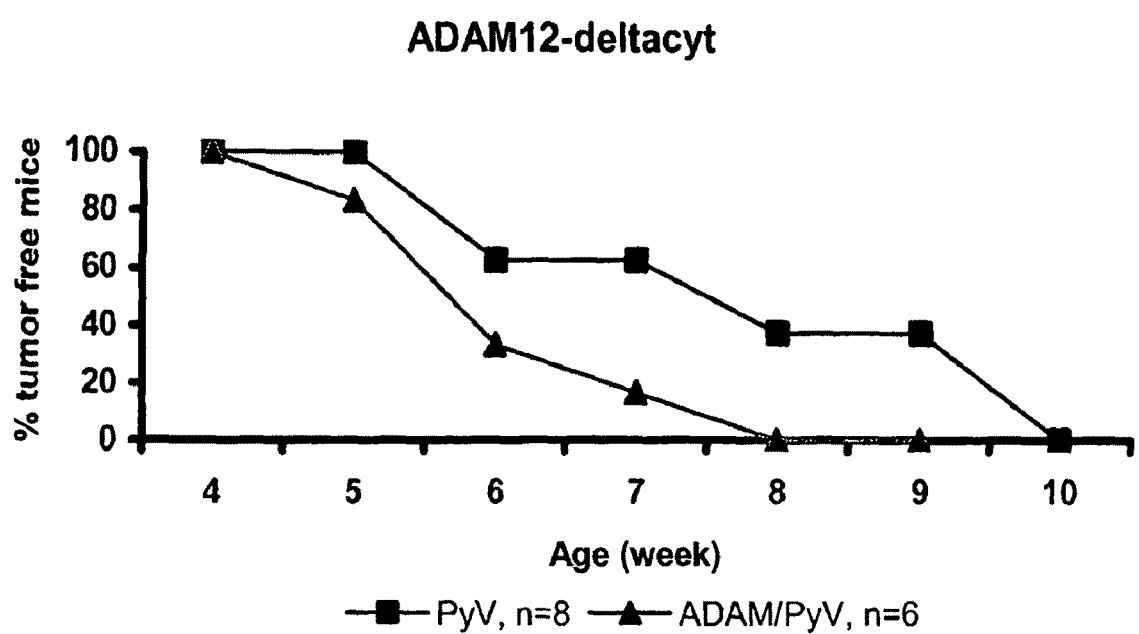
Figure 7:
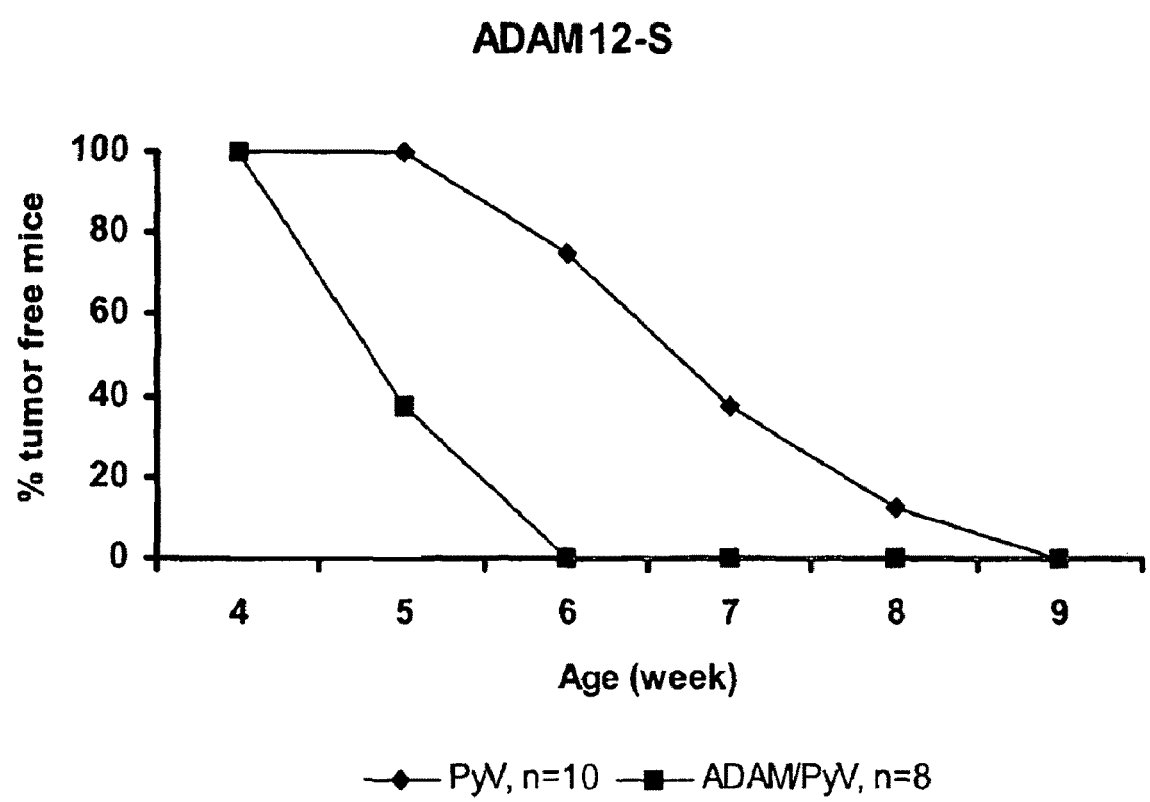
Figure 8:
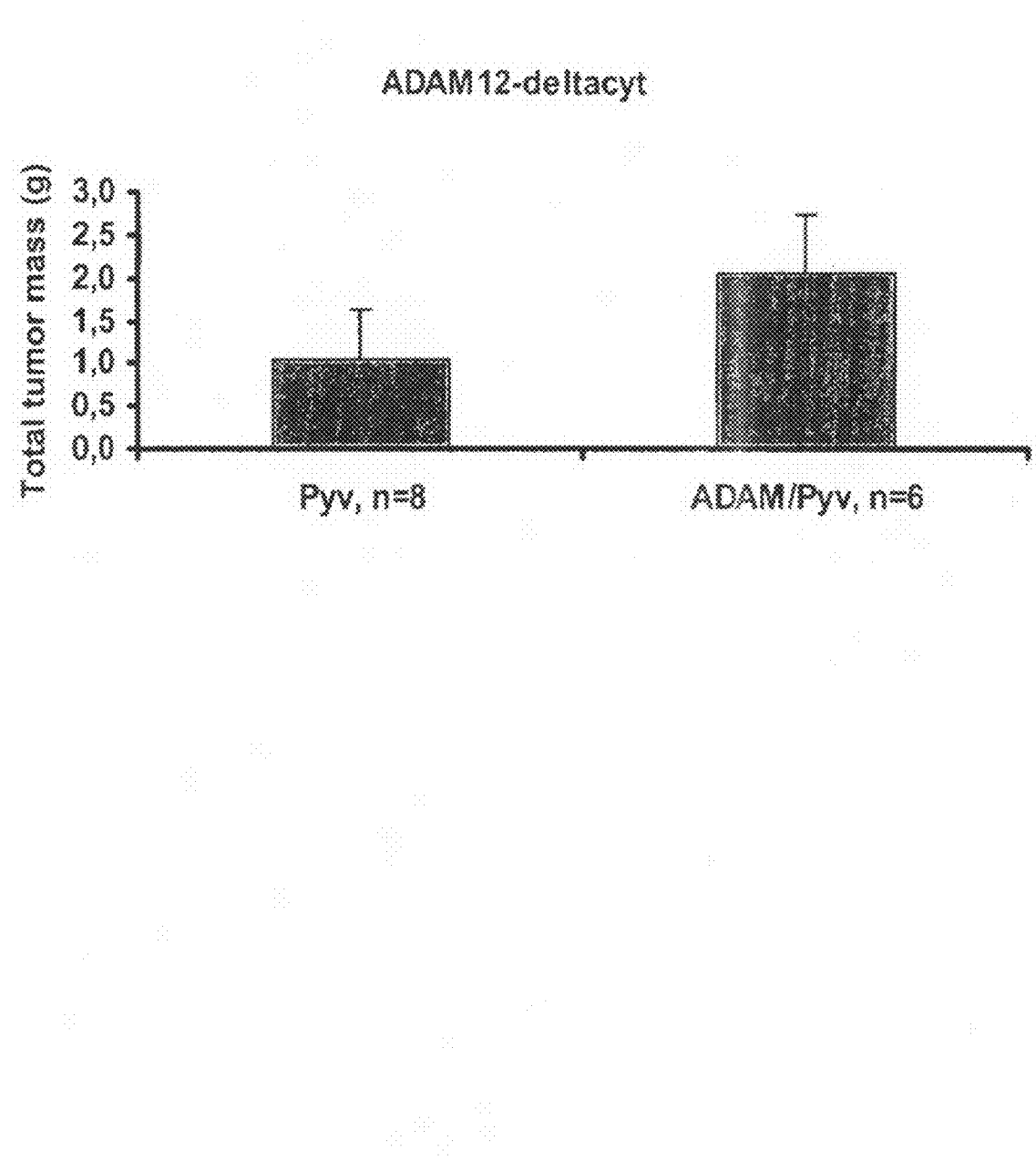
Figure 9:
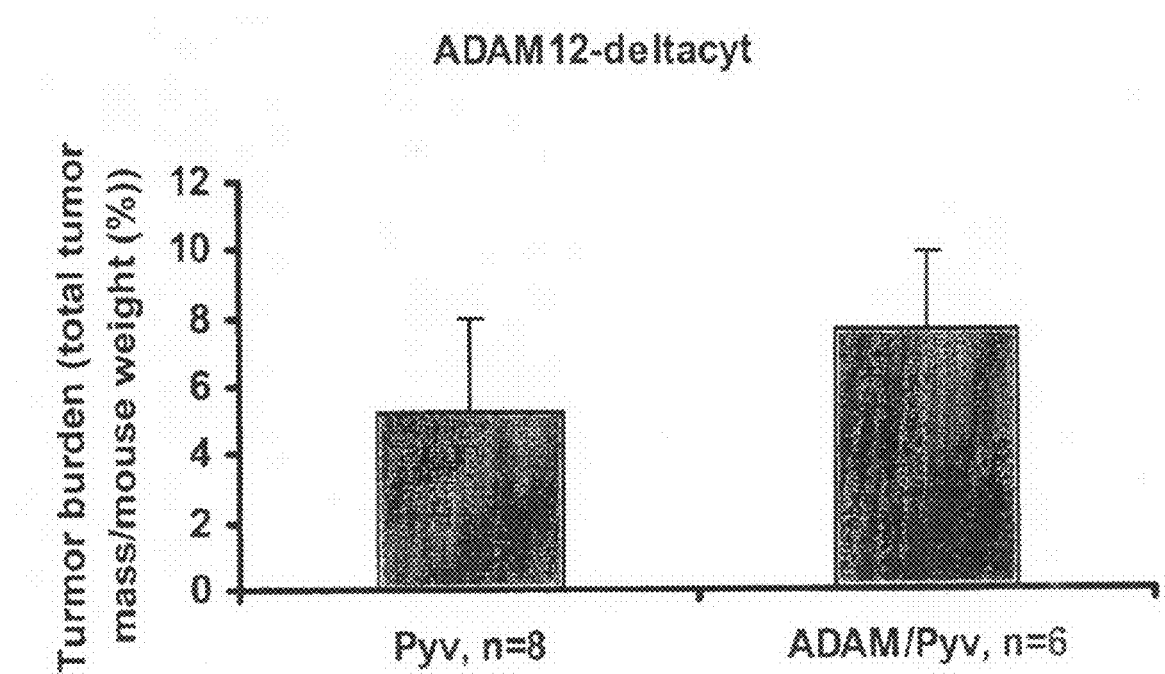
Figure 10:
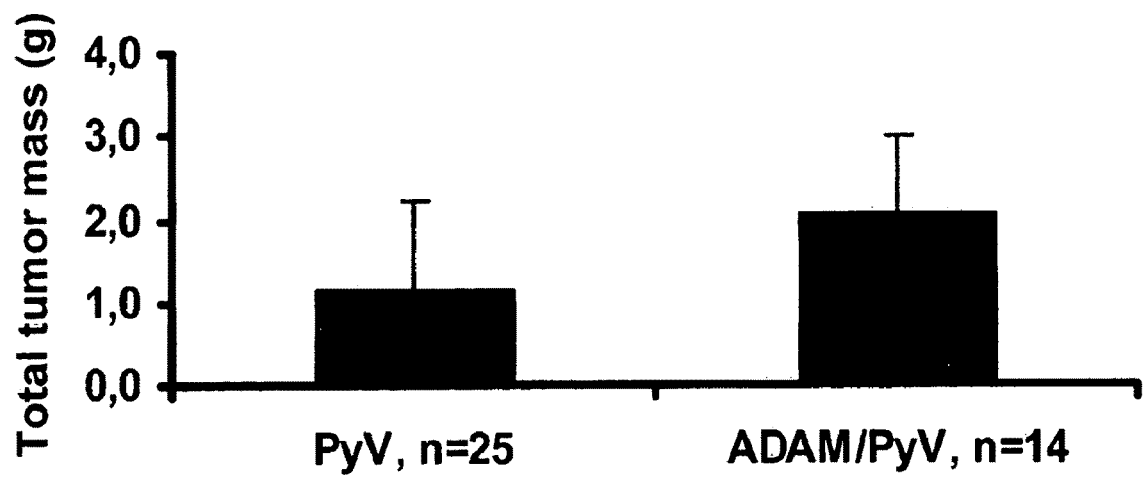
Figure 11:
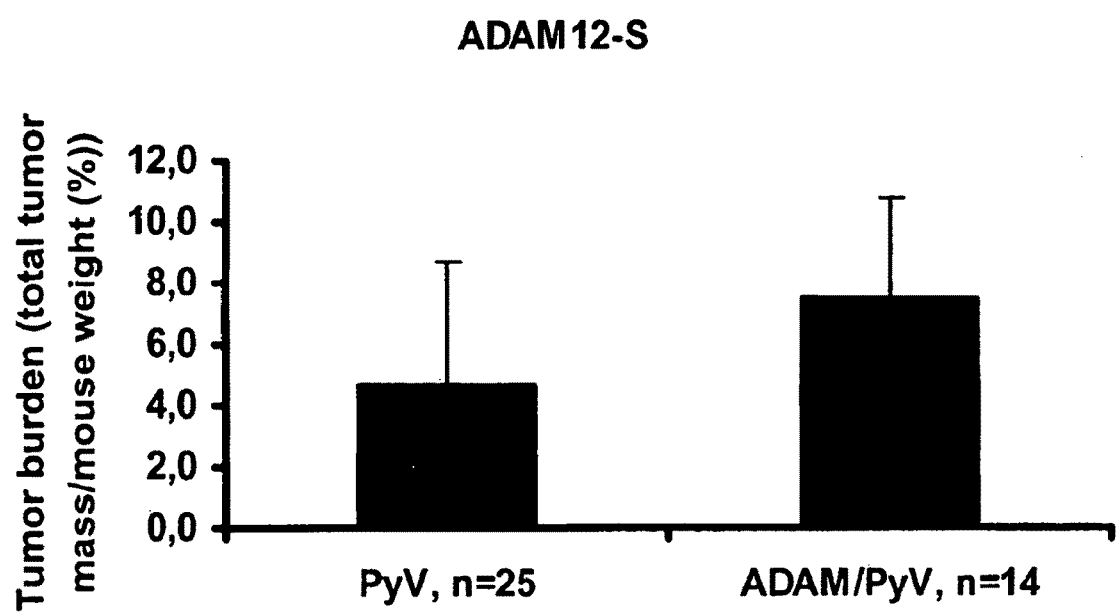
Figure 12:
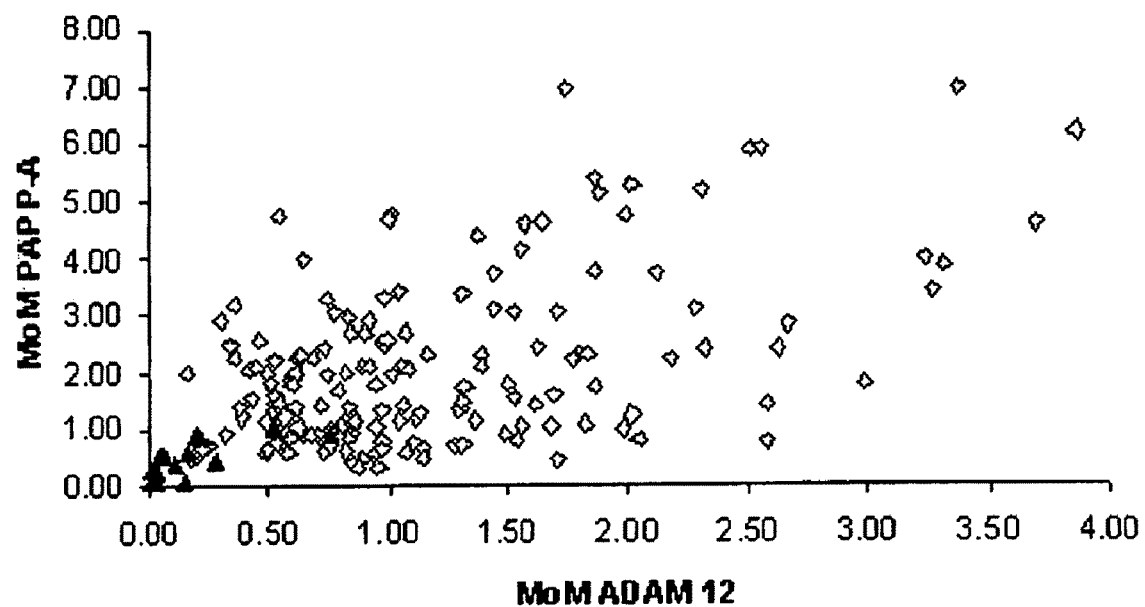
Figure 13:
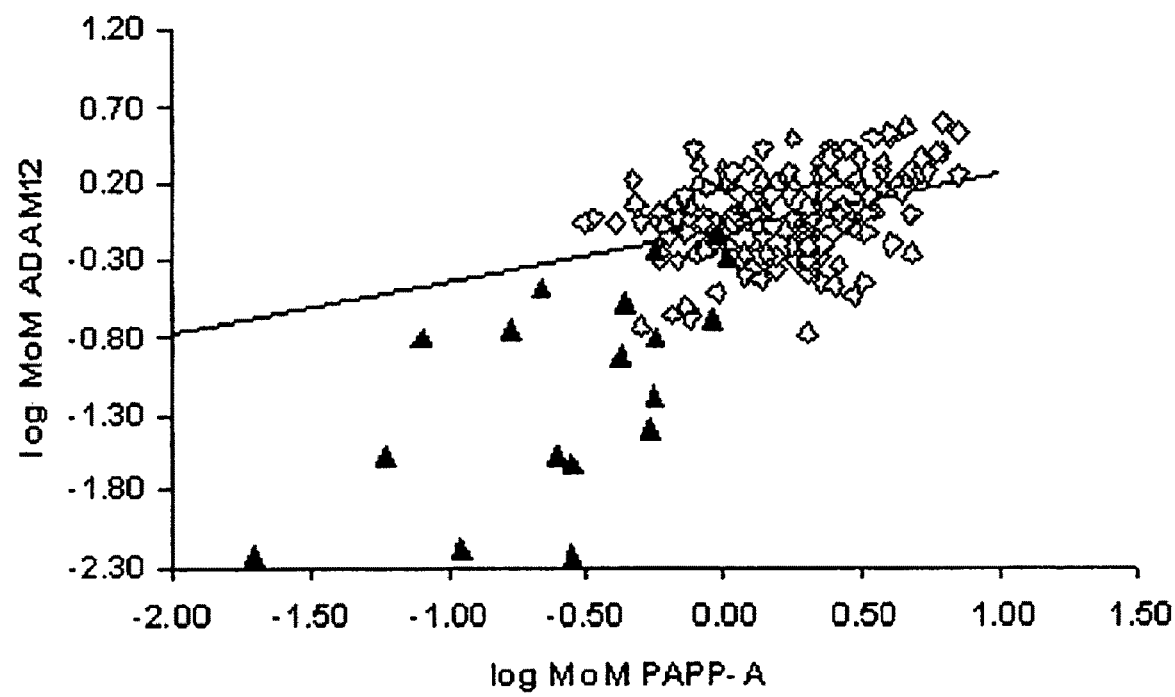
Figure 14:
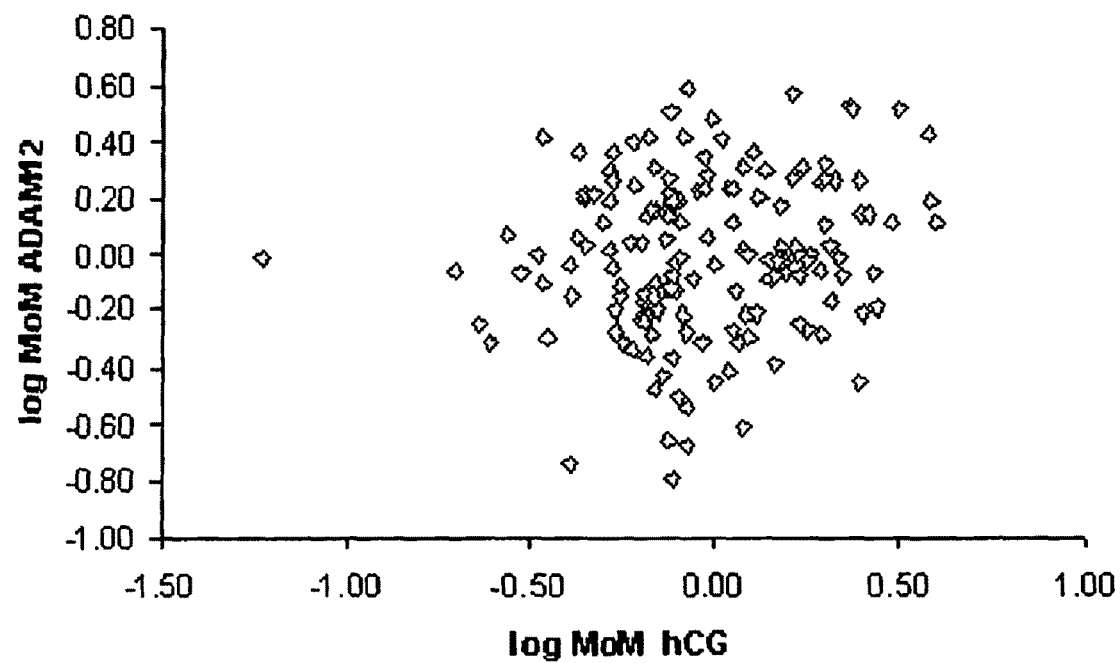
Figure 15:
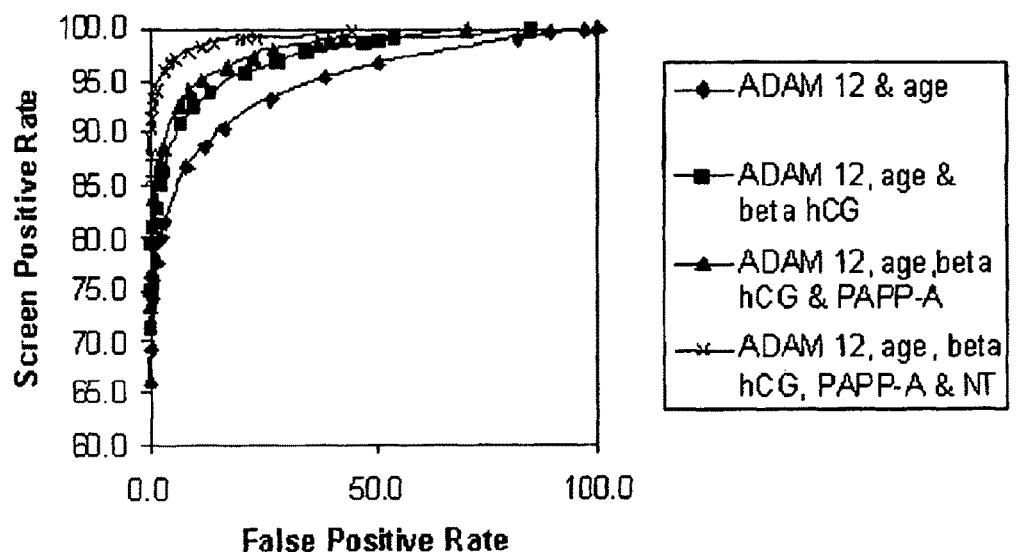
Figure 15:
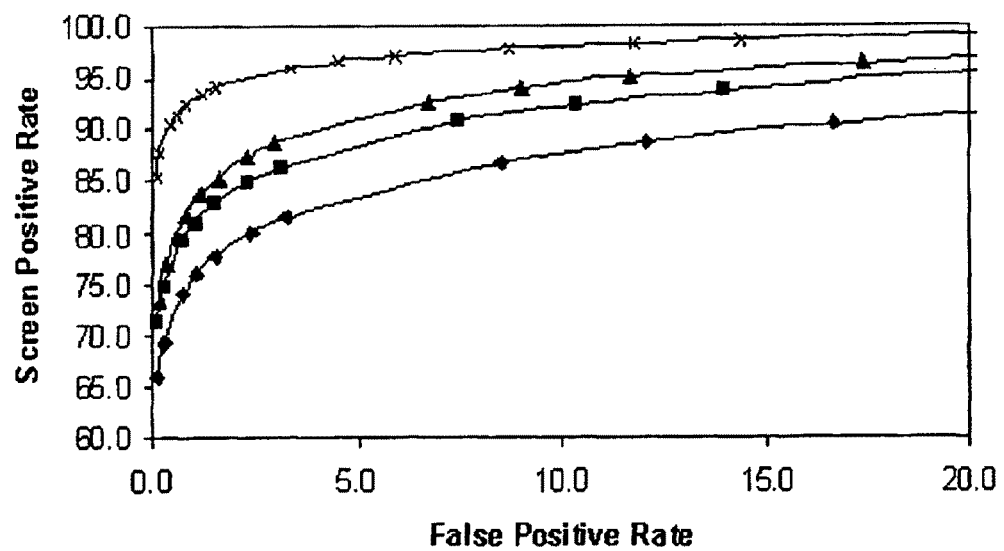
Figure 16:
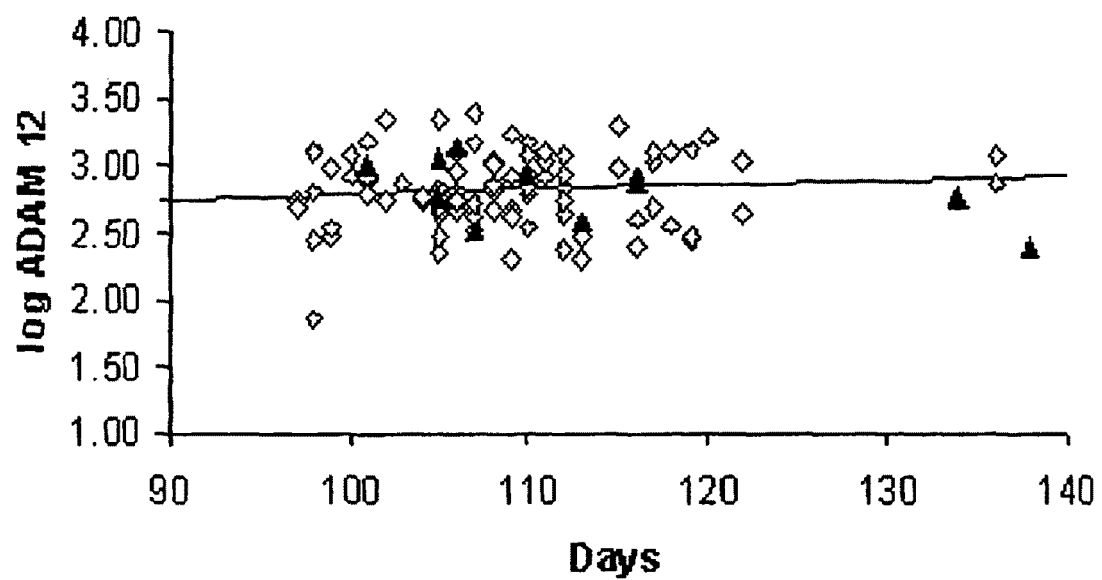
Figure 17:
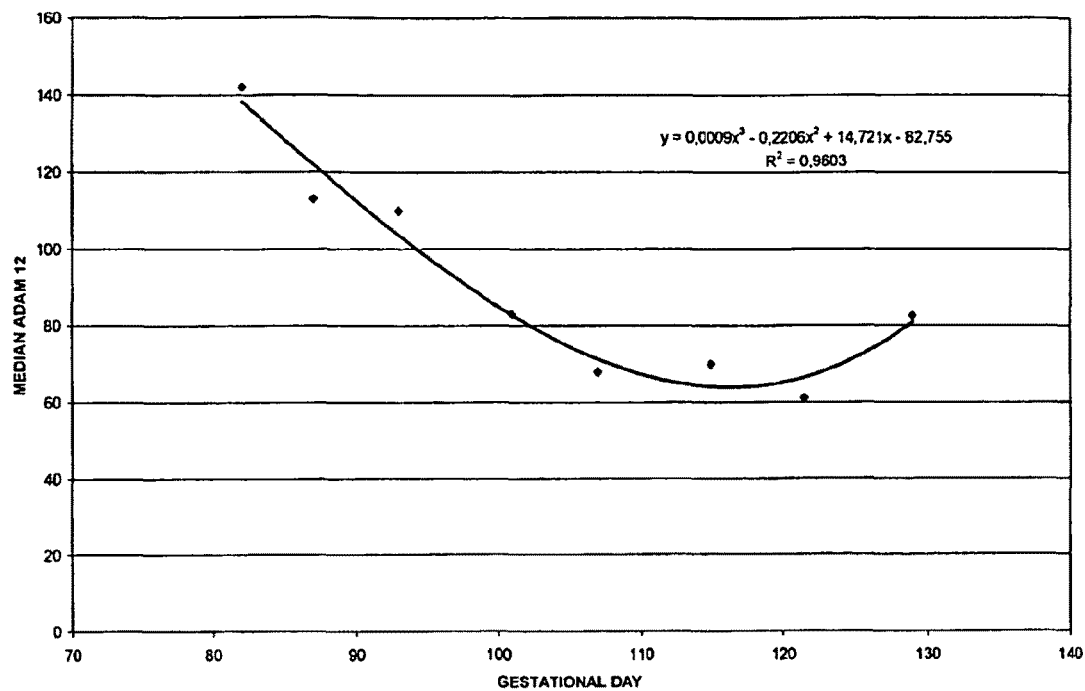
Figure 18:
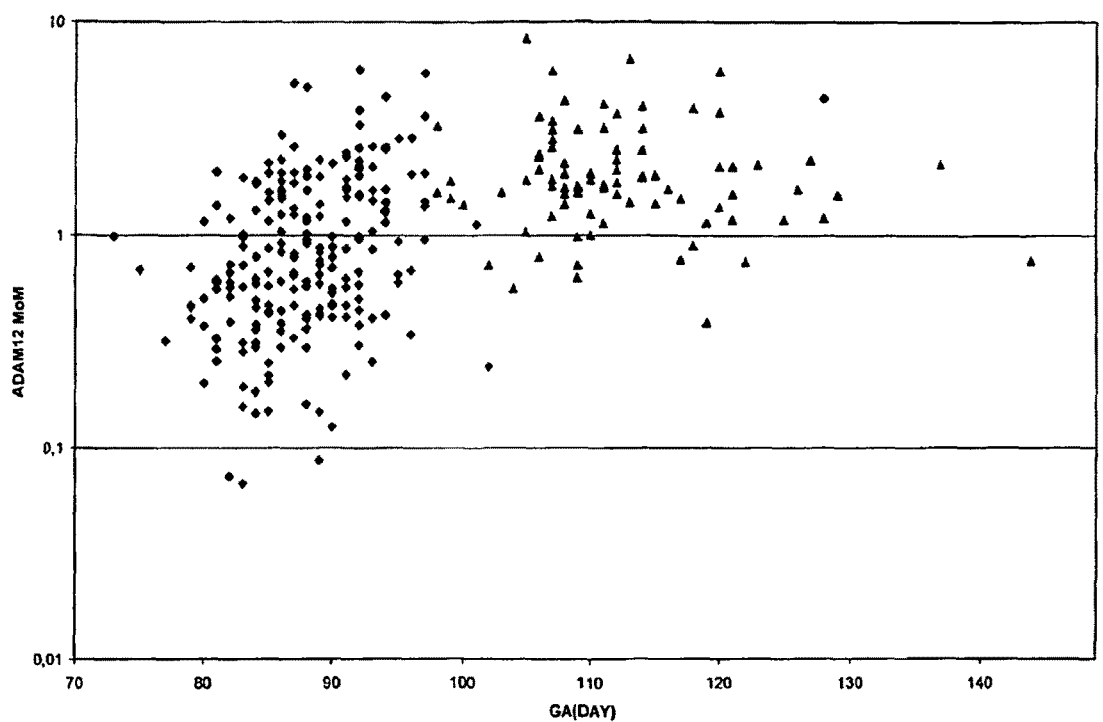
Figure 19:
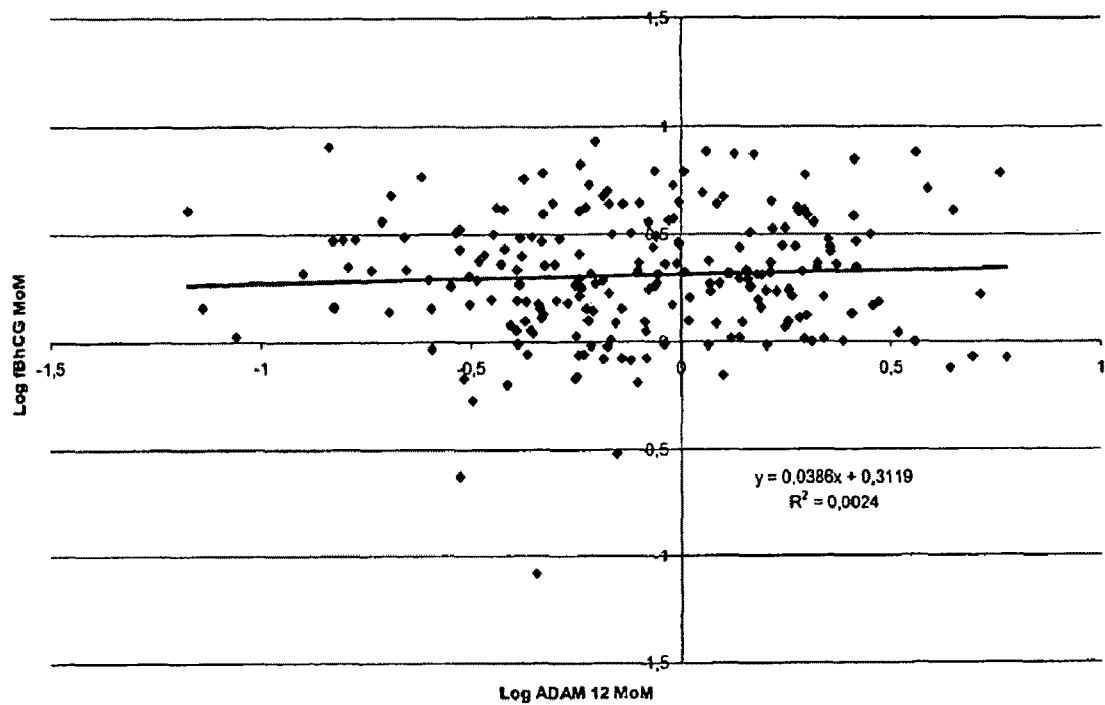

The present inventors found an approximate 60-fold increase of ADAM12 in serum throughout pregnancy. The median at 8 weeks gestation was 180 µg/l, while the median at term (after 38 full weeks) for a normal pregnancy was 12,000 µg/l. The 154 first trimester serum samples showed a significant increase with gestational age. Since the slope of the increase with gestational age that occurs in the first trimester decreased after week 10, the present inventors performed two log linear regressions: one for samples with gestational age under or equal to 70 days, and another for gestational age above 70 days. Log-linear regression resulted in median values of 180 µg/l at 8 weeks, 262 µg/l at 9 weeks, 383 µg/l at 10 weeks, and 450 µg/l at 11 weeks (FIG. 2). The gestational age window from week 10-14 is not well represented here and results mentioned below show that ADAM12 actually decreases from week 11 to 15 and then increases to reach the high term concentrations. The analysis of second trimester serum samples (n=91) and linear regression showed a slower rate of increase with median values of 592 µg/l at 14 weeks, 630 µg/l at 15 weeks, 670 µg/l at 16 weeks, and 712 at 17 weeks. Residuals were normally distributed. Analysis of term serum (n=10) showed a median of 12,000 µg/l.

The present inventors observed a significant correlation ($r=0.25$, $p<0.01$) between log MoM ADAM12 and log MoM PAPP-A and between log MoM ADAM12 and log MoM βhCG ($r=0.16$, $p<0.05$) in the first trimester, but no correlation between log MoM ADAM12 and maternal age ($r=0.05$, $p>0.05$) or nuchal translucency ($p>0.05$). The first trimester log MoM distribution of ADAM12 concentrations was compatible with a Gaussian distribution with a mean log MoM of 0.00 and standard deviation of 0.28.

ADAM12 in Down's Syndrome Pregnancies

The analysis of first trimester serum samples from pregnancies with confirmed DS (n=18) showed decreased ADAM12 concentrations, i.e. between 0 and 246 µg/l (FIG. 2). The median MoM value was 0.14 (0.01-0.76). The mean MoM of the stored supplementary 1. trimester samples was 0.17 and the mean MoM of the samples from the 1. trimester screening program was 0.29. The corresponding median MoM PAPP-A value was 0.36 (0.02-1.04). In affected pregnancies (n=18) the mean log MoM ADAM12 of −1.28 and standard deviation of 0.78 was significantly lower ($p<0.001$) than in normal pregnancies.

Table 1 demonstrates a high estimated screening performance of ADAM12 in combination with other first trimester screening markers at risk cut-offs of 1:200 and 1:400 for giving birth to a DS child.

TABLE 1

Screening performance of different screening markers at the cut-off levels 1:200 & 1:400.

| Markers | Risk > 1:200 | | Risk > 1:400 | |
|---|---|---|---|---|
| | DR | SPR | DR | SPR |
| ADAM12 & Age | 77.7 | 1.5 | 81.5 | 3.2 |
| PAPP-A & Age | 52.3 | 5.1 | 66.2 | 11.2 |
| β hCG & Age | 42.4 | 5.1 | 59.9 | 12.9 |
| NT & Age | 67.4 | 2.8 | 74.3 | 5.9 |
| ADAM12 & Age & β hCG | 82.8 | 1.5 | 86.3 | 3.1 |
| ADAM12 & Age & β hCG & PAPP-A | 85.4 | 1.6 | 88.7 | 3.0 |
| ADAM12 & Age & β hCG & PAPP-A & NT | 92.4 | 0.8 | 94.1 | 1.5 |

Example 2

Tumor Mouse

Materials and Methods

To generate the mammary gland specific ADAM12 transgenic expression, we used a modified version of the MMTV-Sv40-Bssk vector (mouse mammary virus (MMTV) long terminal repeat promoter/enhancer (LTR). Full-length ADAM12-S cDNA, and a truncated version of full-length ADAM12-L (ADAM12-Δcyt) lacking the cytoplasmtic tail were cloned into MMTV-Sv40-Bssk vector, respectively. PvuI and SpeI restriction enzymes were used to excise vector-free MMTV ADAM 2-S and MMTV ADAM12-Δcyt fragments. These fragments were used for construction of transgenic mice by microinjection of the linerized promoter transgene cassette into the male pronucleus of fertilized zygotes isolated from super-ovulated donor mice, according to standard procedures (Hogan B, Beddington R, Costantini F and Lacy E: Manipulating the Mouse Embryo: A Laboratory Manual. CSHL Press, 1994). Viable embryos were implanted into pseudopregnant recipients and allowed to develop to term. In order to generate ADAM12-S B6CBAF1 (C57Bl/6j X CBA F1) mice were used for both donors and recipients. To generate ADAM12-Δcyt mice the inbred mice strain, FVB/n, was used.

Heterozygous transgenic FVB/N-TgN(MMTVPyVT) 634Mul mice expressing PyV middle T (PyMT) antigen in the mammary gland under transcriptional control of the MMTV-LTR were obtained from Jackson Laboratories. These mice express the activated polyomavirus Middle T oncogene under control of the mouse mammary tumor virus (MMTV) long terminal repeat promoter/enhancer (LTR) and spontaneously develop multifocal mammary adenocarcinomas and metastatic tumors in the lung (Aldaz C M et al Carcinogenesis 17:2069-2072, 1996). PyMT males (FVB) were crossed with female from mice line MMTV ADAM12-S and MMTV ADAM12-Δcyt. The offsprings comprises new unique mice strains and were grouped into PyMT, MMTV-PyMT-ADAM12-S, and MMTV-PyMT-ADAM12Δcyt.

The female offspring resulting from the cross-breeding were inspected twice a week for the presence of palpable tumors. The age at onset of mammary gland tumourigenesis was scored. The number of unaffected mice as a function of age was recorded. Tumors were measured with a calliper. All the female mice were euthanized 12 weeks of age. Tumors were dissected and weighed, and the length, wide and depth were measured ($cm^3$). The absolute and relative tumour burden was evaluated (g tumour tissue and g tumour tissue/ weight of the mouse, respectively). All experiments were conducted according to the animal experimental guidelines of the Animal Inspectorate, Denmark.

Example 3

Development of an Automated Time-Resolved Immunofluorometric Assay for ADAM12

Procedure

Using the same reagents as described above, i.e. biotinylated antibody 8F8 and 6E6 were used for coating and detection and standard was recombinant ADAM12-S produced from transfected human 293-EBNA cells, a time-resolved immunofluorometric assay for ADAM12 was established: Microtiter plates (Nunc-Immuno™ Plate, MaxiSorp™ Surface, Nalge Nunc International-Denmark) were coated with 0.41 μg/well monoclonal antibody 6E6 in 0.1 M carbonate buffer (pH 9.6). Plates were washed twice after overnight incubation at 4° C. All washing steps were done with washing buffer (Delfia Wash Solution; Perkin-Elmer, Turku, Finland). Drying buffer consisting of 15 g/L bovine serum albumin (A4503, Sigma) and 25 g/L sucrose dissolved in phosphate buffered saline (PBS) was added to each well (150 uL/well) The plates were incubated 1 hour at room temperature, aspirated, and dried at 4 C overnight before being sealed with tape and stored at 4 C. After removing the sealing tape, the plate was placed in the AutoDelfia analytical automate programmed to do the following: 1. Add standard and controls, appropriately diluted in Multibuffer (Perkin-Elmer) and clinical serum samples undiluted, 100 uL/well. Incuate for 2 hours at room temperature and wash 4 times in Washbuffer (Perkin Elmer). 2. Add 100 uL/well appropriately diluted (depending on the quality of biotinylation and purification) in Multibuffer (Perkin Elmer) biotinylated 8F8 incubate for 1 hour at room temperature and wash 4 times. 3. Add 100 UL/well of Europium labeled streptavidin (Perkin Elmer) diluted 1:1000 in Multibuffer (Perkin Elmer), incubate 1 hour at room temperature followed by 3 times washing. 4. Add enhancement solution (Perkin Elmer), 200 uL/well and register fluorescence for 10 mins.

A standardcurve is made by the AutoDelfia system using a log-spline function. The standardcurve was used to calculate concentration values. Controls at 161 ug/L, 319 ug/L and 714 ug/L produced by dilution in Multibuffer (Perkin Elmer) was used as controls in each run.

Characterization

Dilution curves of recombinant ADAM12-S and pregnancy serum were linear and parallel. The mean recovery was 113% (range: 106%-120%) and between 119 ug/L and 356 ug/L the standardcurve was linear (slope: 0.91-1.00). The standard (measurement) range was 78-1248 ug/L. Sensitivity was 2.5-5 ug/L. The measurement range could be extended down to 5 ug/L. Intraassay variation at the control levels were 5.6%, 8.5% and 10.7%, for the low, medium and highest, respectively and interrassay variation was 13.3%, 10.9% and 16.0%, respectively.

Example 4

ADAM12 as a Marker of Preeclampsia

Materials and Methods

Serum samples from pregnant women were obtained from samples collected in the course of the Copenhagen First Trimester Screening Study. 160 samples were obtained from women who later in pregnancy developed preeclampsia and all the women fulfilled one of the two criteria: A systolic blood pressure >140 mm Hg and a diastolic blood pressure >90 mm Hg in a previously normotensive woman or an increase in diastolic pressure >20 mm Hg during pregnancy. 324 samples from women with uncomplicated pregnancies were analyzed as controls. Clinical and pregnancy outcome data were retrieved from the Copenhagen First Trimester Screening Study files. ADAM12-S was analyzed using the ADAM12 AutoDelfia assay as described above. All concentration values were transformed to MoM values using log-linear regression of ADAM12 concentration values on gestational age in days.

Results

In preeclamptic patients the mean log MoM ADAM12 was −0.066 (range: −1.009-0.441) significantly (p=0.008) lower than the mean logMoM ADAM12 of 0.001 (range: −1.071-0.508) in normal pregnancies.

Conclusion

The low level of ADAM12 in preeclampsia makes ADAM12 a useful risk marker for preeclampsia.

Example 5

ADAM12 in Down Syndrome Pregnancies in First and Second Trimester—British Study

Materials and Methods

Samples from pregnant women comprising 226 Downs syndrome cases from week 10-14 and 89 Down syndrome cases from second trimester referred to biochemical screening in United Kingdom by the laboratories supervised by The Fetal Medicine Foundation were used to study the distribution of ADAM12 MoM values in Downs syndrome. Representative controls were used to establish MoM distributions in normal pregnancies. ADAM12 was quantified by the immunofluorometric method described above. Performance of screening using ADAM12 alone with age or in combination with other markers was estimated by Monte Carlo simulation as described by Larsen et al., 1998 and Laigaard et al., 2003.

Results

In FIG. 1 is shown the distribution of median ADAM12 concentrations from day 80 (11-12 weeks)-day 130 (18-19 weeks). The level decreases until week 16 and increases then. The normal samples are best described by a third degree polynomial spline function as shown in FIG. 1. The regressed median MoMs were used to calculate MoM values in Down syndrome cases and the distribution of individual cases as a function of gestational age is shown in FIG. 2. It is seen from the figure that ADAM12 MoM values are very reduced in early first trimester, much less so in late first trimester and increased in second trimester. In all of first trimester the mean MoM value is 0.79 and in second trimester 1.79. The mean logMoM (SD) for Tr21 samples (n=43) taken prior to day 84 was −0.311 (0.3186) and 0.015 (0.3030) in controls (n=152). Before 84 days the detection rate(DR) of DS fetuses was estimated to be 18% for a false positive rate(FPR) of 1.4% using a risk cut-off of 1:100 for giving birth to a DS child. For the risk cut-offs 1:250 and 1:400 the DR(FPR)s were 36% (6.0%) and 48% (12%), respectively. In the gestational age window 84-97 days there was no significant difference between ADAM12 in DS pregnancies (n=172) and control pregnancies (n=341). In second trimester, the mean logMoM (SD) was 0.257 (0.2437) in Tr21 pregnancies (n=87) and 0.027(0.4136) in control pregnancies (n=341). For the risk cut-offs 1:100, 1:250 and 1:400, the estimated DR(FPR)s were and 46% (11%), respectively.

Conclusion

ADAM12 is a good maternal serum marker for fetal Down syndrome, particularly in early first and second trimester. ADAM12 supplements the markers PAPP-A, beta hCG and NT and can be used effectively in conjunction with these.

Example 6

ADAM12 as a Maternal Serum Marker for Trisomy 18—Danish Study

Materials and Methods

Serum from 10 pregnant women in first trimester with a trisomy 18 fetus were retrieved from the biobank at Statens Serum Institut, Copenhagen. 154 pregnancies with normal outcome were used as controls. Gestational age and other information was retrieved from submitted information on submission papers. ADAM12 was quantified in serum using the ELISA described above.

Results

ADAM12 was markedly reduced in trisomy 18 pregnancies, and most marked so in early first trimester. The median MoM was 0.29 as compared to 1.0 in controls.

Conclusion

ADAM12 is a marker of fetal trisomy 18 in first trimester.

Example 7

ADAM12 as a Maternal Serum Marker for Trisomy 18—British Study

Materials and Methods

Samples from pregnant women comprising 143 trisomy 18 cases and 730 control pregnancies in first and second trimester referred to biochemical screening in United Kingdom by the laboratories supervised by The Fetal Medicine Foundation were used to study the distribution of ADAM12 MoM values in trisomy 18. Representative controls were used to establish MoM distributions in normal pregnancies. ADAM12 was quantified by the immunofluorometric method described above.

Results

The maternal serum ADAM12 mean logMoM(SD) was −0.097(0.2661) in first trimester Tr18 pregnancies (n=131) and 0.312(0.2607) in second trimester Tr 18 pregnancies (n=12).

The distribution of logMoM ADAM12 values in first trimester trisomy 18 pregnancies is described in the following:

Graphical depiction of the distribution of Log ADAM12 MoM values in first trimester 18 pregnancies as shown in FIG. 29A.

Figure 30:
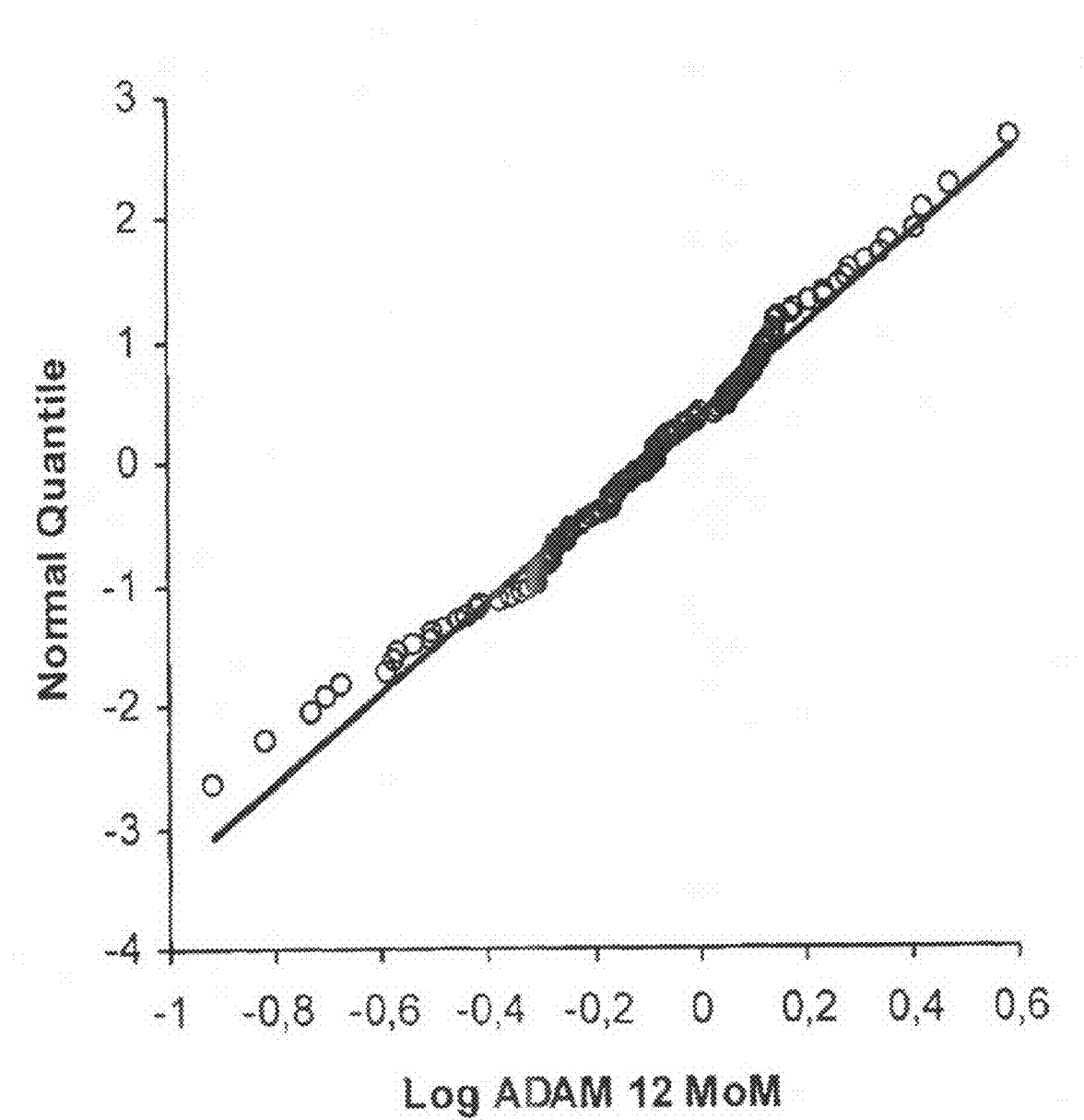

Box-and-Whisker plot of logMoM ADAM12 values in first trimester trisomy 18 pregnancies as shown in FIG. 29B A Normal probability plot of logMOM ADAM12 in trisomy 18 pregnancies as shown in FIG. 30.

Key distributional data from FIG. 29 B.

| | |
|---|---|
| Median | −0.080 |
| 96.4% CI | −0.149 to −0.042 |
| Range | 1.510756823 |
| IQR | 0.352862873 |
| Percentile | |
| 2.5th | −0.719 |
| 25th | −0.263 |
| 50th | −0.080 |
| 75th | 0.090 |
| 97.5th | 0.425 |

Statistical analysis of compliance with a normal distribution of log MoM ADAM12

| | Coefficient | p |
|---|---|---|
| Shapiro-Wilk | 0.9869 | 0.2464 |
| Skewness | −0.3574 | 0.0907 |
| Kurtosis | 0.5319 | 0.2079 |

The distribution of logMoM ADAM12 values in second trimester trisomy 18 pregnancies is described in FIG. 31 to and the following:

Graphical depiction of distributional data of LogMoM ADAM12 in second trimester trisomy 18 pregnancies as shown in FIG. 31A.

Box-and-whisker plot of the distribution of LogMoM ADAM12 data from second trimester trisomy 18 pregnancies as shown in FIG. 31B.

Statistical summary of the distribution given in FIG. 31B.

| | |
|---|---|
| Median | 0.318 |
| 96.1% CI | 0.102 to 0.547 |
| Range | 0.921011306 |
| IQR | 0.401414338 |
| Percentile | |
| 2.5th | — |
| 25th | 0.137 |
| 50th | 0.318 |
| 75th | 0.539 |
| 97.5th | — |

Normal probability plot of logMoM ADAM12 data in second trimester trisomy 18 pregnancies as shown in FIG. 32.

Tests of compliance with the normal distribution of log-MoM ADAM12 values in trisomy 18 pregnancies

| | Coefficient | p |
|---|---|---|
| Shapiro-Wilk | 0.9578 | 0.7524 |
| Skewness | −0.6157 | 0.3185 |
| Kurtosis | 0.4025 | — |

Conclusion

ADAM12 is moderately decreased in first trimester Tr18 pregnancies and markedly reduced in second trimester Tr18 pregnancies. ADAM12 is a marker for fetal Tr18 in both first and second trimester.

Example 8

ADAM12 as a Maternal Serum Marker for Trisomy 13—British Study

Materials and Methods

Samples from pregnant women comprising 66 trisomy 13 cases and 730 control pregnancies in first and second trimester referred to biochemical screening in United Kingdom by the laboratories supervised by The Fetal Medicine Foundation were used to study the distribution of ADAM12 MoM values in trisomy 13. Representative controls were used to establish MoM distributions in normal pregnancies. ADAM12 was quantified by the immunofluorometric method described above Results The maternal serum ADAM12 mean logMoM(SD) was −0.221(0.356) in first trimester Tr13 pregnancies (n=60) and 0.170(0.1853) in second trimester Tr 13 pregnancies (n=6).

First Trimester:

Graphical depiction of distributional data of LogMoM ADAM12 in first trimester trisomy 13 pregnancies as shown in FIG. 33A.

Box-nad-whisker plot of the distribution of logMoM ADAM12 data from first trimester trisomy 13 pregnancies as shown in FIG. 33B.

Statistical summary of the distribution given in FIG. 33B.

| | |
|---|---|
| Median | −0.175 |
| 97.3% CI | −0.265 to −0.035 |
| Range | 1.649930727 |
| IQR | 0.358247671 |
| Percentile | |
| 2.5th | −1.164 |
| 25th | −0.359 |
| 50th | −0.175 |
| 75th | −0.001 |
| 97.5th | 0.370 |

Normal probability plot of logMOM ADAM12 in first trimester trisomy 13 pregnancies as shown in FIG. 34.

Test of compliance with the normal distribution of logMoM ADAM12 values in first trimester trisomy 13 pregnancies.

| | Coefficient | p |
|---|---|---|
| Shapiro-Wilk | 0.9292 | 0.0018 |
| Skewness | −0.9434 | 0.0045 |
| Kurtosis | 0.8874 | 0.1605 |

Second Trimester:

Graphical depiction of the distribution of LogMoM ADAM12 data in second trimester trisomy 13 data in second trimester as shown in FIG. 35A.

Box-and-whisker plot of log MoM ADAM12 data in second trimester trisomy 13 pregnancies as shown in FIG. 35B.

Summary of statistical data from 35B.

| | |
|---|---|
| Median | 0.160 |
| 96.9% CI | −0.087 To 0.426 |
| Range | 0.513107653 |
| IQR | 0.162221942 |
| Percentile | |
| 2.5th | — |
| 25th | 0.065 |
| 50th | 0.160 |
| 75th | 0.227 |
| 97.5th | — |

Normal probability plot of logMoM ADAM12 in second trimester trisomy 13 pregnancies is shown in FIG. 36.

Test for compliance with normal distribution of LogMoM ADAM12 valuesm in second trimester trisomy 13 pregnancies.

| | Coefficient | P |
|---|---|---|
| Shapiro-Wilk | 0.9918 | 0.9931 |
| Skewness | 0.0396 | — |
| Kurtosis | −0.6852 | — |

Conclusion

ADAM12 is decreased in first and second trimester Tr13 pregnancies and ADAM12 is a marker for fetal Tr13 in both first and second trimester.

Example 9

ADAM12 as a Maternal Serum Marker for Turner Syndrome—British Study

Materials and Methods

Samples from pregnant women comprising 83 Turner syndrome cases and 730 control pregnancies in first and second trimester referred to biochemical screening in United Kingdom by the laboratories supervised by The Fetal Medicine Foundation were used to study the distribution of ADAM12 MoM maternal serum values in fetal Turner syndrome. Representative controls were used to establish MoM distributions in normal pregnancies. ADAM12 was quantified by the immunofluorometric method described above Results The maternal serum ADAM12 mean logMoM(SD) was −0.177(0.3195) in first trimester Turner syndrome pregnancies (n=77) and 0.172(0.1853) in second trimester Turner syndrome pregnancies (n=6).

The following figures describe the distributional findings in first trimester 45X0 pregnancies:

Graphic depiction of distribution of LogMoM ADAm12 values in first trimester 45X0 pregnancies as shown in FIG. 37A.

Box-and-whisker plot of log MoM ADAM12 values in 45X0 pregnancies as shown in FIG. 37B.

C. Statistical summary of the distribution shown in FIG. 37b.

| | |
|---|---|
| Median | −0.128 |
| 96.0% CI | −0.255 to −0.075 |
| Range | 1.530624082 |
| IQR | 0.345376449 |
| Percentile | |
| 2.5th | −0.916 |
| 25th | −0.353 |
| 50th | −0.128 |

|  |  |
|---|---|
| 75th | −0.007 |
| 97.5th | 0.466 |

Normal plot of logMoM ADAM12 values in first trimester 45X0 pregnancies is shown in FIG. 38.

E. Test of complicance of logMoM ADAM12 with the normal distribution in first trimester 45 X0 pregnancies.

|  | Coefficient | p |
|---|---|---|
| Shapiro-Wilk | 0.9747 | 0.1270 |
| Skewness | −0.3497 | 0.1940 |
| Kurtosis | 0.4210 | 0.3610 |

Second Trimester:

The distribution of log MoM ADAM12 values in second trimester 45X0 pregnancies was found to be as shown in the figures below:

Distribution of logMoM ADAM12 in second trimester 45 X0 pregnancies as shown in FIG. 39A.

Box-and-whisker plot of the distributional data from A as shown in FIG. 39B.

C. Statistical key parameters from FIG. 39B.

| Median | 0.163 |
|---|---|
| 96.9% CI | −0.143 to 0.494 |
| Range | 0.637059543 |
| IQR | 0.352161268 |
| Percentile |  |
| 2.5th | — |
| 25th | −0.020 |
| 50th | 0.163 |
| 75th | 0.332 |
| 97.5th | — |

Normal probability plot of log MoM ADAM12 values from 45X0 pregnancies in second trimester is shown in FIG. 40.

E. Test of the complicance of logMoM ADAM12 values from second trimester 45X0 pregnancies with normal distribution

|  | Coefficient | p |
|---|---|---|
| Shapiro-Wilk | 0.9126 | 0.4537 |
| Skewness | 0.0384 | — |
| Kurtosis | −2.2991 | — |

Conclusion

ADAM12 is decreased in first trimester Turner syndrome pregnancies and markedly increased in second trimester Turner syndrome pregnancies. ADAM12 is a marker for fetal Turner syndrome in both first and second trimester.

Example 10

ADAM12 as a maternal serum marker for non-Turner sex chromosome abnormalities (NTSCA), e.g. 47 XXX, 47 XXY, 47 XYY—British Study Materials and Methods Samples from pregnant women comprising 37 NTSCA cases and 730 control pregnancies in first and second trimester referred to biochemical screening in United Kingdom by the laboratories supervised by The Fetal Medicine Foundation were used to study the distribution of ADAM12 MoM values in NTSCA. Representative controls were used to establish MoM distributions in normal pregnancies. ADAM12 was quantified by the immunofluorometric method described above Results The maternal serum ADAM12 mean logMoM(SD) was −0.238 (0.3223) in first trimester NTSCA pregnancies (n=24) and 0.212(0.1202) in second trimester NTSCA pregnancies (n=13).

The distribution of logMoM ADAM12 values is shown below:

The distribution of logMoM ADAM12 values in first trimester NTSCA pregnancies as shown in FIG. 41A.

Box-and-whisker plot of the data depicted in A as shown in FIG. 41B.

Key statistical parameters of logMoM ADAM12 in first trimester NTSCA pregnancies—from FIG. 41B.

| Median | −0.215 |
|---|---|
| 97.7% CI | −0.339 to −0.101 |
| Range | 1.732529106 |
| IQR | 0.282772361 |
| Percentile |  |
| 2.5th | — |
| 25th | −0.365 |
| 50th | −0.215 |
| 75th | −0.082 |
| 97.5th | — |

Normal probability plot of logMoM ADAM12 in first trimester NTSCA is shown in FIG. 42.

Statistical test of the compliance of second trimester log-MoM ADAM12 values with the normal distribution.

|  | Coefficient | p |
|---|---|---|
| Shapiro-Wilk | 0.9389 | 0.1542 |
| Skewness | −0.2236 | 0.6164 |
| Kurtosis | 2.8927 | 0.0259 |

In second trimester the distribution of logMoM ADAm12 values were as described below:

Distribution of LogMoM ADAM12 values in second trimester NTSCA pregnancies as shown in FIG. 43A.

Box-and-whisker plot of the logMoM ADAM12 data from second trimester NTSCA pregnancies depicted in A as shown in FIG. 43B.

Statistical key parameters from FIG. 43B.

| Median | 0.182 |
|---|---|
| 97.8% CI | 0.083 to 0.329 |
| Range | 0.351877697 |
| IQR | 0.163993273 |
| Percentile |  |
| 2.5th | — |
| 25th | 0.142 |
| 50th | 0.182 |
| 75th | 0.306 |
| 97.5th | — |

Normal probability plot of logMoM ADAM12 data from second trimester is shown in FIG. 44.

Statistical test of the compliance of second trimester log-MoM ADAM12 values with the normal distribution.

|  | Coefficient | p |
|---|---|---|
| Shapiro-Wilk | 0.9414 | 0.4747 |
| Skewness | 0.0926 | 0.8743 |
| Kurtosis | −1.2736 | — |

Conclusion

ADAM12 is markedly decreased in first trimester NTSCA pregnancies and markedly increased in second trimester NTSCA pregnancies. ADAM12 is a marker for fetal NTSCA in both first and second trimester.

Example 11

ADAM12 as a first trimester marker in combination with other serological markers and NT (determined in week 11-13) and maternal age.—The British study The efficiency of ADAM12 as a marker of trisomy 21 is greatly enhanced if it is used in conjunction with other serological (in early first trimester PAPP-A, betahCG, proMBP or SP1) and ultrasound markers (Nuchal translucency (NT) and nasal bone and other biometric characteristics). The performance of ADAM12 was assessed using monte carlo estimation.

Results

The mean logMoM (SD) for Tr21 samples (n=43) taken prior to day 84 was −0.311 (0.3186) and 0.015 (0.3030) in controls (n=152). The correlation between markers in first trimester was found to be as shown in FIG. 19-24:

There was no correlation with Nuchal translucency and maternal age (see FIG. 23):

The following table summarises the correlations found between ADAM12 and PAPP-A and free beta-hCG in different conditions and controls in first trimester

| | | Correlation between Log ADAM 12 and Log PAPP-A/ fBhCG in the first trimester | | |
|---|---|---|---|---|
| Test Type | ADAM 12 vs. | x | $\hat{R}^2$ | ±r |
| T21 | PAPP | 0.2036 | 0.0631 | 0.2512 |
| T21 | fBhCG | 0.0386 | 0.0024 | 0.0490 |
| T18 | PAPP | 0.2114 | 0.0368 | 0.1918 |
| T18 | fBhCG | 0.1108 | 0.0088 | 0.0938 |
| T13 | PAPP | 0.5044 | 0.1293 | 0.3596 |
| T13 | fBhCG | 0.0641 | 0.0078 | 0.0883 |
| Turners | PAPP | 0.2081 | 0.0574 | 0.2396 |
| Turners | fBhCG | 0.0071 | 4.E−05 | 0.0063 |
| Control | PAPP | 0.2362 | 0.1047 | 0.3236 |
| Control | fBhCG | 0.0452 | 0.0039 | 0.0624 |

The following correlations between delta NT and ADAM12 was found in different conditions:

| Type | ADAM 12 vs. | x | $\hat{R}^2$ | ±r |
|---|---|---|---|---|
| Control | Delta NT | −0.1277 | 0.0120 | 0.1095 |
| T13 | Delta NT | 1.1253 | 0.0300 | 0.1732 |
| T18 | Delta NT | −1.6464 | 0.0254 | 0.1594 |
| T21 | Delta NT | 0.9229 | 0.0228 | 0.1510 |
| Turners | Delta NT | 4.1292 | 0.1111 | 0.3333 |

The results of the estimated performance in first trimester prior to a gestational age 84 days:

| | Estimated performance of ADAM12 in early first trimester (<week 12) in combination with other markers - British Study(Example 11) | | | | | |
|---|---|---|---|---|---|---|
| | Risk cut-off | | | | | |
| | 1:100 | | 1:250 | | 1:400 | |
| Markers | DR (%) | FPR (%) | DR (%) | FPR (%) | DR (%) | FPR (%) |
| ADAM12 + age | 29 | 2.1 | 49 | 7.0 | 60 | 12.6 |
| ADAM12 + Doubletest | 59 | 2.2 | 73 | 5.7 | 79 | 8.9 |
| ADAM12 + Doubletest + NT | 78 | 1.1 | 85 | 2.7 | 88 | 4.3 |

DR Detection rate.
FPR False positive rate.
Estimation was performed as described in Larsen et al., J Med Screen 1998; 5: 57-62
Parameters of PAPP-A and betahog were obtained from Cuckle & Van Lith Prenat Diagn 1999; 19: 505-512

Conclusion: ADAM12 is a very efficient early first trimester trisomy 21 marker when used in conjunction with other first trimester markers. This is the preferred use of the marker.

Example 12

ADAM12 as a Second Trimester Marker of Trisomy 21 in Combination with Other Serological Markers and Maternal Age—The British Study The efficiency of ADAM12 as a marker of trisomy 21 is greatly enhanced if it is used in conjunction with other serological (in second trimester AFP and betahCG) and possibly ultrasound markers. The performance of ADAM12 was assessed using monte carlo estimation.

Results

In second trimester, the mean ADAM12 logMoM (SD) was 0.257 (0.2437) in Tr21 pregnancies (n=87) and 0.027(0.4136) in control pregnancies (n=341). The correlation between markers in second trimester was found to be as shown in FIG. 25-29:

| | | Correlation between Log ADAM 12 and Log AFP/ fBhCG in the second trimester | | |
|---|---|---|---|---|
| Type | ADAM 12 vs. | x | $\hat{R}^2$ | ±r |
| T21 | AFP | 0.0687 | 0.0061 | 0.0781 |
| T21 | fBhCG | −0.0789 | 0.0054 | 0.0735 |
| Control | AFP | 0.0348 | 0.0086 | 0.0927 |
| Control | fBhCG | 0.1034 | 0.0208 | 0.1442 |

Estimated performance of ADAM12 in second trimester (>week 13) in combination with other markers - British Study

| Markers | Risk cut-off | | | | | |
|---|---|---|---|---|---|---|
| | 1:100 | | 1:250 | | 1:400 | |
| | DR (%) | FPR (%) | DR (%) | FPR (%) | DR (%) | FPR (%) |
| ADAM12 + age | 21 | 1.6 | 40 | 6.4 | 53 | 12.7 |
| ADAM12 + AFP + betahOG | 47 | 2.3 | 66 | 7.0 | 76 | 11.6 |

DR Detection rate.
FPR False positive rate.
Estimation was performed as described in Larsen et al., J Med Screen 1998; 5: 57-62
Parameter were from Rode et al., Prenat Diagn 2003; 23: 593-598.

Conclusion: ADAM2 is a very efficient second trimester maternal serum marker for fetal trisomy 21 when used in conjunction with other second trimester markers. This is the preferred use of the marker.

Example 13

ADAM12 in Preeclampsia—The British Study

In Harold Wood Hospital (Essex) and Fetal Medicine Centre (London), all pregnant women are offered screening for trisomy 21 by a combination of fetal nuchal translucency and maternal serum free β-hCG and PAPP-A in a One Stop Clinic for Assessment of Risk (OSCAR)[18]. Demographic characteristics, ultrasound findings and the results of biochemical testing are entered into a computer database at the time of assessment. All samples are stored at −20 celcius after routine analysis.

A search was made of the database to identify all singleton pregnancies, which had combined first trimester screening. The hospital notes and delivery suite records were then searched for each one of these patients to identify any pregnancy complicated by pre-eclampsia and obtain delivery details. Pre-eclampsia was defined by a diastolic blood pressure of 110 mmHg or more on any one occasion or a diastolic blood pressure of 90 mm Hg or more on two consecutive occasions four hours apart in women with no pre-existing hypertensive or renal disease, and the presence of either more than 300 mg of total protein in a 24-hour urine collection or an 1+ albumin on reagent strip.[20] In total 67 cases were identified of which 33 were defined as severe based on the need for delivery before 35 weeks. As controls a series of cases matched for gestational age and storage time were retrieved along with the cases for analysis of ADAM12 using a Delfia research fluorimmunoassay.

In addition as part of a research study incorporating uterine artery Doppler measurement, 75 control samples and 12 cases with PET were collected at the time of the Doppler investigations at 23 or 24 weeks gestation. These samples were also analysed for ADAM12.
Results In the group of cases collected in the first trimester the median MoM ADAM12 of the total Pre-eclamptic group was lower than normal with a median MoM of 0.90. In the group with severe pre-eclampsia the median was even lower at 0.75 MoM. In the Cases at 23-24 weeks the median MoM in the preclampsia group was slightly higher than normal with a median MoM of 1.14.

Conclusion: The results confirm the data given in example 4. Furthermore, ADAM12 may be a useful marker of pre-clampsia also in second trimester.

Example 14

Calculation of Gestational Age Independent Values of ADAM12

Due to the great variation of ADAM12 values in pregnancies at the same gestational age and the increase in ADAM12 with age it is generally not possible to use the absolute concentration of ADAM12 in serum as a marker. It is necessary to normalise it to the gestational age. This is done by expressing the maternal serum level of ADAM12—determined directly or indirectly by whatever means—as a function of the level expected among normal women at the same time in gestation. Gestational age may be expressed as days after last menstruation, as a fetal biometric marker or anything else suitable to represent the change in ADAM12 with progressing pregnancy.

One way of making a gestational age independent ADAM12 values is the use of multiples of the median for a specific gestational age window, e.g. by calculating empirical medians for each week or day. Alternatively, empirical medians can be calculated using other markers correlating with gestational age, e.g crown rump length and bipariuetal diameter. The latte procedure will often be the preferred use of ADAM12.

Example 15

ADAM12 as a Marker of Trisomy 21 and 18 in Gestational Week 10-12 Leeds Study

The aim of the study was to establish the performance of ADAM12 as a maternal serum marker for trisomy 21 and 18 in the gestational age window week 10-12 where previous studies have suggested that the discriminatory power of ADAM12 may be negligible. The concentration of ADAM12 was determined using an immunofluorometric assay in 268 control pregnancies and 20 samples from pregnancies with fetal trisomy 21 (n=16) and trisomy 18 (n=4). Samples were collected at the Screening Centre at Leeds, stored at −20 deg C. and controls and samples were matched for length of storage and number of freeze-thaw cycles.

Results. Median values of ADAM12 for each gestational week were estimated by log-linear regression. The estimated ADAM12 medians were 214 ug/L in week 9, 275 ug/L in week 10, 353 ug/L in week 11, 454 ug/L in week 12 and 584 ug/L in week 13. All sample ADAM12 concentrations were transformed into logMoM values and the distribution of log-MoM ADAM12 in controls was: mean: 0.000, standard deviation: 0.326. In the 16 Ds samples the mean log ADAM12 MoM was −0.044, and not significantly different fro controls (p=0.55). In DS pregnancies the mean ADAm12 MoMs were: 1.09 in week 9 (n=1), 0.9968 in week 10 (n=5), 0.8223 in week 11 (n=9) and 1.113 in week 12 (n=1). In trisomy 18 pregnancies the ADAM12 MoM values 1.92, 0.765, 1.705 and 2.09 were obtained in weeks 9,11,12 and 13, respectively.

Conclusion: ADAM12 is not a good maternal serum marker for trisomy 21 in week 10-12, whereas it does seem to be a good marker for trisomy 18. It is very important to use ADAM12 in the correct gestational age window and use logMoM values when using ADAM12 as a marternal serum marker for chromosomal disease. This study is an independent confirmation of the finding in the Danish study (Laigaard et al., 2003) and the British study described above (Example 5)

The invention will now be further described by the following numbered paragraphs:

1. A method for screening for fetal abnormality in a fetus said method comprising the steps of:
   a) providing a body sample from an individual
   b) determining the level of ADAM12 in said sample by detecting
      1) ADAM12 polypeptide and/or
      2) a polynucleotide coding for ADAM12 expression, and/or
      3) specific ADAM12 protease activity, preferably by detecting cleavage of IGFBP-3, a derivative thereof, or any other suitable substrate for ADAM12.
   c) comparing said level with a reference level;
   d) identifying whether the level is different from said reference level and
   evaluating whether the fetus has an increased risk of fetal abnormality and/or adverse pregnancy outcome, if the level is different from the reference level.
2. A method according to paragraph 1, wherein said biological sample is selected from the group consisting of blood, urine, pleural fluid, oral washings, tissue biopsies, and follicular fluid.
3. A method according to any of the preceding paragraphs, wherein said biological sample is selected from the group consisting of blood, plasma and serum.
4. A method according to any of the preceding paragraphs, wherein said biological sample is serum.
5. A method according to any of the preceding paragraphs, wherein said fetal abnormality and/or adverse pregnancy outcome is selected from the group consisting of placenta disease or dysfunction, trisomy 21, trisomy 18, trisomy 13, preeclampsia, intra uterine growth retardation, ectopic pregnancy, open spina bifida, neural tube defects, ventral wall defects, Edwards Syndrome, Pateaus Syndrome, Turner Syndrome, Monosomy X, triploidies, monoploidies, small-for-gestational-age and Kleinfeiter's Syndrome.
6. A method according to 5, wherein said fetal abnormality and/or adverse pregnancy outcome is trisomy 21.
7. A method according to 5, wherein said fetal abnormality and/or adverse pregnancy outcome is preeclampsia.
8. A method according to 5, wherein said fetal abnormality and/or adverse pregnancy outcome is trisomy 18.
9. A method according to 5, wherein said fetal abnormality and/or adverse pregnancy outcome is trisomy 13.
10. A method according to 5, wherein said fetal abnormality and/or adverse pregnancy outcome is Turner syndrome.
11. A method according to 5, wherein said fetal abnormality and/or adverse pregnancy outcome is non-Turner sex chromosome abnormalities (NTSCA).
12. A method according to any of paragraphs 1-11, wherein ADAM12 is assessed as a first trimester marker.
13. A method according to any of paragraphs 1-11, wherein ADAM12 is assessed as a second trimester marker.
14. A method according to any of the paragraphs 1-13, wherein the ADAM12 level is combined with values from at least one marker selected from the group consisting of alpha feto-protein (AFP), unconjugated oestrol (uE3), human chorionic gonadotrophin (hCG), free alpha sub-unit of hCG (free α-hCG), free beta sub-unit of hCG (free β-hCG), beta-core hCG, hyperglycosylated hCG (ITG), placental growth hormone (PGH), inhibin, preferably dimeric inhibin-A (inhibin A), pregnancy-associated plasma protein A (PAPP-A), Complexes of PAPP-A with proMBP (proform of major basic protein), ProMBP, ProMBP complexes with angiotensinogen and/or complement factors and split products, Schwangerschaftsprotein 1(SP1), Cancer antigen 125(CA125), Prostate specific antigen (PSA), Leukocyte enzymes, fetal DNA, fetal RNA, fetal cells, stem cells, oestradiol, Ultrasound markers, Nuchal translucency, Femur length, Absence of nasal bone, Hyperechogenic bowel, Echogenic foci in the heart, Choroids plexus cysts, Hydronephrosis, Fetal malformations, Steroids, Peptides, Chemokines, Interleukins (e.g. IL-6, IL-4, IL-1), Tumor necrosis factor, Transforming growth factor alpha and beta, Acute phase reactants, C-reactive protein, Fibronectin, Maternal or fetal Single nucleotide polymorphisms, e.g. promoter region polymorphisms in TNFbeta and mannan-binding lectin, Complement components, HLA-G and HLA molecules.
15. A method according to any of the paragraphs 1-14, wherein gestational age independent (MOM) or value of ADAM12 is calculated for use in risk assessment in fetal or placenta diseases.
16. A method according to any of the paragraphs 1-15, wherein the gestation age independent ADAM12 (MOM) is used in conjunction with biometric, serological or clinical information to derive a risk for developing pre-eclampsia.
17. A method according to any of the paragraphs 1-16, wherein the sample is obtained prior to gestational age of week 11 and/or after gestational age of week 12.

REFERENCES

EP 1 524 523

Blat C, Villaudy 3, Binoux M. 1994. In vivo proteolysis of serum insulin-like growth factor (IGF) binding protein-3 results in increased availability of IGF to target cells. 3 Clin Invest 93: 2286-2290.

Canick and Knight, supra (April 1992).

Cuckle H S, van Lith J M. 1999. Appropriate biochemical parameters in first-trimester screening for Down syndrome. Prenat Diagn 19: 505-512.

Cuckle H S, Wald N J, Thompson S G. 1997. Estimating a woman's risk of having a pregnancy associated with Down's syndrome using her age and serum alpha-fetoprotein level. Br J. Obstet Gynaecol 94, 387-402.

Gilpin B J, Loechel F, Mattel M G, Engvall E, Albrechtsen R, Wewer U M. 1998. A novel secreted form of human ADAM12 (meltrin alpha) provokes myogenesis in vivo. 3 Biol Chem 273: 157-166.

Iba K, Albrechtsen R, Gilpin B J, Loechel F, Wewer U M. 1999. Cysteine-rich domain of human ADAM12 (meltrin α) supports tumour cell adhesion. Am J Pathol 154: 1489-1501.

Kawaguchi N, Xu X, Tajima R, Kronqvist P, Sundberg C, Loechel F, Albrechtsen R, Wewer U M. 2002. ADAM12 protease induces adipogenesis in transgenic mice. Am J Pathol 160: 1895-1903.

Kronqvist P, Kawaguchi N, Albrechtsen R, Xu X, Schroder H D, Moghadaszadeh B, Nielsen F C, Frohlich C, Engvall E, Wewer U M. 2002. ADAM12 alleviates the skeletal muscle pathology in mdx dystrophic mice. Am J Pathol 161: 1535-1540.

Laigaard J, Sørensen T, Frölich C, Nørgaard-Pedersen B, Christiansen M, Schiott K, Uldbjerg N, Albrechtsen R, Clausen H. V, Ottesen B, Wewer U M. 2003. ADAM12: a novel first-trimester maternal serum marker for Down syndrome. Prenatal Diagnosis 23: 1086-1091.

Laigaard J, Christiansen M, Fröich C, Nørgaard-Pedersen B, Ottesen B, Wewer U M. 2005. The level of ADAM12-S in maternal serum is an early first trimester marker of fetal trisomy 18. Prenatal Diagnosis 25: 45-46.

Larsen S O, Christiansen M, Nørgaard-Pedersen B. 1998. Calculation of roc curves in multidimensional likelihood ratio based screening with Down's syndrome as a special case. J Med Screen 5(2): 57-62

Laursen L S, Overgaard M T, Soe R, Boldt H B, Sottrup-Jensen L, Giudice L C, Conover C A, Oxvig C. 2001. Pregnancy-associated plasma protein-A (PAPP-A) cleaves insulin-like growth factor binding protein (IGFBP-5) independent of IGF: implications for the mechanism of IGFBP-4 proteolysis by PAPP-A. FEBS-Lett 504: 36-40.

Le Pabic H, Bonnier D, Wewer U M, Countand A, Musso O, Baffet G, Clement, B, Théret N. ADAM12 in human liver cancers: TGFb-regulated expression in stellate cells is associated with matrix remodelling. Hepatology, 37:1056-1066, 2003

Loechel F, Gilpin B J, Engvall E, Albrechtsen R, Wewer U M. 1998. Human ADAM12 (meltrin α) is an active metalloprotease. J Biol Chem 273: 16993-16997.

Loechel F, Fox J W, Murphy G, Albrechtsen R, Wewer U M. 2000. ADAM12-S cleaves IGFBP-3 and IGFBP-5 and is inhibited by TIMP-3. Biochem Biophys Res Commun 278: 511-515.

Palomaki et al., "Maternal Serum Screening for Fetal Down Syndrome in the United States: A 1992 Survey," Am. J. Obstet. Gynecol., 169(6): 1558-1562 (1992).

Powel-Braxton L, Hollingshead P, Warburton C, Dowd M, Pitts-Meek S, Dalton D, Gillet N, Stewart T A. 1990. IGF-I is required for normal embryonic growth in mice. Gen Dev 7: 2609-2617.

Roy, R., U. M. Wewer, M A Moses. Urinary ADAM12: Correlation with disease status and stage in breast cancer. Abstract to the AACR meeting 2004.

Bindra R, Heath V, Liao A, Spencer K, Nicolaides K. 2002. One-stop clinic for assessment of risk for trisomy 21 at 11-14 weeks: a prospective study of 15030 pregnancies. Ultrasound Obstet Gynecol 20; 219-225.

Shi Z, Xu W, Loechel F, Wewer U M, Murphy U. 2000. ADAM12, a disintegrin and metalloprotease, interacts with insulin-like growth factor-binding protein-3. J Biol Chem 275: 18574-18580.

van der Veen 3, Beekhuis J R, Cornel M C, Mantingh A, de Walle H E, de Wolf B T. 1997. A demographic approach to the assessment of Down syndrome screening performance. Prenat Diagn 17: 717-724.

Wald N J, Watt H C, Hackshaw A K. Integrated screening for Down's syndrome on the basis of tests performed during the first and second trimesters. 1999. N Engl J Med 341: 461-467.

Wald N J, Hackshaw A K. 2000. Advances in antenatal screening for Down syndrome. Bailliereres Best Pract Res Clin Obstet Gynaecol 14: 563-80.

The invention claimed is:

1. A method for screening for risk of Down's Syndrome in a fetus said method comprising the steps of:
    a) determining the level of ADAM12 polypeptide in a biological sample obtained from a pregnant woman in the first trimester and
    b) comparing said level with a reference ADAM12 polypeptide level obtained from control groups comprising ADAM12 polypeptide levels obtained from women pregnant with a normal fetus at the same gestational age;
    wherein a decrease in the ADAM12 polypeptide level in the first trimester indicates an increased risk of Down's syndrome in the fetus.

2. A method according to claim 1, wherein said biological sample is selected from the group consisting of blood, urine, pleural fluid, oral washings, tissue biopsies, and follicular fluid.

3. A method according to claim 1, wherein said biological sample is selected from the group consisting of blood, plasma and serum.

4. A method according to claim 3, wherein said biological sample is serum.

5. A method according to claim 1, wherein the ADAM12 level is combined with values from at least one marker selected from the group consisting of alpha feto-protein (AFP), unconjugated oestrol (uE3), human chorionic gonadotrophin (hCG), free alpha sub-unit of hCG (free α-hCG), free beta sub-unit of hCG (free (β-hCG), beta-core hCG, hyperglycosylated hCG (ITG), placental growth hormonre (PGH), inhibin, preferably dimeric inhibin-A (inhibin A), pregnancy-associated plasma protein A (PAPP-A), Complexes of PAPP-A with proMBP (proform of major basic protein), ProMBP, ProMBP complexes with angiotensinogen and/or complement factors and split products, Schwangerschaftsprotein 1(SP1), Cancer antigen 125(CA125), Prostate specific antigen (PSA), Leukocyte enzymes, fetal DNA, fetal RNA, fetal cells, stem cells, oestradiol, Ultrasound markers, Nuchal translucency, Femur length, Absence of nasal bone, Hyperechogenic bowel, Echogenic foci in the heart, Choroids plexus cysts, Hydronephrosis, Fetal malformations, Steroids, Peptides, Chemokines, Interleukins (e.g. IL-6, IL-4, IL-1), Tumor necrosis factor, Tranforming growth factor alpha and beta, Acute phase reactants, C-reactive protein, Fibronectin, Maternal or fetal Single nucleotide polymorphisms, e.g. promoter region polymorphisms in TNFbeta and mannan-binding lectin, Complement components, HLA-G and HLA molecules.

6. A method according to claim 1, wherein gestational age independent (MOM) or value of ADAM12 is calculated for use in risk assessment in fetal or placenta diseases.

7. A method according to claim 1 wherein the biological sample is obtained prior to week 11.

* * * * *